US006005103A

United States Patent [19]

Domagala et al.

[11] Patent Number: 6,005,103

[45] Date of Patent: Dec. 21, 1999

[54] PYRONE DERIVATIVES AS PROTEASE INHIBITORS AND ANTIVIRAL AGENTS

[75] Inventors: John Michael Domagala, Canton; Elizabeth Lunney, Ann Arbor; Kimberly Suzanne Para, Ann Arbor; Josyula Venkata Nagendra Vara Prasad, Ann Arbor; Bradley Dean Tait, Canton, all of Mich.

[73] Assignee: Warner-Lambert Company, Morris Plains, N.J.

[21] Appl. No.: 08/319,769

[22] Filed: Oct. 12, 1994

Related U.S. Application Data

[63] Continuation-in-part of application No. 08/155,028, Nov. 19, 1993, abandoned.

[51] Int. Cl.[6] ...................... C07D 309/00; C07D 319/00; C07D 409/00; C07D 405/00

[52] U.S. Cl. ............................ 544/60; 544/149; 544/360; 546/280.1; 546/282.1; 548/202; 548/238; 549/28; 549/273; 549/274

[58] Field of Search .................................... 549/273, 274, 549/28; 544/60, 149, 360; 546/280.1, 282.1; 548/202, 238

[56] References Cited

U.S. PATENT DOCUMENTS

| | | | |
|---|---|---|---|
| 3,206,476 | 9/1965 | Collins | 766/36 |
| 3,818,046 | 6/1974 | Harris et al. | 766/30 |
| 3,931,235 | 1/1976 | Harris et al. | 791/30 |

FOREIGN PATENT DOCUMENTS

| | | | |
|---|---|---|---|
| 0588137A1 | 3/1994 | European Pat. Off. . | |
| 1422494 | 11/1965 | France . | |
| 3724M | 12/1966 | France . | |
| 3-227923 | 10/1991 | Japan . | |
| 3227923A | 10/1991 | Japan . | |
| 89/07939 | 9/1989 | WIPO . | |
| 8907939 | 9/1989 | WIPO . | |
| 93/10645 | 11/1992 | WIPO | 549/292 |
| 94/11361 | 5/1994 | WIPO . | |
| 94/18188 | 8/1994 | WIPO . | |

OTHER PUBLICATIONS

S. Thaisrivangs, et al., *J. Med. Chem.*, 1994, 37, 3200–3204.

M. Ruwart, et al., *American Association of Pharmaceutical Scientists Meeting—Abstract/PDD 7290*, Nov. 6–10, 1994, San Diego.

C. Goetschel and C. Mentzer, *Bull Soc Chim Fr*, 1962, No. 75, p. 365.

N. Kohl, et al., *Proc. Nat. Acad. Sci. USA*,85:1988,4689–90.

J.C. Craig, et al, *Antiviral Research*, 16:1991, 295–305.

A.G. Tomasselli, et al., *Chimica Oggi*, 9:1991,6–27.

T. Meek, *J. Enzyme Inhibition*, 6: 1992, 65–98.

R. Nagorny, et al, *AIDS*, 7:1993, 129–130.

D.P. Fairlie, et al., *Biochem. Biophys. Res. Comm.*, 188: 1992, 631–637.

D. Richman, "Control of Virus Diseases," 45th Symposium of the Society for General Microbiology, 1990, 261–313.

H. Toh, et al., *Nature*, 1985, 315:691.

J. Kay, et al., *Biochim. Biophys. Acta* 1: 1990, 1048.

C. Cameron, et al., *J. Biological Chem.* 168, 1993, 11711–7.

M. Graves, *Structure and Function of the Aspartic Protease* 1991, 395–405.

C. Peng, et al., *J. Virol.*,63: 1989, 2550–2556.

*Primary Examiner*—John Kight
*Assistant Examiner*—Raymond Covington
*Attorney, Agent, or Firm*—Elizabeth M. Anderson

[57] ABSTRACT

The present invention relates to novel tri- and tetrasubstituted pyrones and related structures which potently inhibit the HIV aspartyl protease blocking HIV infectivity. The pyrone derivatives are useful in the development of therapies for the treatment of bacterial and viral infections and diseases, including AIDS. The present invention is also directed to methods of synthesis of multifunctionalized pyrones and of related structures.

19 Claims, No Drawings

PYRONE DERIVATIVES AS PROTEASE INHIBITORS AND ANTIVIRAL AGENTS

The is a Continuation-in-Part application of U.S. Ser. No. 08/155,028, filed Nov. 19, 1993, now abandoned.

TABLE OF CONTENTS

1. FIELD OF THE INVENTION
2. BACKGROUND OF THE INVENTION
3. SUMMARY OF THE INVENTION
4. DETAILED DESCRIPTION OF THE INVENTION
4.1 General Synthetic Approaches to Pyrone Derivatives
4.2 General Procedures for the Preparation of Functionalized Pyrones
4.3 Preparation of Starting Materials
4.4 Preparation of Specific Pyrone Derivatives
4.5 Determination of HIV Protease Inhibition
4.5.1 Starting Materials
4.5.2 Assay
4.6 Anti-HIV-1 Activity

1. FIELD OF THE INVENTION

The present invention relates to pyrone derivatives that are inhibitors of aspartyl proteases, in particular the aspartyl proteases found in retroviruses including Human Immunodeficiency Virus (HIV). The pyrones are expected to have utility as antiviral agents, for the treatment of infection caused by HIV or other retroviruses employing aspartyl proteases, and to be useful in the treatment of diseases caused by the retroviruses, including AIDS.

2. BACKGROUND OF THE INVENTION

Acquired Immunodeficiency Syndrome (AIDS) was coined in 1982 to describe the clinical manifestations of immunodeficiency. The etiological agent of AIDS was later associated with a retrovirus, Human Immunodeficiency Virus (HIV), from the lentivirus subfamily. At least two infectious strains of HIV have been identified, HIV-1 and HIV-2. Here, HIV will be used as a general term describing a variety of strains and mutants of the Human Immunodeficiency Virus. The detailed study of HIV has given rise to many approaches to antiviral drug development including inhibition of the viral aspartyl protease (D. Richman, *Control of Virus Diseases,* 45th Symposium of the Society for General Microbiology, 261–313 (1990)).

Aspartyl proteases have been found in many retroviruses including the Feline Immunodeficiency Virus, the Myeloblastosis Associated Virus, HIV, and the Rous Sarcoma Virus [H. Toh et al., Nature, 315: 691 (1985); J. Kay, B. M. Dunn, *Biochim. Biophys. Acta,* 1: 1048 (1990); C. Cameron et al., *J. Biological Chem.,* 168, 11711–720 (1993)]. Since there are structural similarities among the known retroviral proteases, compounds which inhibit the HIV protease may well inhibit other retroviral proteases.

HIV aspartyl protease is responsible for post-translational processing of viral precursor polyproteins such as pol and gag. (M. Graves, *Structure and Function of the Aspartic Proteases,* 395–405 (1991)). Cleavage of these polyproteins by this protease is essential for maturation of the virus, since the proteolytic activity necessary for polyprotein processing cannot be provided by host cellular enzymes. An important finding has been that viruses which lack this protease, or contain a mutation which produces a defective protease, lack infectivity [C. Peng et al., *J. Virol,* 63: 2550–2556 (1989) and N. Kohl et al., *Proc. Nati. Acad. Sci. USA,* 85: 4689–90 (1987)]. Thus, a selective HIV protease inhibitor has been shown to inhibit viral spread and the production of cytopathic effects in cultures of acutely infected cells (J. C. Craig et al., *Antiviral Research,* 16: 295–305 (1991)). For this reason, inhibition of HIV protease is believed to be a viable approach to antiviral therapy.

HIV protease inhibitors have been extensively reviewed (see for example A. Tomasselli et al., *Chimica Oggi,* 9: 6–27 (1991) and T. Meek, *J. Enzyme Inhibition* 6: 65–98 (1992)). However, the majority of these inhibitors are peptides and thus unsuitable as drugs, due to the well known pharmacological deficiencies exhibited by most peptide drugs (biliary excretion, low bioavailability and stability in physiological milieu, etc.) Nonpeptidic inhibitors of HIV protease are thus very important, since these may lead to very useful therapeutic agents.

Hei 3-227923 claimed coumarins with anti-HIV activity. However, only 4-hydroxycoumarin was specifically described without discussing its mechanism of action.

World Patent 89/07939 claimed eight coumarin derivatives as HIV reverse transcriptase inhibitors with potential antiviral activity. These derivatives are hexachlorocoumarin, 7-acetoxycoumarin, and the structures shown below.

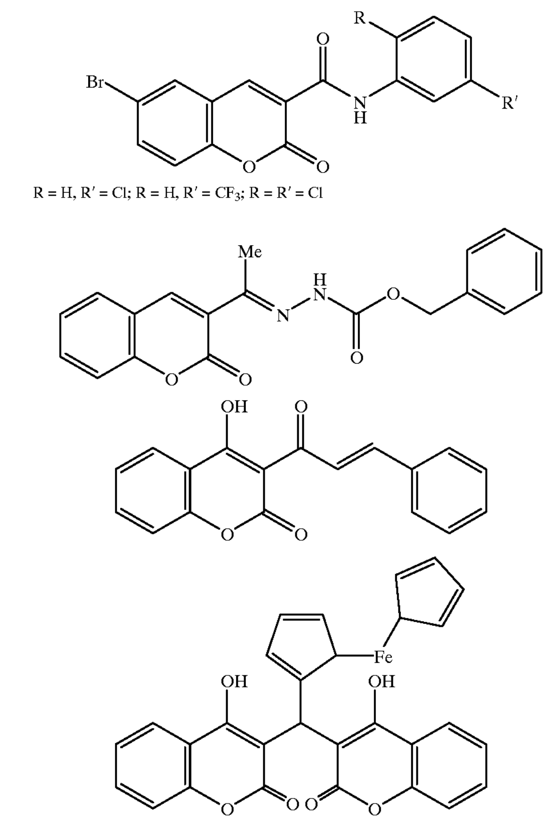

Warfarin (3-(α-acetonylbenzyl)-4-hydroxycoumarin), shown below, was reported by R. Nagorny et al. in *AIDS,* 7: 129–130 (1993) as inhibiting cell-free and cell-mediated HIV infection. However Warfarin was the only pyrone studied and its mechanism of action in HIV inhibition was not specified.

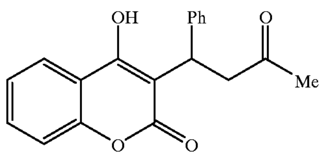

Selected flavones, structurally different from the pyrones of the present invention, were reported by Fairli et al. (*Biochem. Biophys. Res. Comm.,* 188: 631–637 (1992)) to be inhibitors of HIV-1 protease. These compounds are shown below.

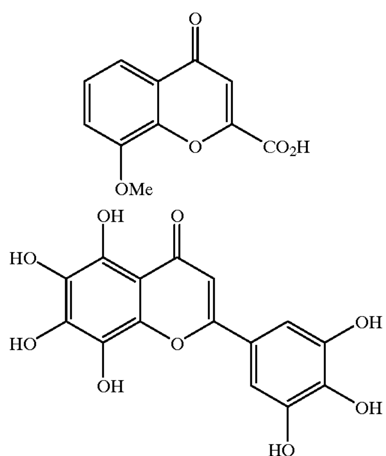

U.S. Pat. No. 3,206,476 describes several pyrones, specifically 3-substituted-4-hydroxy-6-aryl-2-pyrones, as antihypertensive agents. However, the range of substituents at the 3-position of these heterocycles is limited to halo and amino groups and alkanoylamino derivatives.

U.S. Pat. No. 3,818,046 describes several pyrone derivatives, specifically 4-hydroxypyrones with sulfur-containing carbon chains at the 3-position, as growth stunters and antimicrobial agents. The substitution at the 6-position of these heterocycles is limited to the methyl group. The pyrones, which are shown below, are substituted as follows: R=Me; M=H or alkali metal; and R'=H, alkyl, phenyl, halophenyl, nitrophenyl, phenyl substituted with lower alkyl, benzyl, phenethyl, naphthylmethyl, halobenzyl, benzyl substituted with lower alkyl, nitrobenzyl, propargyl, allyl, cyclohexyl substituted with lower alkyl, thioalkyl containing a lower alkyl group, lower alkyl, or adamantyl; and n=0 to 2.

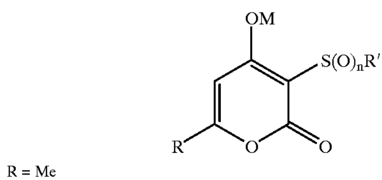

A process for preparing the pyrones shown above is claimed in U.S. Pat. No. 3,931,235.

3. SUMMARY OF THE INVENTION

The present invention is based in great part on the extraordinary discovery of the inventors that novel tri- and tetrasubstituted pyrones and related compounds, selected from a very broad spectrum of tailored molecular structures, potently inhibit the HIV aspartyl protease blocking infection by HIV. The present invention is also based on the insights of the inventors regarding the mechanism of action of antiviral drugs, especially as revealed by their studies on structure-activity relationships characteristic of anti-HIV compounds that include pyrones.

The invented pyrones are expected to be extremely useful in the development of treatments for infections caused by viruses, especially by retroviruses that rely on aspartyl protease activities for replication and infectivity. One such retrovirus is HIV. As virus blockers, the pyrones are also expected to be very useful in the treatment of diseases and syndromes associated with viral pathogens. One such syndrome is AIDS.

Efficient syntheses of the biologically active pyrones, involving either de novo assemblies of the pyrone nucleus or modifications of suitably functionalized pyrones, are disclosed. Furthermore, many working examples outlining the preparation of specific pyrones whose structures contain the desired functional groups in proper geometric arrangements are given.

The testing of specific pyrones as inhibitors of the HIV aspartyl protease, based on a study of the hydrolysis of an undecapeptide enzyme substrate, and the testing of the pyrones as inhibitors of viral growth and infectivity, based on a study of infection of H9 cell lines by the HIV-$1_{iiib}$ strain, are also disclosed. Striking enzyme inhibitions, at nanomolar levels, with corresponding anti-HIV activities, were observed.

The present inventors contemplate the preparation of pharmaceutically useful antiviral compositions comprising one or more of the invented pyrones and related compounds and a pharmaceutically acceptably carrier. They also contemplate the use of these compositions, alone or in combination with other antiviral treatments, in the treatment of infections and diseases caused by retroviruses, including AIDS.

The present invention relates to compounds, or the pharmaceutically acceptable salts thereof, of Formula 1, shown below,

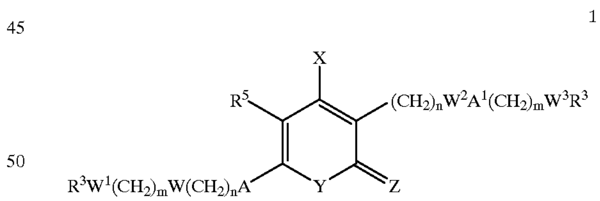

wherein

X is $OR^1$, $NHR^1$, $SR^1$, $CO_2R^4$ or $CH_2OR^1$ wherein $R^1$ is $R^4$ or $COR^4$ wherein $R^4$ is as defined below;

Y is oxygen or sulfur;

Z is oxygen or sulfur;

A and $A^1$ are independently a chemical bond, an unsubstituted or substituted phenyl, naphthyl, a 5- or 6-membered heterocyclic ring, cycloalkyl, or a fused ring system of from 8 to 10 atoms or a substituted derivative thereof wherein the substituents are one or more of F, Cl, Br, $OR^4$, $N(R^4)_2$, $CO_2R^4$, $CON(R^4)_2$, $COR^4$, $R^4$, $OCH_2O$, $OCH_2CH_2O$, or C≡N wherein $R^4$ is independently hydrogen, substituted on unsubstituted alkyl, cycloalkyl, alkylcycloalkyl or phenyl wherein the substituents are one or more of $CO_2R^2$, $CON(R^2)_2$, F, $OR^2$, $SR^2$, $N(R^2)_2$, CN, phenyl, naphthyl, a heterocycle or $CF_3$ wherein $R^2$ is independently alkyl, cycloalkyl, or hydrogen;

$R^5$ is hydrogen, alkyl, cycloalkyl, alkylcycloalkyl, phenyl, or the substituted derivatives thereof wherein the substituents are one or more of $CO_2R^2$, $CON(R^2)_2$, F, $OR^2$, phenyl, naphthyl, $CF_3$, $OR^1$, $NHR^1$, $SR^1$, or $CH_2OR^1$ wherein $R^1$ is as defined above;

$R^3$ is independently hydrogen, $(CH_2)_pR^4$ or $(CH_2)_pA$ wherein p is an integer of from 0 to 2 and $R^4$ and A are as defined above;

W, $W^1$, and $W^3$ are each independently a chemical bond, oxygen, $NR^3$, $C(R^3)_2$, CO, $CR^3{=}CR^3$, C≡C, $CR^3OR^3$, $C(=NR^3)NR^3$, $S(O)_p$, $CR^3N(R^3)_2$, $SO_2NR^3$, $CO_2$ $NR^3COV_gA$ or $NCOV_gR^3$, wherein g is either 0 or 1, and V is oxygen, sulfur, $NR^3$, or $CHR^3$;

$W^2$ is defined in terms of the n of the $(CH_2)_nW^2A^1(CH_2)_mW^3R^3$ group such that if n>0, then $W^2$ is selected from the group consisting of a chemical bond, oxygen, $NR^3$, $C(R^3)_2$, CO, $CR^3{=}CR^3$, C≡C, $CR^3OR^3$, $CR^3N(R^3)_2$, $S(O)_p$, $SO_2NR^3$, $CO_2$, $NR^3COV_gA$ or $NCOV_gR^3$ wherein g is either 0 or 1, and V is oxygen, sulfur, $NR^3$, or $CHR^3$; and if n=0, then $W^2$ is selected from a group consisting of $C(R^3)_2$, CO, $CR^3{=}CR^3$, C≡C, $CR^3OR^3$, $CR^3N(R^3)_2$ and $—CO_2$; and m and n are each independently an integer of from 0 to 4 with the provision that when W and $W^1$ are both heteroatoms or when $W^2$ and $W^3$ are both heteroatoms, m is an integer of from 2 to 4; and with the further proviso that $R^3W^1(CH_2)_mW(CH_2)_nA$ cannot be methyl or ethyl.

Preferred compounds of the instant invention are those of Formula 1 shown above wherein X is hydroxyl, amino, or hydroxymethyl;

Z is oxygen;

Y is oxygen or sulfur;

W, $W^1$, and $W^3$ are each independently oxygen, $NR^3$, $NCOV_gR^3$, $CR^3{=}CR^3$, sulfur, $SO_2NR^3$ or $C(R^3)_2$ and $W^2$ is $CR^3{=}CR^3$ or $C(R^3)_2$ wherein V is oxygen, $NR^3$ or $CHR^3$ wherein $R^3$ is hydrogen, $(CH_2)_pR^4$ or $(CH_2)_pA$ wherein p is an integer of from 0 to 2, g is 0 or 1, and A is independently phenyl, naphthyl, a 5- or 6-membered heterocycle having one or two heteroatoms, a fused ring system of from 8 to 10 atoms, cyclopentyl, cyclohexyl or a substituted derivative thereof wherein the substituents are one or more of F, Cl, Br, $OR^4$, $N(R^4)_2$, $CO_2R^4$, $CON(R^4)_2$, $R^4$, $OCH_2O$, or $OCH_2CH_2O$ wherein $R^4$ is hydrogen, a straight or branched alkyl of from 1 to 5 atoms, a cycloalkyl group of 3 to 6 carbon atoms, a $CH_2$cycloalkyl group of 4 to 8 carbons, phenyl, or a substituted derivative which substituents are of $CO_2R^2$, F, $OR^2$, phenyl, or $CF_3$ wherein $R^2$ is independently hydrogen, methyl, ethyl, isobutyl, t-butyl, or cycloalkyl containing 3 to 6 carbon atoms, wherein $A^1$ is defined as above; and $R^5$ is hydrogen, methyl, ethyl, propyl, cyclopropyl, hydroxyl, carboxyl, or hydroxymethyl.

More preferred compounds of the present invention are those of Formula 1 shown above wherein X is hydroxyl;

Z is oxygen;

Y is oxygen;

W, $W^1$, and $W^3$ are each independently oxygen, sulfur, $SO_2NR^3$, $NR^3$, or $C(R^3)_2$ and $W^2$ is $C(R^3)_2$ wherein $R^3$ is hydrogen, $(CH_2)_pR^4$, or $(CH_2)_pA$ wherein p is an integer of from 0 to 2, $R^4$ is hydrogen, methyl, ethyl, isopropyl, isobutyl, cyclopropyl, cyclohexyl, $CH_2CO_2R^2$, phenyl or benzyl; $R^2$ is H, methyl, ethyl isobutyl or t-butyl; A is phenyl, 2,3- or 4-pyridyl, 2,4- or 5-thiazolyl, morpholinyl, 2 or 3-furyl, cyclopentyl, cyclohexyl, indanyl, or a substituted derivative thereof wherein the substituents are one or more of F, Cl, Br, $OR^4$ $R^4$, $CO_2R^4$ or $OCH_2O$, wherein $A^1$ is defined as above; and $R^5$ is hydrogen, methyl, ethyl, or hydroxymethyl;

Some of the most preferred compounds of the present invention are included in the following:

3-[(Cyclohexylthio)phenylmethyl]-4-hydroxy-6-phenyl-2H-pyran-2-one;

4-Hydroxy-3-[[(2-methoxyphenyl)thio]phenyl-methyl]-6-phenyl-2H-pyran-2-one;

3-(3-Methoxybenzoyl)-6-(3-methoxyphenyl)-2H-pyran-2,4(3H)-dione;

6-[4-[(3,5-Dimethyl-4-isoxazolyl)methoxy]phenyl]-4-hydroxy-3-[(2-phenylethyl)thio]-2H-pyran-2-one;

4-Hydroxy-3-[3-methyl-1-(phenylthio)butyl]-6-phenyl-2H-pyran-2-one;

4-Hydroxy-3-[(2-phenylethyl)thio]-6-[4-(phenylsulfinyl)phenyl]-2H-pyran-2-one;

4-Hydroxy-6-phenyl-3-[phenyl[(phenylmethyl)thio]methyl]-2H-pyran-2-one;

6-(3,5-Dimethylphenyl)-4-hydroxy-3-[(2-phenylethyl)thio]-2H-pyran-2-one;

4-Hydroxy-6-(3-phenoxyphenyl)-3- [(2-phenylethyl)thio]-2H-pyran-2-one;

3-[2-Cyclohexyl-1-(phenylthio)ethyl]-4-hydroxy-6-phenyl-2H-pyran-2-one;

4-Hydroxy-6-[3-methoxy-4-(phenylmethoxy)phenyl]-3-[(2-phenylethyl)thio]-2H-pyran-2-one;

4-Hydroxy-3-[(2-oxo-2-phenylethyl)thio]-6-phenyl-2H-pyran-2-one;

4-Hydroxy-6-phenyl-3-[phenyl(phenylthio)methyl]-2H-pyran-2-one;

3-[Bis(2-naphthalenylmethyl)amino]-4-hydroxy-6-phenyl-2H-pyran-2-one;

4-Hydroxy-6-phenyl-3-[(phenylmethyl)thio]-2H-pyran-2-one;

(S)-1,3-Dihydro-N-(4-hydroxy-2-oxo-6-phenyl-2H-pyran-3-yl)-2-(phenylmethyl)-2H-isoindol-2-acetamide;

N-(1,1-Dimethylethyl)-N'-(4-hydroxy-2-oxo-6-phenyl-2H-pyran-3-yl)-N'-(phenylmethyl) urea;

4-Hydroxy-3-[(2-phenoxyethyl)thio]-6-phenyl-2H-pyran-2-one;

(E)-4-Hydroxy-6-phenyl-3-[(3-phenyl-2-propenyl)thio]-2H-pyran-2-one;

4-Hydroxy-3-phenoxy-6-phenyl-2H-pyran-2-one;

2-Oxo-6-phenyl-3-[(phenylmethyl)thio]-2H-pyran-4-yl-3-methylbutanoic acid ester;

6-(3,4-Dichlorophenyl)-4-hydroxy-3-[(phenylmethyl)thio]-2H-pyran-2-one;

6-(3-Chlorophenyl)-4-hydroxy-3-[(phenylmethyl)thio]-2H-pyran-2-one;

2-Oxo-6-phenyl-3-[(phenylmethyl)thio]-2H-pyran-4-yl propanoic acid, ester;

4-Hydroxy-6-(3-methylphenyl)-3-[(phenylmethyl)thio]-2H-pyran-2-one;

4-Hydroxy-6-(3-hydroxyphenyl)-3-[(phenylmethyl)thio]-2H-pyran-2-one;

4-Hydroxy-6-(2-phenylethyl)-3-[(phenylmethyl)thio]-2H-pyran-2-one;

4-Hydroxy-6-(4-hydroxyphenyl)-3-[(2-phenylethyl)thio]-2H-pyran-2-one;

4-Hydroxy-3-[(2-phenylethyl)thio]-6-[4-(phenylmethoxy)phenyl]-2H-pyran-2-one;

4-Hydroxy-6-[4-(2-phenylethoxy)phenyl]-3-[(2-phenylethyl)thio]-2H-pyran-2-one;

4-Hydroxy-6-[3-(2-phenylethoxy)phenyl]-3-[(2-phenylethyl)thio]-2H-pyran-2-one;

4-Hydroxy-6-(2-hydroxyphenyl)-3-[(phenylmethyl)thio]-2H-pyran-2-one;

4-Hydroxy-6-(3-methoxyphenyl)-3-[(phenylmethyl)thio]-2H-pyran-2-one;

6-(3-Chlorophenyl)-4-hydroxy-3-[(2-phenylethyl)thio]-2H-pyran-2-one;

4-Hydroxy-6-(4-methoxy-3-methylphenyl)-3-[(phenylmethyl)thio]-2H-pyran-2-one;

6-(3-Chloro-4-methoxyphenyl)-4-hydroxy-3-[(phenylmethyl)thio]-2H-pyran-2-one;

4-Hydroxy-3-[(2-phenylethyl)thio]-6-[3-(phenylmethoxy)phenyl]-2H-pyran-2-one;

4-Hydroxy-3-[[2-(4-methoxyphenyl)ethyl]thio]-6-phenyl-2H-pyran-2-one;

3-[(Cyclohexylmethyl)thio]-4-hydroxy-6-phenyl-2H-pyran-2-one;

4-Hydroxy-3-[(phenylmethyl)thio]-6-[3-(trifluoromethyl)phenyl]-2H-pyran-2-one;

4-Hydroxy-3-[(2-phenylethyl)thio]-6-[3-(trifluoromethyl)phenyl]-2H-pyran-2-one;

6-(2,3-Dihydro-1,4-benzodioxin-6-yl)-4-hydroxy-3-[(phenylmethyl)thio]-2H-pyran-2-one;

4-Hydroxy-3-[(2-phenylethyl)thio]-6-[3-methyl-4-(3-pyridinylmethoxy)phenyl]-2H-pyran-2-one;

[4-[4-Hydroxy-2-oxo-3-[(2-phenylethyl)thio]-2H-pyran-6-yl]phenoxy)acetic acid;

[4-[4-Hydroxy-2-oxo-3-[(2-phenylethyl)thio]-2H-pyran-6-yl]phenoxy]acetic acid, ethyl ester;

4-Hydroxy-6-(4-phenoxyphenyl)-3-[(2-phenylethyl)thio]-2H-pyran-2-one;

4-Hydroxy-3-[(2-phenylethyl)thio]-6-[4-(2-pyridinylmethoxy)phenyl]-2H-pyran-2-one;

4-Hydroxy-3-[(2-phenylethyl)thio]-6-[4-(3-pyridinylmethoxy)phenyl]-2H-pyran-2-one;

4-Hydroxy-6-[4-(2-methoxyphenyl)methoxy]phenyl]-3-[(2-phenylethyl)thio]-2H-pyran-2-one;

4-Hydroxy-3-[2-naphthalenyl(phenylthio)methyl]-6-phenyl-2H-pyran-2-one;

4-Hydroxy-3-[(2-naphthalenylthio)phenylmethyl]-6-phenyl-2H-pyran-2-one;

4-Hydroxy-3-[(2-phenylethyl)thio]-6-[4-(phenylthio)phenyl]-2H-pyran-2-one;

6-(1,3-Benzodioxol-5-yl)-4-hydroxy-3-[(phenylmethyl)thio]-2H-pyran-2-one;

6-(3,5-Dimethylphenyl)-4-hydroxy-3-[(phenylmethyl)thio]-2H-pyran-2-one;

4-Hydroxy-6-(2-naphthalenyl)-3-[(phenylmethyl)thio]-2H-pyran-2-one;

4-Hydroxy-6-(4-hydroxyphenyl)-3-[(phenylmethyl)thio]-2H-pyran-2-one;

6-(2-Chlorophenyl)-4-hydroxy-3-[(phenylmethyl)thio]-2H-pyran-2-one;

4-Hydroxy-6-[2-(3-methylbutyl)phenyl]-3-[(phenylmethyl)thio]-2H-pyran-2-one;

6-(3,5-Dimethylphenyl)-4-(hydroxymethyl)-3-[(phenylmethyl)thio]-2H-pyran-2-one;

[4-[4-Hydroxy-5-(hydroxymethyl)-2-oxo-3-[(2-phenylethyl)thio]-2H-pyran-6-yl]phenoxy]acetic acid;

6-(3,5-Dimethylphenyl)-4-hydroxy-5-methyl-3-[2-phenyl-1-[(phenylmethyl)thio]ethyl]-2H-pyran-2-one;

4-Hydroxy-6-[4-(2-methoxyphenoxy)phenyl]-3-[phenyl[(phenylmethyl)thio]methyl]-2H-pyran-2-one;

[4-[3-[2-Cyclopentyl-1-(phenylmethoxy)ethyl]-4-hydroxy-2-oxo-2H-pyran-6-yl]phenoxy]acetic acid;

4-Hydroxy-6-[4-[(1-methylethoxy)methyl]-2-thiazolyl]-2-oxo-3-[2-phenyl-1-[[(phenylmethyl)thio]ethyl]-2H-pyran-2-one;

4-[4-Hydroxy-3-[1-(1-hydroxy-2-phenylethyl)-3-methylpentyl]-2-oxo-2H-pyran-6-yl]benzenepropanoic acid;

6-(3,5-Dimethylphenyl)-4-hydroxy-3-[1-hydroxy-2-methyl-1-(phenylmethyl)propyl]-2H-pyran-2-one;

6-[3-Fluoro-4-(3-pyridinylmethoxy)phenyl]-4-hydroxy-3-[3-methyl-1-[(phenylmethyl)thio]butyl]-2H-pyran-2-one;

[2-(Hydroxymethyl)-4-[4-hydroxy-3-[1-(1-methylethoxy)-2-(phenylthio)ethyl]-2-oxo-2H-pyran-6-yl]phenoxy]acetic acid;

[4-[4-Hydroxy-3-[3-methyl-2-(phenylthio)butyl]-2-oxo-2H-thiopyran-6-yl]phenoxy]acetic acid;

4-Hydroxy-6-[(4-methoxyphenyl)methyl]-3-[[1-(phenylmethyl)butyl]thio]-2H-pyran-2-one;

[2-Hydroxy-4-[4-hydroxy-2-oxo-3-[2-(phenylmethylene)pentyl]-2H-pyran-6-yl]phenoxy]acetic acid;

[[5-[2-Oxo-4-hydroxy-3-[(3-methyl-1-phenylbutyl)thio]-2H-pyran-6-yl]-2-pyridinyl]oxy]acetic acid;

4-Hydroxy-6-[5-(phenoxymethyl)-2-furanyl]-3-[2-phenyl-1-[(phenylmethyl)thio]ethyl]-2H-pyran-2-one;

[4-[4-Hydroxy-2-oxo-3-[2-phenyl-1-[(phenyl-methyl)amino]ethyl]-2H-pyran-6-yl]phenoxy]acetic acid;

4-Hydroxy-3-[2-phenyl-1-[phenyl(phenyl-methyl)amino]ethyl]-6-[4-(3-pyridinylmethoxy)phenyl]-2H-pyran-2-one;

[[4-[4-Hydroxy-2-oxo-3-[(phenylmethyl)thio]-2H-pyran-6-yl]cyclohexyl]oxy]acetic acid;

Cis-6-(3,5-Dimethylphenyl)-4-hydroxy-3-[3-methyl-1-[1,3-dihydro-1-hydroxy-2H-inden-2-yl)thio]butyl]-2H-pyran-2-one;

4-Hydroxy-3-[(2-isopropylphenyl)thio]-6-phenyl-2H-pyran-2-one;

4-Hydroxy-3-[[(2-methylpropyl)phenyl]thio]-6-phenyl-2H-pyran-2-one;

3-[(2-Cyclopropylmethyl)phenyl)thio]-4-hydroxy-6-phenyl-2H-pyran-2-one;

4-Hydroxy-3-[(2-isopropylphenyl)thio]-6-(2,3-dihydro-1,4-benzidioxin-6-yl)-2H-pyran-2-one;

3-[(2,5-Diisopropylphenyl)thio]-4-hydroxy-6-[(3-phenyl)phenyl]-2H-pyran-2-one;

6-[4-(3-Furanylmethoxy)phenyl]-4-hydroxy-3-[3-methyl-1-[(phenylmethyl)thio]butyl]-2H-pyran-2-one;

6-[4-(Cyclohexylmethoxy)phenyl]-4-hydroxy-3-[(2-phenylethyl)thio]-2H-pyran-2-one;

4-Hydroxy-3-[(2-phenylethyl)thio]-6-[4-(phenylsulfonyl)phenyl]-2H-pyran-2-one;

4-Hydroxy-3-[(2-phenylethyl)thio]-6-[4-benzoyloxy)phenyl]-2H-pyran-2-one;

4-Hydroxy-3-[(2-phenylethyl)thio]-6-[4-(phenylsulfinyl)phenyl]-2H-pyran-2-one;

4-Hydroxy-3-[(2-phenylethyl)thio]-6-(4-pyridinyl)-2H-pyran-2-one;

3-[1,4-Bis(phenylthio)butyl]-4-hydroxy-6-phenyl-2H-pyran-2-one;

4-Hydroxy-6-phenyl-3-[phenyl[(phenylmethyl)thio]methyl]-2H-pyran-2-one;

4-Hydroxy-3-[[(2-methoxyphenyl)thio]phenylmethyl]-6-phenyl-2H-pyran-2-one;

4-Hydroxy-3-[3-methyl-1-(phenylthio)butyl]-6-phenyl-2H-pyran-2-one;

3-[2-Cyclohexyl-1-(phenylthio)ethyl]-4-hydroxy-6-phenyl-2H-pyran-2-one;

4-Hydroxy-6-(3-phenoxyphenyl)-3-[(2-phenylethyl)thio]-2H-pyran-2-one;

4-Hydroxy-6-[3-methoxy-4-(phenylmethoxy)phenyl]-3-[(2-phenylethyl)thio]-2H-pyran-2-one;

6-(3,5-Dimethylphenyl)-4-hydroxy-3-[(2-phenylethyl)thio]-2H-pyran-2-one;

4-Hydroxy-3-[[(3-methoxyphenyl)methyl]thio]-6-phenyl-2H-pyran-2-one;

4-Hydroxy-3-[4-methyl-1-(phenylthio)pentyl]-6-phenyl-2H-pyran-2-one;

4-Hydroxy-6-phenyl-3-[[[3-(phenylmethoxy)phenyl]methyl]thio]-2H-pyran-2-one;

3-[(1,3-Benzodioxol-5-ylmethyl)thio]-4-hydroxy-6-phenyl-2H-pyran-2-one;

4-Hydroxy-3-[[(2-methoxyphenyl)methyl]thio]-6-phenyl-2H-pyran-2-one;

4-Hydroxy-3-[[(2-methylphenyl)methyl]thio]-6-phenyl-2H-pyran -2-one;

4-Hydroxy-3-[[(3-methylphenyl)methyl]thio]-6-phenyl-2H-pyran-2-one;

4-Hydroxy-3-[[(4-methylphenyl)methyl]thio]-6-phenyl-2H-pyran-2-one;

6-[1,1'-Biphenyl]-3-yl-4-hydroxy-3-[(2-phenylethyl)thio]-2H-pyran-2-one;

4-Hydroxy-3-[[(4-methoxyphenyl)methyl]thio]-6-phenyl-2H-pyran-2-one;

3-[2-Cyclohexyl-1-(cyclohexylthio)ethyl]-4-hydroxy-6-phenyl-2H-pyran-2-one;

3-[1-[(2,6-Dimethylphenyl)thio]-3-methylbutyl]-4-hydroxy-6-phenyl-2H-pyran-2-one;

3-[1-(Cyclohexylthio)-2-cyclopropylethyl]-4-hydroxy-6-phenyl-2H-pyran-2-one;

3-[1-[(2,6-Dichlorophenyl)thio]-3-methylbutyl]-4-hydroxy-6-phenyl-2H-pyran-2-one;

3-[1-Cyclohexylthio)-3,3-dimethylbutyl)-4-hydroxy-6-phenyl-2H-pyran-2-one;

[4-[4-Hydroxy-2-oxo-3-[(2-phenylethyl)thio]-2H-pyran-6-yl]-2-methylphenoxy), acetic acid, ethyl ester;

6-[3,5-Dimethyl-4-[[dimethyl(1,1-dimethylethyl)silyl]oxy]phenyl]-4-hydroxy-3-[(phenylmethyl)thio]-2H-pyran-2-one;

4-Hydroxy-3-[(2-phenylethyl)thio]-6-[4-(4-pyridinylmethoxy)phenyl]-2H-pyran-2-one;

3-[1-(Cyclopentylthio)-3-methylbutyl]-4-hydroxy-6-phenyl-2H-pyran-2-one;

[4-[4-Hydroxy-2-oxo-3[(2-phenylethyl)thio]-2H-pyran-6-yl]-2-methylphenoxy acetic acid;

3-[l-(Cyclohexylthio)-2-(cyclopentyl)ethyl]-4-hydroxy-6-phenyl-2H-pyran-2-one;

4-Hydroxy-6-(4-hydroxy-3,5-dimethylphenyl)-3-[(phenylmethyl)thio]-2H-pyran-2-one;

4-Hydroxy-6-phenyl-3-[[[3-(2-phenylethoxy)phenyl)methyl]thio]-2H-pyran-2-one;

4-Hydroxy-6-[4-(2-phenylethynyl)phenyl]-3-[(2-phenylethyl)thio]-2H-pyran-2-one;

4-Hydroxy-6-[4-(2-phenylethyl)phenyl]-3-[(2-phenylethyl)thio]-2H-pyran-2-one;

3-[(Cyclohexylthio)phenylmethyl]-4-hydroxy-6-phenyl-2H-pyran-2-one;

4-Hydroxy-3-[(phenylmethyl)thio]-6- [3-(trifluoromethoxy)phenyl]-2H-pyran-2-one;

3-[ (Cyclohexylmethyl)thio]-4-hydroxy-6-phenyl-2H-pyran-2-one;

4-Hydroxy-3-[(2-phenylethyl)thio]-6-[3-methyl-4-(3-pyridinylmethoxy)phenyl]-2H-pyran-2-one;

6-(2,3-Dihydro-1,4-benzodioxin-6-yl)-4-hydroxy-3-[(phenylmethyl)thio]-2H-pyran-2-one;

4-Hydroxy-3-[(2-phenylethyl)thio]-6-(3-(trifluoromethyl)phenyl]-2H-pyran-2-one;

4-Hydroxy-3-[(phenylmethyl)thio]-6-[3-(trifluoromethyl)phenyl]-2H-pyran-2-one;

4-Hydroxy-3-[(phenylmethyl)thio]-6-(2,3,4-trimethoxyphenyl)-2H-pyran-2-one;

N-[4-[4-Hydroxy-2-oxo-3-[(2-phenylethyl)thio]-2H-pyran-6-yl]phenyl]benzenesulfonamide;

6-[4-[(3,5-Dimethyl-4-isoxazolyl)methoxy]phenyl]-4-hydroxy-3-[(2-phenylethyl)thio]-2H-pyran-2-one;

3-[(Cyclohexylthio)phenylmethyl]-4-hydroxy-6-[3-methyl-4-(3-pyridinylmethoxy)phenyl]-2H-pyran-2-one;

2-[[(4-Hydroxy-2-oxo-6-phenyl-2H-pyran-3-yl)thio]methyl]-benzoic acid methyl ester;

3-[1-(Cyclohexylthio)-3-methylbutyl]-6-(2,3-dihydro-1,4-benzodioxin-6-yl)4-hydroxy-2H-pyran-2-one;

2-[[4-(4-Hydroxy-2-oxo-3-[(2-phenylethyl)thio]-2H-pyran-6-yl]phenoxy]methyl-benzoic acid methyl ester;

4-Hydroxy-3-[(2-phenylethyl)thio]-6-[4-(1H-tetrazol-5-ylmethoxy)phenyl]-2H-pyran-2-one;

4-Hydroxy-6-[3-methyl-4-(2-pyridinylmethoxy)phenyl]-3-[(2-phenylethyl)thio]-2H-pyran-2-one;

3-[2-Cyclopropyl-1-[(phenylmethyl)thio]ethyl]-4-hydroxy-6-phenyl-2H-pyran-2-one;

4-Hydroxy-3-[l-[(2-methoxyphenyl)thio]-3-methylbutyl]-6-phenyl-2H-pyran-2-one;

4-Hydroxy-3-[1-[(phenylmethyl)thio]-3-methylbutyl]-6-phenyl-2H-pyran-2-one;

4-[[4-Hydroxy-2-oxo-3-[(2-phenylethyl)thio]-2H-pyran-6-yl]phenoxy]methyl]benzoic acid methyl ester;

3-[[4-[4-Hydroxy-2-oxo-3-[(2-phenylethyl)thio]-2H-pyran-6-yl]phenoxy]miethyl]benzoic acid methyl ester;

6-[4-[(3,4-Dichlorophenyl)methoxy]phenyl]-4-hydroxy-3-[(2-phenylethyl)thio]-2H-pyran-2-one;

3-[[(4-Hydroxy-2-oxo-6-phenyl-2H-pyran-3-yl)thio]methyl]benzoic acid methyl ester;

4-[[(4-Hydroxy-2-oxo-6-phenyl-2H-pyran-3-yl)thio]methyl]benzoic acid methyl ester;

6-[3,5-Bis(trifluoroinethyl)phenyl]-4-hydroxy-3-[(phenylmethyl)thio]-2H-pyran-2-one;

3-[1-(Cyclohexylthio)-3-methylbutyl]-4-hydroxy-6-phenyl-2H-pyran-2-one;

[4-[4-Hydroxy-2-oxo-3-[(2-phenylethyl)thio]-2H-pyran-6-yl]phenoxy]acetonitrile;

6-Phenyl-4-hydroxy-3-[(cyclopropylmethyl)thio]-2H-pyran-2-one;

6-(3-Chlorophenyl)-4-hydroxy-3-[(4-phenylbutyl)thio]-2H-pyran-2-one;

4-Hydroxy-3-[(2-hydroxy-2-phenylethyl)thio]-6-phenyl-2H-pyran-2-one;

6-Phenyl-4-hydroxy-5-methyl-3-(phenylthio)-2H-pyran-2-one;

[4-[4-Hydroxy-2-oxo-3-(phenylthio)-2H-pyran-6-yl]phenoxy]acetic acid;

[4-[4-Hydroxy-5-methyl-2-oxo-3-(phenylthio)-2H-pyran-6-yl]phenoxy]acetic acid;

4-Hydroxy-3-[(phenylmethyl)thio]-6-(3-pyridinyl)-2H-pyran-2-one;

6-(2,6-Dimethyl-4-pyridinyl)-4-hydroxy-3-[(phenylmethyl)thio]-2H-pyran-2-one;

4-Hydroxy-3-[(phenylmethyl)thio]-6-(3-thienyl)-2H-pyran-2-one;

4-Hydroxy-3-[(2-isopropylphenyl)thio]-6-[1-(2-methylpropyl)cyclopentyl]-2H-pyran-2-one;

4-Hydroxy-3-[(2-isopropylphenyl)thio]-6-[1-(3-methylbutyl)cyclopentyl]-2H-pyran-2-one;

4-Hydroxy-3-[(2-isopropylphenyl)thio]-6-[1-(4-methylpentyl)cyclopentyl]-2H-pyran-2-one;

4-Hydroxy-3-[(2-isopropylphenyl)thio]-6-[1-(phenylmethyl)cyclopentyl]-2H-pyran-2-one;

4-Hydroxy-3-[(2-isopropylphenyl)thio]-6-[1-(2-phenylethyl)cyclopentyl]-2H-pyran-2-one;

4-Hydroxy-3-[(2-isopropylphenyl)thio]-6-[1-(3-phenylpropyl)cyclopentyl]-2H-pyran-2-one;

4-Hydroxy-3-[(2-isopropylphenyl)thio]-6-[1-(2-methylpropyl)cyclopropyl]-2H-pyran-2-one;

4-Hydroxy-3-[(2-isopropylphenyl)thio]-6-[1-(3-methylbutyl)cyclopropyl]-2H-pyran-2-one;

4-Hydroxy-3-[(2-isopropylphenyl)thio]-6-[1-(4-methylpentyl)cyclopropyl]-2H-pyran-2-one;

4-Hydroxy-3-[(2-isopropylphenyl)thio]-6-[1-(phenylmethyl)cyclopropyl]-2H-pyran-2-one;

4-Hydroxy-3-[(2-isopropylphenyl)thio]-6-[1-(2-phenylethyl)cyclopropyl]-2H-pyran-2-one;

4-Hydroxy-3-[(2-isopropylphenyl)thio]-6-[1-(3-phenylpropyl)cyclopropyl]-2H-pyran-2-one;

4-Hydroxy-6-(3-hydroxyphenyl)-3-[(2-isopropylphenyl)thio]-2H-pyran-2-one;

4-Hydroxy-3-[(2-isopropylphenyl]thio]-6-(pyridin-4-yl)-2H-pyran-2-one;

4-Hydroxy-3-[(2-isopropylphenyl)thio]-6-(pyridin-2-yl)-2H-pyran-2-one;

4-Hydroxy-3-[(2-isopropylphenyl)thio]-6-(4-nitrophenyl)-2H-pyran-2-one;

6-(4-Fluorophenyl)-4-hydroxy-3-[(2-isopropylphenyl)thio]-2H-pyran-2-one;

4-Hydroxy-3-[(2-isopropylphenyl)thio]-6-(2-methylphenyl)-2H-pyran-2-one;

4-Hydroxy-3-[(2-isopropylphenyl)thio]-6-(2-methoxyphenyl)-2H-pyran-2-one;

6-(2-Chlorophenyl)-4-hydroxy-3-[(2-isopropylphenyl)thio]-2H-pyran-2-one;

4-Hydroxy-3-[(2-isopropylphenyl)thio]-6-[4-(N,N-dimethylamino)phenyl]-2H-pyran-2-one;

4-Hydroxy-3-[(2-isopropylphenyl)thio]-6-(3-trifluoromethylphenyl)-2H-pyran-2-one;

4-Hydroxy-3-[(2-isopropylphenyl)thio]-6-[4-(1-naphthalenylmethyloxy)phenyl]-2H-pyran-2-one;

4-Hydroxy-3-[(2-isopropylphenyl)thio]-6-[4-[2-(morpholin-4-yl)ethoxy)phenyl]-2H-pyran-2-one;

4-Hydroxy-3-[(2-isopropylphenyl)thio]-6-[3-[2-(morpholin-4-yl)ethoxy)phenyl]-2H-pyran-2-one;

6-(4-Benzyloxy-3-methoxyphenyl)-4-hydroxy-3-[(2-isopropylphenyl)thio]-2H-pyran-2-one;

6-(4-Benzyloxy-3-chlorophenyl)-4-hydroxy-3-[(2-isopropylphenyl)thio]-2H-pyran-2-one;

4-[4-Hydroxy-2-oxo-3-[(2-isopropylphenyl)thio]-2H-pyran-6-yl]-2-methylphenoxy-acetic acid;

4-Hydroxy-6-[4-(2-hydroxyethoxy) phenyl]-3-[(2-isopropylphenyl)thio]-2H-pyran-2-one;

2-[3-[4-Hydroxy-5-[(2-isopropylphenyl)thio]-6-oxo-6H-pyran-2-yl]phenoxy]acetamide;

4-Hydroxy-3-[(2-isopropylphenyl)thio]-6-[4-(2,3-pyrazinemethoxy)phenyl]-2H-pyran-2-one;

4-Hydroxy-3-[(2-isopropylphenyl)thio]-6-[4-(pyridin-3-ylmethoxy)phenyl]-2H-pyran-2-one;

4-Hydroxy-3-[(2-isopropylphenyl)thio]-6-[4-(pyridin-2-ylmethoxy)-3-methylphenyl]-2H-pyran-2-one;

4-Hydroxy-3-[(2-isopropylphenyl)thio]-6-[4-(pyridin-4-ylmethoxy)phenyl]-2H-pyran-2-one;

3-[(2-Cyclopropylphenyl)thio]-4-hydroxy-6-[4-(pyridin-3-ylmethoxy)phenyl]-2H-pyran-2-one;

4-Hydroxy-3-[(2,5-diisopropylphenyl)thio]-6-[4-(pyridin-3-ylmethoxy)phenyl]-2H-pyran-2-one;

4-Hydroxy-3-[(2-isopropylphenyl)thio]-6-[4-[2-(thiomorpholin-4-yl)ethoxy]phenyl]-2H-pyran-2-one;

4-Hydroxy-3-[(2-isopropylphenyl)thio]-6-[4-[2-(piperazin-1-yl)ethoxy]phenyl]-2H-pyran-2-one;

4-Hydroxy-3-[(2-isopropylphenyl)thio]-6-[4-[2-(methylpiperazin-1-yl)ethoxy]phenyl]-2H-pyran-2-one;

4-Hydroxy-3-[(2-isopropylphenyl)thio]-6-[4-[2-(1,1-dioxothiomorpholin-4-yl)ethoxy]phenyl]-2H-pyran-2-one;

4-Hydroxy-3-[(2-isopropylphenyl)thio]-6-(1-phenyl-cyclopentyl)-2H-pyran-2-one;

4-Hydroxy-3-[(2-isopropylphenyl)thio]-6-(4-phenyl-piperidin-4-yl)-2H-pyran-2-one;

Isopentanoic acid 2-oxo-6-phenyl-3-[(2-isopropylphenyl)thio]-2H-pyran-2-one-4-ylester;

Propanoic acid 2-oxo-6-phenyl-3-[(2-isopropylphenyl)thio]-2H-pyran-2-one-4-ylester;

Phenylacetic acid 2-oxo-6-phenyl-3-[(2-isopropylphenyl)thio]-2H-pyran-2-one-4-ylester;

4-Hydroxy-3-[(2-isopropyl-5-methylphenyl)thio]-6-phenyl-2H-pyran-2-one;

4-Hydroxy-3-[(2-isopropyl-4-methylphenyl)thio]-6-phenyl-2H-pyran-2-one;

4-Hydroxy-3-[(2-isopropyl-6-methylphenyl)thio]-6-phenyl-2H-pyran-2-one;

3-[(4-Chloro-2-isopropylphenyl)thio]-4-hydroxy-6-phenyl-2H-pyran-2-one;

4-Hydroxy-3-[(4-hydroxy-2-isopropylphenyl)thio]-6-phenyl-2H-pyran-2-one;

3-[(2-Cyclopropylphenyl)thio]-4-hydroxy-6-phenyl-2H-pyran-2-one;

3-[(2,5-Diisopropylphenyl)thio]-4-hydroxy-6-phenyl-2H-pyran-2-one;

4-Hydroxy-6-phenyl-3-[(2-tert-butylphenyl)thio]-2H-pyran-2-one;

3-[(2-Cyclopropyl-5-isopropylphenyl)thio]-4-hydroxy-6-phenyl-2H-pyran-2-one;

3-[(2-Cyclopentyl-5-isopropylphenyl)thio]-4-hydroxy-6-phenyl-2H-pyran-2-one;

3-[(2-Cyclohexyl-5-isopropylphenyl)thio]-4-hydroxy-6-phenyl-2H-pyran-2-one;

4-Hydroxy-6-phenyl-3-[(2-tert-butyl-5-isopropylphenyl)thio]-2H-pyran-2-one;

3-[(2,5-Di-tert-butylphenyl)thio]-4-hydroxy-6-phenyl-2H-pyran-2-one;

3-[(2-Cyclopentylphenyl)thio]-4-hydroxy-6-phenyl-2H-pyran-2-one;

3-[(2-Cyclohexylphenyl)thio]-4-hydroxy-6-phenyl-2H-pyran-2-one;

4-[[4-Hydroxy-2-oxo-6-phenyl-2H-pyran-3-yl]thio]-2-hydroxyindane;

4-Hydroxy-3-[[2-isopropyl-4-(morpholin-4-ylmethyl)phenyl]thio]-6-phenyl-2H-pyran-2-one;

4-Hydroxy-3-[(6-isopropyl-indan-5-yl)thio]-6-phenyl-2H-pyran-2-one;

4-Hydroxy-3-[(4-isopropyl-benzo[1,3]dioxol-5-yl)thio]-6-phenyl-2H-pyran-2-one;

3-[(2-tert-Butyl-4-thiomorpholin-4-ylmethylphenyl)thio]-4-hydroxy-6-phenyl-2H-pyran-2-one;

4-Hydroxy-6-[4-(pyridin-3-ylmethoxy)phenyl]-3-[(2-tert-butylphenyl)thio]-2H-pyran-2-one;

3-[[(2-Cyclopropyl-5-isopropyl)phenyl]thio]-4-hydroxy-6-[4-(pyridin-3-ylmethoxy)phenyl]-2H-pyran-2-one;

3-[[(2-Cyclopentyl-5-isopropyl)phenyl]thio]-4-hydroxy-6-[4-(pyridin-3-ylmethoxy)phenyl]-2H-pyran-2-one;

3-[[(2-Cyclohexyl-5-isopropyl)phenyl]thio)-4-hydroxy-6-[4-(pyridin-3-ylmethoxy)phenyl]-2H-pyran-2-one;

4-Hydroxy-6-[4-(pyridin-3-ylmethoxy)phenyl]-3-[(2-tert-butyl-5-isopropylphenyl)thio]-2H-pyran-2-one;

3-[(2,5-Di-tert-butylphenyl)thio]-4-hydroxy-6-[4-(pyridin-3-ylmethoxy)phenyl]-2H-pyran-2-one;

3-[(2-Cyclopentylphenyl)thiol-4-hydroxy-6-[4-(pyridin-3-ylmethoxy)phenyl]-2H-pyran-2-one;

3-[(2-Cyclohexylphenyl)thio]-4-hydroxy-6-[4-(pyridin-3-ylmethoxy)phenyl]-2H-pyran-2-one;

4-Hydroxy-6-[4-(pyridin-3-ylmethoxy)phenyl]-3-[(6-tert-butylindan-5-yl)thio]-2H-pyran-2-one;

4-Hydroxy-3-[(2-isopropyl-4-morpholin-4-ylmethyl-phenyl)thio]-6-[4-(pyrindin-3-ylmethoxy)phenyl]-2H-pyran-2-one;

Acetic acid 3-[(2-isopropylphenyl)thio]-2-oxo-6-[4-(pyridin-3-ylmethoxy)phenyl]-2H-pyran-4-ylester;

Isobutyric acid 3-[(2-isopropylphenyl)thio]-2-oxo-6-[4-(pyridin-3-ylmethoxy)phenyl]-2H-pyran-4-ylester;

2,2-Dimethylpropionic acid 3-[(2-isopropylphenyl)thio]-2-oxo-6-[4-(pyridin-3-ylmethoxy)phenyl]-2H-pyran-4-ylester;

4-Hydroxy-3-[(2-isopropylphenyl)sulfonyl]-6-[4-(pyridin-3-ylmethoxy)phenyl]-2H-pyran-2-one;

4-Hydroxy-3-(2-isopropylbenzoyl)-6-[4-(pyridin-3-ylmethoxy)phenyl]-2H-pyran-2-one;

3-[(2-tert-Butylphenyl)sulfonyl]-4-hydroxy-6-phenyl-2H-pyran-2-one;

6-(1-Benzylpropyl)-4-hydroxy-3-[(2-isopropylphenyl)sulfonyl]-2H-pyran-2-one;

6-(1-Benzylpropyl)-4-hydroxy-3-[(2-isopropylphenyl)thio]-2H-pyran-2-one;

6-(1-Benzylpropyl)-3-[(2-tert-butylphenyl)thio]-4-hydroxy-2H-pyran-2-one;

N-[3-[[6-(1-Benzylpropyl)-4-hydroxy-2-oxo-2H-pyran-3-yl]thio]-2-isopropylphenyl]benzenesulfonamide;

6-[1-Cyclopropylmethyl-2-(tetrahydro-pyran-3-yl)ethyl]-4-hydroxy-3-[(2-isopropylphenyl)thio]-2H-pyran-2-one;

4-Hydroxy-3-(2-isopropyl-phenoxy)-6-[4-(pyridin-3-ylmethoxy)phenyl]-2H-pyran-2-one;

4-Hydroxy-3-(2-isopropyl-phenoxy)-6-phenyl-2H-pyran-2-one;

3-(2-tert-Butyl-phenoxy)-4-hydroxy-6-[4-(pyridin-3-ylmethoxy)phenyl]-2H-pyran-2-one;

3-(2-tert-Butyl-5-methyl-phenoxy)-4-hydroxy-6-[4-(pyridin-3-ylmethoxy)phenyl]-2H-pyran-2-one;

6-(1-Benzylpropyl)-4-hydroxy-3-(2-isopropylphenoxy)-2H-pyran-2-one;

6-(1-Benzylpropyl)-3-(2-tert-butylphenoxy)-4-hydroxy-2H-pyran-2-one;

3-Benzyloxy-4-hydroxy-6-[4-(pyridin-3-ylmethoxy)phenyl]-2H-pyran-2-one;

2-[4-Hydroxy-2-oxo-6-[4-(pyridin-3-ylmethoxy)phenyl]-2H-pyran-3-yloxymethyl]benzoic acid methyl ester;

2-[[[6-(1-Benzylpropyl)-4-hydroxy-2-oxo-2H-pyran-3-yl]oxy]methyl]benzoic acid ethyl ester;

6-(1-Benzylpropyl)-4-hydroxy-3-(1-phenylbutoxy)-2H-pyran-2-one;

6-(1-Benzylpropyl)-3-(cyclopropylphenylamino)-4-hydroxy-2H-pyran-2-one;

N-[3-[[6-(1-Benzylpropyl)-4-hydroxy-2-oxo-2H-pyran-3-yl]cyclopropylamino]phenyl]benzenesulfonamide;

3-[Cyclopropylphenylamino]-4-hydroxy-6-(pyridin-3-ylmethoxy)-2H-pyran-2-one;

3-(Bis-cyclopentylmethyl-amino)-4-hydroxy-6-(pyridin-3-ylmethoxy)-2H-pyran-2-one;

3-[Cyclopentylmethyl(cyclopropylmethyl)amino]-4-hydroxy-6-(pyridin-3-ylmethoxy)-2H-pyran-2-one;

6-[1-Cyclopropylmethyl-2-(tetrahydro-pyran-3-yl)ethyl]-3-(cyclopropylphenylamino)-4-hydroxy-2H-pyran-2-one;

Cyclopropanecarboxylic acid cyclopentylmethyl-[4-hydroxy-2-oxo-6-[(pyridin-3-ylmethoxy)phenyl]-2H-pyran-3-yl]amide;

Cyclopentanecarboxylic acid cyclopentylmethyl-[4-hydroxy-2-oxo-6-[4-(pyridin-3-ylmethoxy)phenyl]-2H-pyran-3-yl]amide;

N-Cyclopentylmethyl-N-[4-hydroxy-2-oxo-6-[4-(pyridin-3-ylmethoxy)phenyl]-2H-pyran-3-yl]cyclopentanesulfonamide;

3-(Cyclopropylphenylmethyl)-4-hydroxy-6-[4-(pyridin-3-ylmethoxy)phenyl]-2H-pyran-2-one;

N-[3-[Cyclopropyl[4-hydroxy-2-oxo-6-[4-(pyridin-3-ylmethoxy)phenyl]-2H-pyran-3-yl]methyl]phenyl]benzenesulfonamide;

4-Hydroxy-3-(1-phenylpropyl)-6-[4-(pyridin-3-ylmethoxy)phenyl)]-2H-pyran-2-one;

6-(1,1-Dimethyl-3-phenylpropyl)-4-hydroxy-3-[(2-isopropylphenyl)thio]-2H-pyran-2-one;

N-[3-[Cyclopropyl[6-(1,1-dimethyl-3-phenylpropyl)-4-hydroxy-2-oxo-2H-pyran-3-yl]methyl]phenyl]benzenesulfonamide;

N-[3-[Cyclopropyl[4-hydroxy-2-oxo-6-[1-(2-phenylethyl)cyclopentyl]-2H-pyran-3-yl]methyl]phenyl]-benzenesulfonamide;

3-(Cyclopropylphenylmethyl)-6-(1,1-dimethyl-3-phenylpropyl)-4-hydroxy-2H-pyran-2-one;

N-[3-[[6-(1-Benzylcyclopropyl)-4-hydroxy-2-oxo-2H-pyran-3-yl]cyclopropylmethyl]phenyl]-benzenesulfonamide;

6-(1-Benzylpropyl)-4-hydroxy-3-(2-isobutyl-5-isopropylphenyl)-2H-pyran-2-one;

6-(1-Benzylpropyl)-4-hydroxy-3-(2-methyl-5,6,7,8-tetrahydro-naphthalen-1-yl)-2H-pyran-2-one;

3-(3-Cyclopropylmethyl-5-isopropylphenyl)-4-hydroxy-6-[4-(pyridin-3-ylmethoxy)phenyl]-2H-pyran-2-one;

3-(3,5-Diisopropylphenyl)-4-hydroxy-6-[4-(pyridin-3-ylmethoxy)phenyl]-2H-pyran-2-one;

6-(Benzo[1,3]-dioxol-5-yl)-4-hydroxy-3-[(2-isopropylphenyl)thio]-2H-pyran-2-one;

4-Hydroxy-3-[(2-isopropylphenyl)thio]-6-[1-(phenylmethyl)cyclobutyl]-2H-pyran-2-one;

4-Hydroxy-3-[(2-isopropylphenyl)thio]-6-[1-(2-phenylethyl)cyclobutyl]-2H-pyran-2-one;

4-Hydroxy-3-[(2-isopropylphenyl)thio]-6-[1-(3-phenylpropyl)cyclobutyl]-2H-pyran-2-one;

4-Hydroxy-3-[(2-isopropyl-5-methylphenyl)thio]-6-(1-benzylcyclopropyl)-2H-pyran-2-one;

4-Hydroxy-3-[(2-isopropyl-5-methylphenyl)thio]-6-[1-(2-phenylethyl)cyclopropyyl]-2H-pyran-2-one;

4-Hydroxy-3-[(2-isopropyl-5-methylphenyl)thio]-6-[1-(3-phenylpropyl)cyclopropyl]-2H-pyran-2-one;

4-Hydroxy-3-[(2-isopropyl-5-methylphenyl)thio]-6-(1-benzylcyclobutyl)-2H-pyran-2-one;

4-Hydroxy-3-[(2-isopropyl-5-methylphenyl)thio]-6-[1-(2-phenylethyl)cyclobutyl]-2H-pyran-2-one;

4-Hydroxy-3-[(2-isopropyl-5-methylphenyl)thio]-6-[1-(3-phenylpropyl)cyclobutyl]-2H-pyran-2-one;

4-Hydroxy-3-[(2-isopropyl-5-methylphenyl)thio]-6-(1-benzylcyclopentyl)-2H-pyran-2-one;

4-Hydroxy-3-[(2-isopropyl-5-methylphenyl)thio]-6-[1-(2-phenylethyl)cyclopentyl]-2H-pyran-2-one;

4-Hydroxy-3-[(2-isopropyl-5-methylphenyl)thio]-6-[1-(3-phenylpropyl)cyclopentyl]-2H-pyran-2-one;

6-(1,1-Dimethyl-3-phenylpropyl)-4-hydroxy-3-[(2-isopropylphenyl) thio]-2H-pyran-2-one;

6-(1,1-Dimethyl-2-phenylethyl)-4-hydroxy-3-[(2-isopropylphenyl)thio]-2H-pyran-2-one;

4-Hydroxy-3-[(2-isopropylphenyl)thio]-6-(1-methyl-1-phenylethyl)-2H-pyran-2-one;

6-(1,1-Diethyl-3-phenylpropyl)-4-hydroxy-3-[(2-isopropylphenyl) thio]-2H-pyran-2-one;

6-(1-Benzyl-1-ethylpropyl)-4-hydroxy-3-[(2-isopropylphenyl)thio]-2H-pyran-2-one;

6-(1-Ethyl-1-phenylpropyl)-4-hydroxy-isopropylphenyl) thioisopropylphenyl)thio]-2H-pyran-2-one;

N-[3-[Cyclopropyl[6-(1,1-dimethyl-3-phenylpropyl)-4-hydroxy-2-oxo-2H-pyran-3-yl]methyl]phenyl] benzenesulfonamide;

N-[3-[Cyclopropyl[6-(1,1-dimethyl-2-phenylethyl)-4-hydroxy-2-oxo-2H-pyran-3-yl]methyl]phenyl] benzenesulfonamide;

N-[3-[Cyclopropyl[4-hydroxy-6-(1-methyl-1-phenylethyl)-2-oxo-2H-pyran-3-yl]methyl]phenyl] benzenesulfonamide;

N-[3-[Cyclopropyl[6-(1,1-diethyl-3-phenylpropyl)-4-hydroxy-2-oxo-2H-pyran-3-yl]methyl]phenyl] benzenesulfonamide;

N-[3-[Cyclopropyl[6-[1-ethyl-1-(phenylmethyl)propyl]-4-hydroxy-2-oxo-2H-pyran-3-yl]methyl]phenyl] benzenesulfonamide;

N-[3-[Cyclopropyl[6-(1-ethyl-1-phenylpropyl)-4-hydroxy-2-oxo-2H-pyran-3-yl]methyl]phenyl] benzenesulfonamide;

N-[3-[Cyclopropyl[4-hydroxy-2-oxo-6-[1-(2-phenylethyl) cyclopentyl]-2H-pyran-3-yl]methyl]phenyl] benzenesulfonamide;

N-[3-[[6-(1-Benzylcyclopentyl)-4-hydroxy-2-oxo-2H-pyran-3-yl]cyclopropylmethyl]phenyl] benzenesulfonamide;

N-[3-[Cyclopropyl[4-hydroxy-2-oxo-6-[1-(3-phenylpropyl) cyclopentyl]-2H-pyran-3-yl]methyl]phenyl] benzenesulfonamide;

N-[3-[Cyclopropyl[4-hydroxy-2-oxo-6-[1-(2-phenylethyl) cyclobutyl]-2H-pyran-3-yl]methyl]phenyl] benzenesulfonamide;

N-[3-[[6-(1-Benzylcyclobutyl)-4-hydroxy-2-oxo-2H-pyran-3-yl]cyclopropyl]methyl]phenyl]benzenesulfonamide;

N-[3-[Cyclopropyl[4-hydroxy-2-oxo-6-[1-(3-phenylpropyl) cyclobutyl]-2H-pyran-3-yl]methyl]phenyl] benzenesulfonamide;

N-[3-[Cyclopropyl[4-hydroxy-2-oxo-6-[1-(2-phenylethyl) cyclopropyl]-2H-pyran-3-yl]methyl]phenyl] benzenesulfonamide;

N-[3-[[6-(1-Benzylcyclopropyl)-4-hydroxy-2-oxo-2H-pyran-3-yl]cyclopropylmethyl]phenyl) benzenesulfonamide;

N-[3-[Cyclopropyl[4-hydroxy-2-oxo-6-[l-(3-phenylpropyl) cyclopropyl]-2H-pyran-3-yl]methyl]phenyl] benzenesulfonamide;

3-(Cyclopropylphenylmethyl)-6-(1,1-dimethyl-3-phenylpropyl)-4-hydroxy-2H-pyran-2-one;

3-(Cyclopropylphenylmethyl)-6-(1,1-dimethyl-2-phenylethyl)-4-hydroxy-2H-pyran-2-one;

3-(Cyclopropylphenylmethyl)-4-hydroxy-6-(1-methyl-1-phenylethyl)-2H-pyran-2-one;

3-(Cyclopropylphenylmethyl)-6-(1,1-diethyl-3-phenylpropyl)-4-hydroxy-2H-pyran-2-one;

6-(1-Benzyl-1-ethylpropyl)-3-(cyclopropylphenylmethyl)-4-hydroxy-2H-pyran-2-one and 3-(Cyclopropylphenylmethyl)-6-[1-ethyl-1-phenylpropyl]-4-hydroxy-2H-pyran-2-one.

6-(1-Benzylcyclopropyl)-3-[cyclopentyl (cyclopropylmethylthio)methyl]-4-hydroxy-2H-pyran-2-one;

6-(1-Benzylcyclobutyl)-3-[cyclopentyl (cyclopropylmethylthio)methyl]-4-hydroxy-2H-pyran-2-one;

6-(1-Benzylcyclopentyl)-3-[1-(cyclopentylthio)-2-cyclopropylethyl]-4-hydroxy-2H-pyran-2-one and 6-(1-Benzylcyclopentyl)-3-[1-(cyclopentylthio)-3-methylbutyl]-4-hydroxy-2H-pyran-2-one.

4. DETAILED DESCRIPTION OF THE INVENTION

Here, the term "alkyl", usually represented by an "R", means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, and dodecyl. The alkyl groups may contain one or more sites of unsaturation such as double or triple carbon-carbon bonds. The alkyl group is unsubstituted or substituted by from 1 to 3 substituents selected from alkyl, alkoxy, thioalkoxy all as defined herein, hydroxy, thiol, nitro, halogen, amino, formyl, carboxyl, nitrile, —NH—CO—R, —CO—NH—, —$CO_2$R, —COR, aryl, or heteroaryl wherein alkyl (R), aryl, and heteroaryl are defined as herein.

The term "cycloalkyl", also represented by an "R", means a hydrocarbon ring which contains from 3 to 12 carbon atoms unless otherwise specified, for example, cyclopropyl, cyclobutyl, cyclopentyl, cyclohexyl, and adamantyl. Where possible, the cycloalkyl group may contain a single double bond. The cycloalkyl ring may be unsubstituted or substituted by from 1 to 3 substituents selected alkyl, alkoxy, thioalkoxy all as defined herein, hydroxy, thiol, nitro, halogen, amino, formyl, carboxyl, nitrile, —NH—CO—R, —CO—NHR—, —$CO_2$R, —COR, aryl, or heteroaryl wherein alkyl (R), aryl, and heteroaryl are defined as herein.

The terms "alkoxy" and "thioalkoxy" are O-alkyl or S-alkyl as defined above for alkyl.

The term alkylcycloalkyl means a cycloalkyl attached to an alkyl chain where the terms cycloalkyl and alkyl are defined above.

The term spirocycle refers to a carbocyclic or heterocyclic ring whose ends meet at a single carbon in a ring or chain. Examples of such spirocycles are ring A in the following:

The term "aryl" means an aromatic radical which is a phenyl group, a benzyl group, a naphthyl group, a biphenyl group, a pyrenyl group, an anthracenyl group,

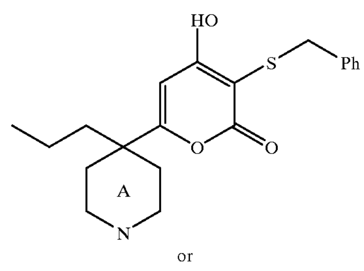

or

-continued

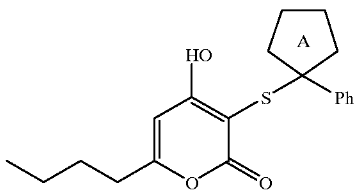

a fluarenyl group or a fused ring resulting from any two of phenyl, naphthyl, and a 5- or 6- membered ring containing from 0 to 3 heteroatoms selected from quinolones, isoquinolones, indoles, indanes, benzofurans, benzothiophenes, benzoxazoles, benzothiazoles, benzisoxazoles, coumarins, benzimidazoles and the like, unsubstituted or substituted by 1 to 3 substituents selected from alkyl as defined above, alkoxy as defined above, thioalkoxy as defined above, hydroxy, thiol, nitro, halogen, amino, formyl, carboxy, nitrile, —NHCOR, —CONHR, —$CO_2$R, —COR, aryl, or heteroaryl wherein alkyl (R), aryl, and heteroaryl are defined as above.

The terms "heteroaryl" and "heterocycle", usually represented by an "A", mean a heteroatom containing ring radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isaxazolyl, 3- or 5- 1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, 1- or 2- piperazinyl, 2-, 3-, or 4-morpholinyl, 2-, 3-, or 4-thiomorpholinyl, 1-, 2-, or 3-pyrrolidinyl, 2- or 3-tetrahydofuranyl, 1-, 2-, 3-, 4-, 5-, 6-, 7- or 8-tetrahydroquinolinyl, and the like, all of which may be unsubstituted or substituted by 1 to 2 substituents selected from alkyl as defined above, aryl as defined above, alkoxy as defined above, thioalkoxy as defined above, hydroxy, thiol, nitro, halogen, formyl, amino, carboxyl, nitrile, —NHCOR, $CO_2$R, —COR, wherein alkyl in as defined above or phenyl. "Halogen" is fluorine, chlorine, bromine or iodine.

Some of the compounds of Formula 1 are capable of further forming pharmaceutically acceptable acid-addition and/or base salts. All of these forms are within the scope of the present invention.

Pharmaceutically acceptable acid addition salts of the compounds of Formula 1 include salts derived from non-toxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al., "Pharmaceutical Salts," *Journal of Pharmaceutical Science,* 66: 1–19 (1977).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts," *Journal of Pharmaceutical Science,* 66: 1–19 (1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or a corresponding pharmaceutically acceptable salt of a compound of Formula 1.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit does preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of a retroviral protease, as agents for the treatment of infections caused by a retrovirus including HIV, or as agents for the treatment of diseases due to AIDS, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

4.1 General Synthetic Approaches to Pyrone Derivatives

Scheme I, shown below, illustrates the preparation of 6-substituted-3-substituted pyrones.

SCHEME I

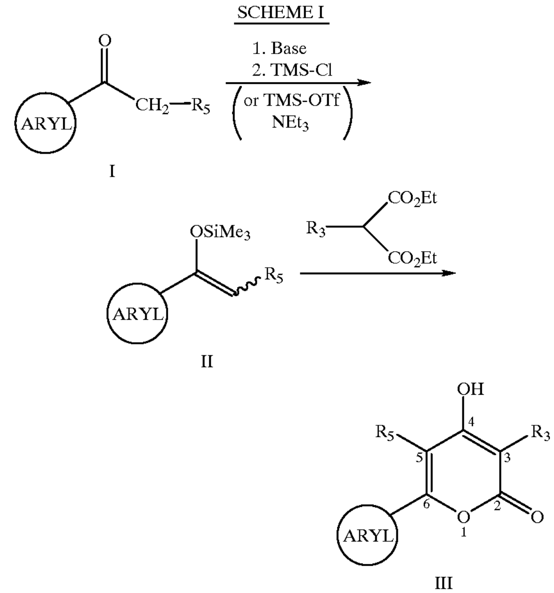

Ketone I is treated with a suitable base, such as lithium diisopropylamide or lithium bis(trimethylsilyl)amide, at −78° C. to −45° C., in ether or THF solution and, when deprotonation is complete, quenched with chlorotrimethylsilane (TMS-Cl), at −78° C. to 0° C., producing the silyl enol ether II. Alternatively, compound I is treated with trimethylsilyltrifluoromethanesulfonate (TMS-OTf) and triethylamine at 0° C. in dichloromethane solution, to effect transformation to intermediate II. Compound II is then reacted with an appropriately substituted malonate and heated either neat or in xylene at 130 −160° C. to give the desired product III.

For purposes of the above and other syntheses of the compounds of the present invention, reactive functional groups present in starting materials, reaction intermediates, or reaction products may be protected during chemical reactions using protecting groups which render the reactive functional groups substantially inert to the reaction conditions. (See for example, *Protective Groups in Organic Synthesis,* 2 ed., T. W. Green and P. G. Wuts, John Wiley & Sons, New York, N.Y. 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after completion of the synthetic reaction of interest, by procedures known to those skilled in the art. For example, the BOC group may be removed by acidolysis, the trityl group by hydrogenolysis, TBDMS by treatment with fluoride ions, and TCEC by treatment with zinc.

An alternative approach to functionalized pyrones is outlined in Scheme II.

SCHEME II

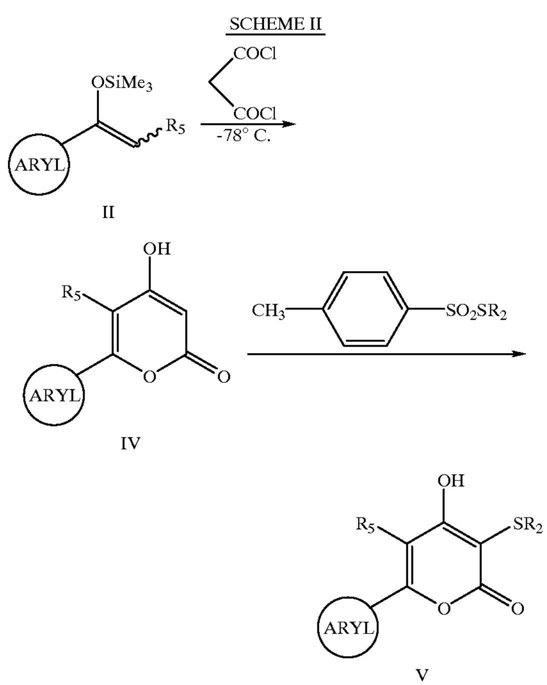

The trimethyl silyl enol ether II is reacted with malonyl dichloride in a dry solvent such as ether or THF at low temperature, preferably −78° C. to −35° C., to give pyrone IV, which is converted to the sulfur derivative V using an appropriately substituted p-toluenethiosulfonate, as disclosed in U.S. Pat. No. 3,931,235 (1976). Alternatively, the thiotosylate reagents were prepared as described by M. G. Ranasinghe and P. L. Fuchs in *Syn. Comm.* 18(3): 227 (1988). The requisite thiols can be prepared from the corresponding phenol via the Newman-Kwart rearrangement (see, for example, H. Kwart and H. Omura, *J. Amer. Chem. Soc.* 93: 7250 (1971); M. S. Newman and F. W. Hetzel, *Org. Synth. Coll. Vol.* VI: 824 (1988); M. S. Newman and H. A. Karnes, *J. Org. Chem.* 31: 3980 (1966)) or from the corresponding iodobenzene via a nucleophilic displacement with thiourea in the presence of a nickel catalyst (K. Takagi, *Chem. Letters,* 1307 (1985)).

A synthesis of pyrones such as VIII is shown below, in Scheme III. Here, substituent $R_6$ of structure VII can be aryl, alkyl, or substituted alkyl.

SCHEME III

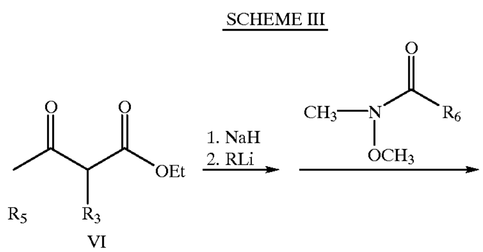

-continued

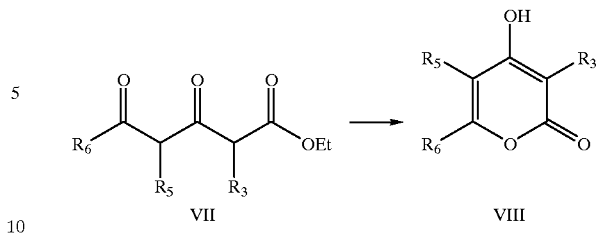

Substituted β-ketoester VI is deprotonated with one equivalent of a suitable base, e.g. a metal hydride such as sodium hydride, in a suitable solvent, e.g. ether or THF. A second equivalent of a stronger base, e.g. an alkyllithium such as n-butyllithium or lithium diisopropylamide, is added to the malonate solution to produce the dianion, which is then reacted with a suitable acylating agent, e.g. an amide, at 0° C. to 25° C. producing dione ester VII. Compound VII may then be cyclized to the pyrone VIII in a variety of ways, e.g. by using a strong acid such as $H_2SO_4$ or $CH_3SO_3H$, by heating the reaction mixture in a high boiling solvent such as xylene, or by using a small amount of a base, preferably a hindered base like 1,8-diazabicyclo[5.4.0]undec-7-ene. If $R_3$=H, then pyrone VIII can be further derivatized, as shown in Scheme II above.

Scheme IV describes the preparation of O-acyl pyrone analogues.

SCHEME IV

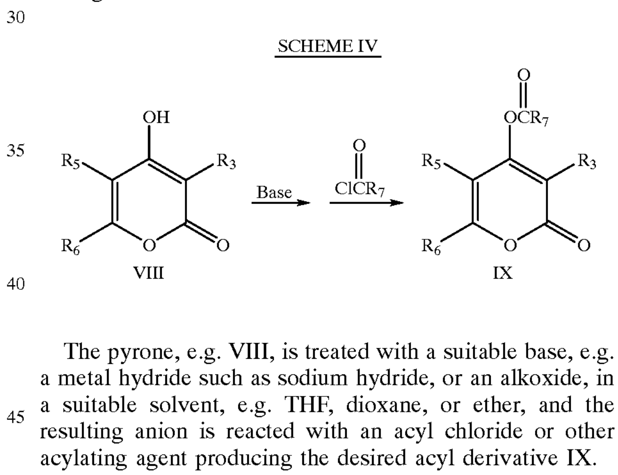

The pyrone, e.g. VIII, is treated with a suitable base, e.g. a metal hydride such as sodium hydride, or an alkoxide, in a suitable solvent, e.g. THF, dioxane, or ether, and the resulting anion is reacted with an acyl chloride or other acylating agent producing the desired acyl derivative IX.

Scheme V, shown below, illustrates the preparation of several 3-alkyl pyrone derivatives.

SCHEME V

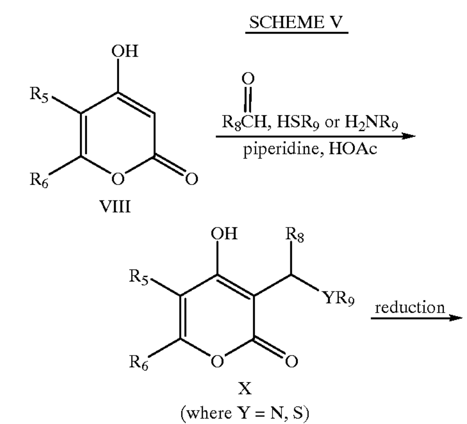

-continued

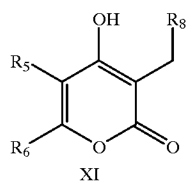

Intermediate pyrone VIII in an alcoholic medium, such as ethanol, is combined with a suitable aldehyde and a suitable nucleophile, such as $HSR_9$ or $NH_2R_9$, in the presence of a mixture of an acid, such as acetic acid, and a base, such as piperidine. The resulting mixture is heated at 60° C. to 90° C. to produce a pyrone X, which may itself be a preferred compound. Alternatively, for the case of Y═S, X may be reduced via a dissolving metal reduction, e.g. by using sodium in liquid ammonia, or via a reduction employing a Raney nickel system in a solvent such as acetone, to give desired 3-alkyl pyrones XI.

Scheme VI summarizes the synthesis of certain 3-amino pyrones.

described in U.S. Pat. No. 3,206,476 (1965). Reduction of nitropyrone XII with tin and acid furnishes aminopyrone XIII. Intermediate XIII can now be elaborated into a variety of derivatives. For example, XIII may be treated with an appropriately substituted aldehyde in the presence of a reducing agent, such as sodium borohydride or, preferably, sodium cyanoborhydride, to give the N-alkylated analogues XIV. Acylation of compound XIII may be achieved via one of several routes: 1. By treatment with sodium hydride, followed by coupling with a mixture of a suitable carboxylic acid, N-methylmorpholine, and a suitable condensing agent, such as 1-(3-dimethylaminopropyl)-3-ethylcarbodiimide, at a suitable temperature, e.g. −35° C.–0° C.; 2. By reaction with a suitable acid chloride or other acylating agent in the presence of a base, such as triethylamine, and 4-dimethylaminopyridine; or 3. By deprotonation with sodium hydride, followed by reaction with a suitable acid chloride in the presence of excess of an amine base, usually triethylamine, at elevated temperatures, e.g. 40–60° C. Ureas such as XVI may be prepared from aminopyrone XIII by reaction with a suitable isocyanate and a base, e.g. N-methylmorpholine, in an inert solvent such as ethyl acetate.

SCHEME VI

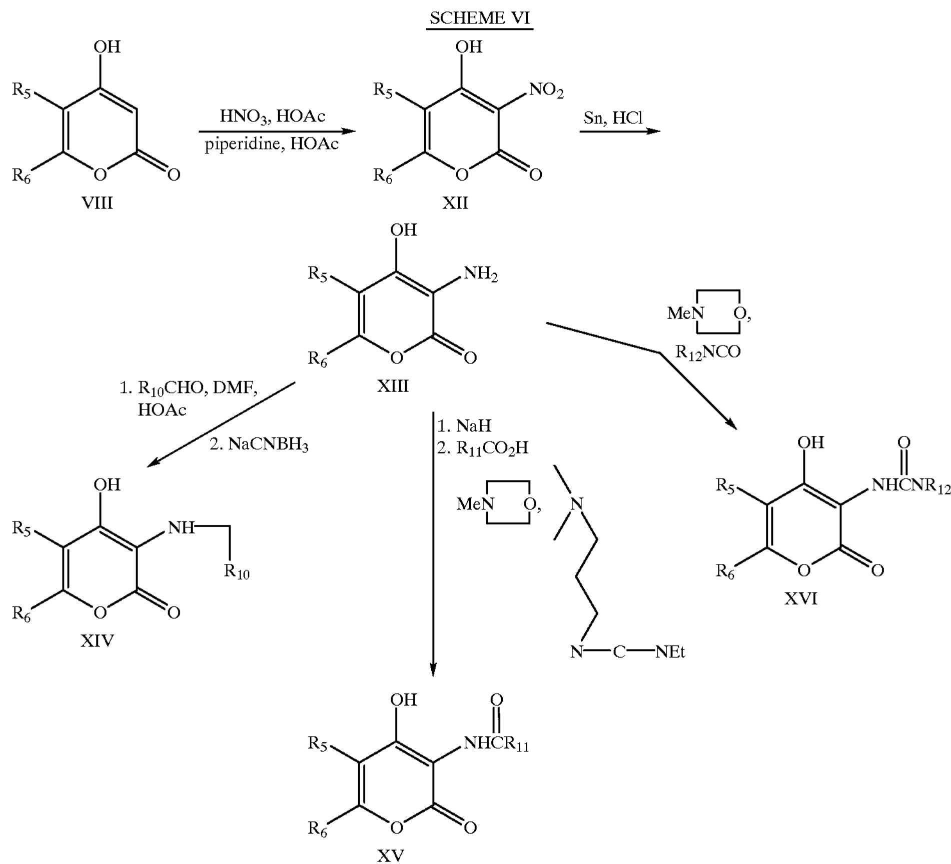

Nitration of pyrone VIII is effected with nitric acid, preferably fuming nitric acid in acid solution, e.g. as Scheme VII outlines an alternate approach for the preparation of C-6 substituted analogs.

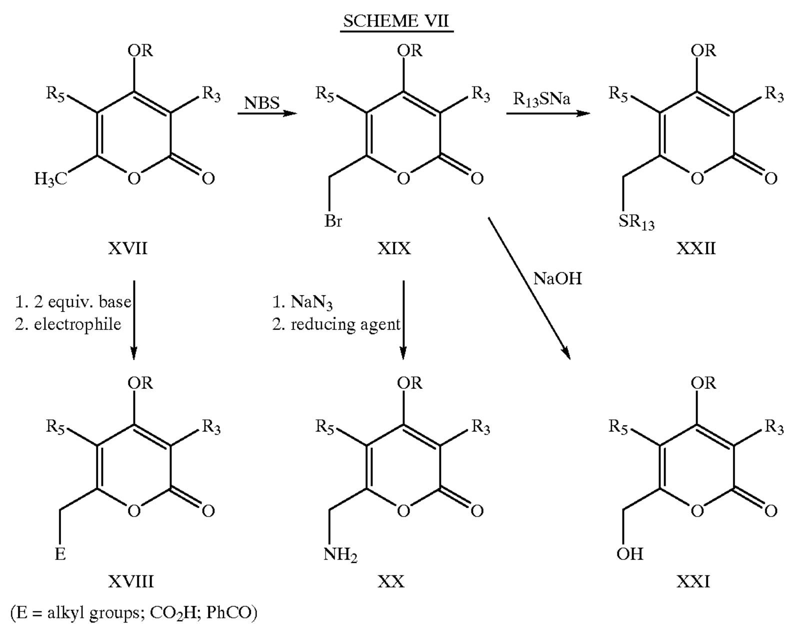

The 6-methyl pyrone XVII is treated with 2 equivalents of a strong base, e.g. sodium amide in liquid ammonia or lithium diisopropylamide in THF solution, followed by quenching with one of a great variety of electrophiles, e.g. alkyl halides, acylating agents, etc., furnishing pyrone XVIII (see M. P. Wachter and T. M. Harris, *Tetrahedron* 26: 1685 (1970)). Alternatively, allylic bromination of XVII under free radical conditions, e.g. using N-bromosuccinimide (NBS) in the presence of a free radical initiator and light, affords intermediate XIX, which can be further elaborated to amine XX as described in Jones et al., *Tetrahedron Letters,* 30: 3217 (1989), converted to alcohol XXI as described in R. Bacardit et al., *J. Heterocyclic Chem.* 19: 157 (1982), and ultimately transformed to sulfide XXII as described in R. Bacardit et al., *J. Heterocyclic Chem.* 26: 1205 (1989). The amino and hydroxy substituents of structures XX and XXI can be further derivatized using standard reactions known in the art, e.g. via alkylation, acylation, etc.

The synthesis of several 4-substituted pyrone derivatives is shown in Scheme VIII below.

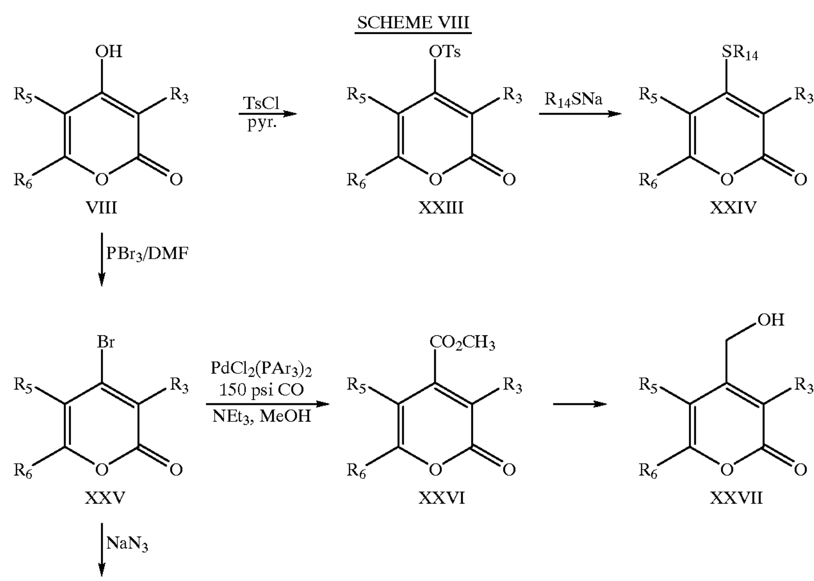

-continued

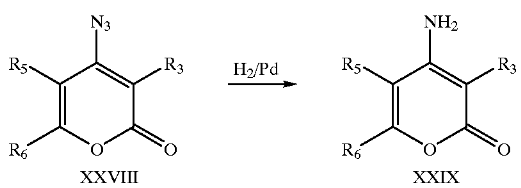

Pyrone VIII is activated, e.g. by tosylation to XXIII using p-toluenesulfonyl chloride (TsCl) in pyridine. The tosylate is then reacted with a suitable sulfur nucleophile (see A. M. Bittencourt et al., *Tetrahedron,* 27: 1043 (1971)) to give sulfide XXIV. In a similar fashion, pyrone VIII is converted to the 4-bromo analog XXV, using a brominating agent such as phosphorous-tribromide/dimethylformamide (DMF). Displacement of the bromine of XXV with azide followed by reduction (e.g. preferably hydrogenation over a palladium/triaryl-phosphine catalyst in a suitable solvent) gives 4-amino derivative XXIX. Further functionalization of the amine moiety of XXIX is achieved as described above in Scheme VI.

Alternatively, 4-bromopyrone XXV can be reacted with a palladium triarylphosphine catalyst and methanol in a carbon monoxide atmosphere to give ester XXVI. The ester can be further hydrolyzed, e.g. in acid solution at 0–25° C., to the corresponding carboxylic acid, or reduced, e.g. using a hydride reagent such as lithium aluminum hydride in THF or ether solution at 0° C.–25° C., to the alcohol (XXVII).

Scheme IX illustrates the preparation of 2H-thiopyran-2-one derivatives.

SCHEME IX

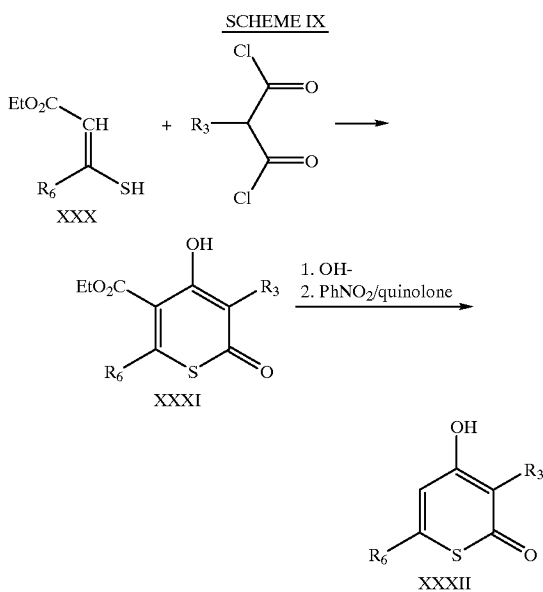

An appropriately substituted β-mercapto acrylate, e.g. XXX, is condensed with the desired malonyl dichloride in an inert solvent, e.g. toluene, at a temperature between 0° C. and the boiling point of the reaction solvent, to afford the thiopyran-2-one XXXI. Thiopyrone XXXI may be converted to derivative XXXII under suitable conditions, e.g. by basic hydrolysis followed by decarboxylation (for example, see F. K. Splinter and H. Arold, *J. Prakt. Chem.,* 38: 3–4, 142-6). Thiopyrones XXXII ($R_3$=H) can be converted to their substituted derivatives, using the procedures of Schemes II, X, and VI for derivatization of the analogous pyrones.

Suitably protected pyrones, e.g. XVII, as well as their analogs possessing S instead of O at position 1 of the pyrone ring, may be thiated, i.e. the carbonyl at position-2 of the heterocycle may be replaced by a thiocarbonyl (C=O→C=S), using standard group modification techniques, e.g. employing a thiation reagent such as Lawesson's reagent under suitable reaction conditions (see *Monatsh. Chem.,* 115: 769 (1984) and *Chem. Rev.* 84: 17 (1984).

4.2 General Procedures for the Preparation of Functionalized Pyrones

Method A: Synthesis via Reaction of Silyl Enol Ethers with 2-Substituted Propanedioic Acid Esters i) Preparation of Trimethylsilyl Enol Ethers To a solution of an appropriate ketone (10 mmol, 1 equivalent) in dry tetrahydrofuran (100 ml) at 78° C. was added lithium hexamethyldisilazide (11 mmol, 1.1 equivalents). The reaction mixture was stirred at −78° C. for 1 hour and at −35° C. for 0.5 hour. Trimethylchlorosilane was then added dropwise at −78° C., and the resulting mixture was stirred for 1 h at −78° C. and for 0.5 h at 0° C. The reaction was stirred at −78° C. for 1 h., and at 0° C. for 0.5 h. The reaction was interrupted by addition of saturated sodium bicarbonate solution and the reaction mixture extracted with ethyl acetate (300 ml). The ethyl acetate layer was washed with saturated sodium bicarbonate solution and brine, and dried further over anhydrous sodium sulfate. The ethyl acetate solution was concentrated under reduced pressure and the material isolated was dried in vacuo for 1 hour and used without purification.

ii) Condensation of Trimethylsilylenol Ethers with Dialkyl Esters of 2-Substituted Propanedioic Acid Crude trimethylsilyl enol ether (11 mmol, 1.1 equivalents), prepared as described above, was combined with a dialkyl ester of a 2-substituted propanedioic acid, (10 mmol, 1.0 equivalent) and the resulting mixture was heated at 150° C. with continuous passage of nitrogen gas through the reaction mixture, overnight. The reaction mixture was cooled to room temperature and the product was purified by chromatography on silica gel. Elution with 10–15% ethyl acetate/hexanes removed unreacted starting material and other impurities and elution with 30–50% ethyl acetate/5% methylene chloride/hexanes effected further purification furnishing the desired pyrones in 20–75% yield.

Method B: Sulfenylation of 6-Aryl-4-hydroxy-2H-pyran-2-one i) Preparation of 6-Aryl-4-hydroxy-2-pyrone The trimethylsilyl enol ether (20 mmol, 1 equivalent), prepared as described in Method A (or obtained commercially), was taken in anhydrous ethyl ether and cooled to −78° C. to −40° C. To it malonyl dichloride (30–40 mmol, 1.5–2 equivalents) was added dropwise. The reaction mixture was warmed up gradually to room temperature and stirred at room temperature overnight. The solid obtained was filtered and washed with anhydrous ether.

ii) Sulfenylation of 6-Aryl-4-hydroxy-2H-pyran-2-one

The 6-aryl-4-hydroxy-2-pyrone prepared as described above (1.62 mmol, 1 equivalent) was dissolved in ethanol. To this solution was added 1N sodium hydroxide (1.72 mL, 1.04 equivalents) or 2 equivalents of triethylamine, followed by the appropriate thiolsulfonate (1.72 mmol, 1.04 equivalents). The reaction mixture was heated at reflux for overnight. The solvents were evaporated, acidified with 1N HCl and the product was extracted with ethyl acetate. After evaporation of the solvents, the crude product was purified by chromatography (silica gel-230 to 400 mesh) using 30–50% of ethyl acetate in hexanes to yield the desired product. Yields: 40–80%.

Method C: Preparation of (6-Aryl-4-hydroxy-2-oxo-2H-pyran-3-yl) arylthiomethanes To the 6-aryl-4-hydroxy-2H-pyran-2-one (2.16 mmol; 1 eq) in 10 mL of ethyl alcohol, the appropriate aldehyde (2.37 mmol, 1.1 equivalents), appropriate thiol (5.62 mmol, 2.6 equivalents), piperidine (0.50 mL), and acetic acid (0.50 mL) were added. The reaction mixture was kept at 80° C. for 24 hours. The ethyl alcohol was evaporated, acidified with 1N HCl and the residue was purified by chromatography (silica gel-230 to 400 mesh) to yield 35–60% of the desired product.

Method D: Preparation of 6-Aryl-3-alkylamino-4-hydroxy-2H-pyran-2-ones i) 6-Aryl-4-hydroxy-3-nitro-2H-pyran-2-one The method used was adapted from the procedure described in U.S. Pat. No. 3,206,476 (1965) for nitration and reduction. To a suspension of 6-aryl-4-hydroxy-2H-pyran-2-one (2.65 mmol, ) in acetic acid (2.77 ml) at room temperature was added fuming nitric acid (0.222 ml). After stirring for 5 minutes, the reaction mixture was cooled to 0° C. and the product filtered. The product was purified by recrystallization from boiling acetic acid. $^{1}$H NMR (250 MHz, d-TFA) δ7.02 (s,1H), 7.65 (s, 3 H), 7.99 (m, 2 H).

ii) 3-Amino-6-aryl-4-hydroxy-2H-pyran-2-one

To a suspension of 6-aryl-4-hydroxy-3-nitro-2H-pyran-2-one (10.5 mmol, 1 equivalent) in acetic acid (15 ml) and concentrated HCl (7.34 ml) was added mossy tin (20.6 mmol, 1.96 equivalents). This mixture was then heated to reflux and a homogeneous mixture resulted. The reaction mixture was refluxed for 7 minutes, and then cooled in an ice bath. Concentrated HCl was added to precipitate the 3-amino-6-aryl-4-hydroxy-2H-pyran-2-one hydrochloride, which was collected and dried. $^{1}$H NMR (250 MHz, $D_2O$) δ6.74 (s,1H), 7.53 (m, 3 H), 7.84 (m, 2 H).

iii) 3-Alkylamino-6-aryl-4-hydroxy-2H-pyran-2-ones

To a solution of 3-amino-6-aryl-4-hydroxy-2H-pyran-2-one hydrochloride (2 mmol, 1 equivalent) in dimethyl formamide containing 1% acetic acid (20 ml) was added the aldehyde (2.1 to 4.2 mmol, 1.05–2.1 equivalents) followed by sodium cyanoborohyride (2.1 to 4.2 mmol, 1.05–2.1 equivalents). The reaction was stirred for 5 minutes, quenched with water and concentrated in vacuo. The oily residue was diluted with 100 ml of ethyl acetate, washed with water, then saturated sodium chloride, and dried over anhydrous magnesium sulfate. After evaporation of the solvents in vacuo the crude product was either purified by column chromatography (silica gel-230 to 400 mesh) or recrystallization to yield the desired product.

Method E: 3-Acylamino-6-aryl-4-hydroxy-2H-pyran-2-ones

The following procedures were used for amidation of the 3-amino-6-aryl-4-hydroxy-2H-pyran-2-ones.

a) To a solution of 3-amino-6-aryl-4-hydroxy-2H-pyran-2-one hydrochloride (0.84 mmol, 1.0 equivalent) in THF (10 ml) was added 60% sodium hydride (0.92 mmol, 1.1 equivalent) followed by stirring at room temperature for 30 min. In a separate flask, to the appropriate carboxylic acid (1.67 mmol, 2 equivalents) in THF (20 ml) at −20° C. was added N-methyl morpholine (0.92 mmol, 1.1 equivalent) followed by 1-(3-dimethylaminopropyl)-3-ethylcarbodiimide hydrochloride (0.92 mmol, 1.1 equivalent). The reaction mixture was stirred at −20° C. for 1 hr. This solution was added to the above 3-amino-6-aryl-4-hydroxy-2H-pyran-2-one followed by more N-methyl morpholine (0.918 mmol, 1.1 equivalent). The reaction mixture was stirred at room temperature overnight. The reaction was quenched by adding brine and diluting with ethyl acetate. The organic layer was washed in succession with 1 N HCl, water, saturated sodium chloride, and was then dried over anhydrous magnesium sulfate. After evaporation of the solvents in vacuo, the crude product was purified by column chromatography (silica gel-230 to 400 mesh) to yield the desired product.

b) To a suspension of 3-amino-6-aryl-4-hydroxy-2H-pyran-2-one, monohydrochloride (0.83 mmol, 1.0 equivalent) in methylene chloride (8 mL) was added triethylamine (3.3 mmol, 4.0 equivalents) followed by a catalytic amount of 4-dimethylaminopyridine (0.08 mmol, 0.1 equivalent) and the appropriate acid chloride (0.92 mmol, 1.1 equivalent). The reaction was stirred at room temperature for 6 hours. The reaction was quenched with 1N hydrochloric acid and then diluted with methylene chloride. The organic layer was washed with water and saturated sodium chloride, and then dried over anhydrous magnesium sulfate. After evaporation of the solvents in vacuo, the crude product was recrystallized from boiling acetic acid.

c) To a solution of 3-amino-6-aryl-4-hydroxy-2H-pyran-2-one monohydrochloride (0.63 mmol, 1.0 equivalent) in tetrahydrofuran (6 mL) at 0° C. was added 60% sodium hydride (0.69 mmol, 1.1 equivalents). The resulting mixture was stirred at room temperature for 15 minutes. To the reaction mixture, the corresponding acid chloride (0.69 mmol, 1.1 equivalents) was added. The reaction mixture was heated to 50° C. for 1 hour and overnight at room temperature. The reaction was quenched with 1N hydrochloric acid and diluted with ethyl acetate. The organic layer was washed with is saturated sodium chloride, dried over anhydrous magnesium sulfate. After evaporation of the solvents in vacuo, the crude product was recrystallized from boiling nitromethane to yield the pure product.

Method F: Preparation of 3-Alkyl-6-aryl-4-hydroxy-2H-pyran-2-ones

The (6-aryl-4-hydroxy-2-oxo-2H-pyran-3-yl) arylthiomethanes were prepared as described in Method C. Raney-Nickel (Grace 3100) was boiled in acetone for 45 minutes and the acetone was replaced with ethanol (20 ml). The (4-hydroxy-6-substituted-2-oxo-2H-pyran-3-yl) arylthiomethane (1.0 mmol, 1 equivalent) was added and the resulting slurry was heated to reflux overnight. The mixture was filtered through Celite and washed with hot ethanol. The filtrate was concentrated in vacuo to yield pure products.

Method G: Preparation of 4-Acyloxy Esters of 4-Hydroxy-3-aryl(or arylalkyl)thio-6-aryl-2H-pyran-2-one The 4-hydroxy-3-aryl(or arylakyl)thio-6-aryl-2H-pyran-2-one (3 mmol, 1 equivalent) was dissolved in 20 mL of tetrahydrofuran and cooled to 0° C. To this mixture was added sodium hydride (3.3 mmol, 1.1 equivalent) slowly and the resultant mixture was stirred at room temperature for 15 minutes. The corresponding acid chloride (6 mmol, 2 equivalents) was added drop-wise and the reaction was stirred at room temperature overnight. The reaction was quenched with saturated sodium chloride solution and was diluted with 100 mL of ethyl acetate. The combined organic layer was washed with sodium bicarbonate solution, brine, and dried over anhydrous sodium sulfate. After evaporation of the solvents, the crude product was purifed by column chromatography (silica gel-230 to 400 mesh) using 10% ethyl acetate in hexane as eluents afforded the enol ester in 70–85% yields.

4.3 Preparation of Starting Materials

EXAMPLES A–E

Preparation of Propanedioic Acids

The following key intermediates were synthesized according to the procedure described in *Comptus rendus* 255: 2611 (1962).

Example A

Diethyl ester of [(phenylmethyl)thio]-propanedioic acid b.p. 160–162° C./6 mm Hg;

$^{1}$H NMR (250 MHz, DMSO-d6) δ1.18 (t, 6 H), 3.93 (s, 2 H), 4.13 (q, 4 H), 4.44 (s, 1 H), 7.31 (m, 5 H).

Example B

Dimethyl ester of [(2-naphthalenylmethyl)thio]-propanedioic acid

The crude product was purified by silica gel chromatography (silica gel 230–400 mesh). $^{1}$H NMR (250 MHz, DMSO-$d_6$) δ3.65 (s, 6 H), 4.10 (s, 2 H), 4.55 (s, 1 H), 7.51 (m, 3 H), 7.87 (m, 4 H).

Example C

Diethyl ester of [(3-phenylpropyl)thio]-propanedioic acid b.p. 185–190° C./1 mm Hg;

$^{1}$H NMR (400 MHz, DMSO-$d_6$) δ1.17 (t, 6 H), 1.82 (m, 2 H), 2.65 (q, 4 H), 4.14 (q, 4 H), 4.62 (s, 1 H), 7.23 (m, 5 H).

Example D

Diethyl ester of [(2-naphthalenyl)thio]-propanedioic acid

The crude product was purified by silica gel chromatography (silica gel 230–400 mesh). $^{1}$H NMR (250 MHz, DMSO-$d_6$) δ1.09 (t, 6 H), 4.12 (q, 4 H), 5.27 (s, 1 H), 7.58 (m, 3 H), 7.90 (m, 3 H), 8.80 (s, 1 H).

Example E

Diethyl ester of [(2-phenylethyl)thio]-propanedioic acid b.p.: 160–165° C./1 mm of Hg.

$^{1}$H NMR (400 MHz), DMSO-$d_6$) δ1.19 (t, 6 H), 2.89 (m, 2 H), 4.16 (q, 4 H), 4.68 (s, 1 H), 7.25 (m, 5 H).

Examples F–M

Preparation of p-Toluenethiosulfonates

The following p-toluenethiosulfonates were synthesized according to the procedure described in U.S. Pat. No. 3,931,235 (1976).

Example F

2-Phenoxyethyl p-Toluenethiosulfonate $^{1}$H NMR (400 MHz, DMSO-$d_6$) δ2.41 (s, 3 H), 3.41 (t, 2 H), 4.13 (t, 2 H), 6.83 (d, 2 H), 6.94 (t, 1 H), 7.27 (t, 2 H), 7.48 (d, 2 H), 7.85 (d, 2 H).

Example G

3-Phenyl-2-propenyl p-Toluenethiosulfonate $^{1}$H NMR (400 MHz, DMSO-$d_6$) δ2.32 (s, 3 H), 3.93 (d, 2 H), 6.00 (dt, 1 H), 6.58 (d, 1 H), 7.29 (m, 5 H), 7.38 (d, 2 H), 7.81 (d, 2 H).

Example H

2-[2-Methoxypenyl]ethyl p-Toluenethiosulfonate $^{1}$H NMR (400 MHz, DMSO-$d_6$) δ2.43 (s, 3 H), 2.80 (t, 2 H), 3.19 (t, 2 H), 3.75 (s, 3 H), 6.83 (t, 1 H), 6.93 (d, 1 H), 7.02 (d, 1 H), 7.21 (t, 1 H), 7.49 (d, 2 H), 7.81 (d, 2 H).

Example I

4-Phenylbutyl p-Toluenethiosulfonate $^{1}$H NMR (400 MHz, DMSO-$d_6$) δ1.53 (m, 4 H), 2.43 (s, 3 H), 2.50 (t, 2 H), 3.03 (t, 2 H), 7.12 (d, 1 H), 7.18 (d, 2 H), 7.25 (t, 2 H), 7.45 (d, 2 H), 7.80 (d, 2 H).

Example J

2-[3-Methoxyphenyl]ethyl p-Toluenethiosulfonate $^{1}$H NMR (400 MHz, DMSO-$d_6$) δ2.43 (s, 3 H), 2.79 (t, 2 H), 3.25 (t, 2 H), 3.73 (s, 3 H), 6.73 (m, 3 H), 7.19 (m, 1 H), 7.49 (d, 2 H), 7.83 (d, 2 H).

Example K

2-[4-Methoxyphenyl]ethyl p-Toluenethiosulfonate $^{1}$H NMR (400 MHz, DMSO-$d_6$) δ2.50 (s, 3 H), 2.76 (t, 2 H), 3.21 (t, 2 H), 3.71 (s, 3 H), 6.83 (t, 2 H), 7.03 (d, 2 H), 7.50 (t, 2 H), 7.82 (d, 2 H).

Example L 2-(2-Chlorophenyl)ethyl p-Toluenethiosulfonate $^{1}$H NMR (400 MHz, DMSO-$d_6$) δ2.43 (s, 3 H), 2.86 (t, 2 H), 3.28 (t, 2 H), 7.22 (m, 4 H), 7.49 (d, 2 H), 7.83 (d, 2 H).

Example M

[4-(Phenylmethoxy)phenyl]methyl p-Toluenethiosulfonate $^{1}$H NMR (400 MHz, DMSO-$d_6$) δ2.41 (s, 3 H), 4.28 (s, 2 H), 5.06 (s, 2 H), 6.87 (d, 2 H), 7.13 (d, 2 H), 7.37 (m, 7 H), 7.72 (d, 2 H).

Example N 6-(3-Chlorophenyl)-4-hydroxy-2H-pyran-2-one

A slurry of 60% NaH (0.790 g, 19.7 mmol) in THF (50 mL) under a $N_2$ atmosphere was cooled to 0° C. and treated with ethyl acetoacetate (2.51 mL, 19.7 mmol). The resulting solution was subsequently treated with n-BuLi (12.3 mL, 19.7 mmol) and stirred for 20 min. at 0° C. to provide an orange solution which was treated via cannula with a solution of 3-chloro-N-methoxy-N-methylbenzamide (2.50 g, 15.15 mmol) in THF (5.0 mL). The mixture was allowed warm to ambient temperature where it was stirred for 14 h before being quenched with 2.0 N HCl. The product was extracted with ethylacetate (3×50 mL), the layers combined, dried with $Na_2SO_4$, and the solvent removed in vacuo. The residue was then treated with conc. $H_2SO_4$ (20 mL) and the resulting mixture stirred for 18 h at room temperature before being diluted with $H_2O$ (200 mL). The product was then extracted with ethylacetate (3×100 mL) being sure to collect all solids. The layers were then combined and diluted with acetone to provide a homogenous solution which was dried with $Na_2SO_4$. The solvent was then removed in vacuo and the resulting solid recrystallized from acetone-hexane to provide the title compound (1.33 g, m.p. 254–256° C.). $^1$H NMR (400 MHz, DMSO-$d_6$) δ11.957 (bs, 1 H), 7.889 (t, 1 H, J =1.5 Hz), 7.839–7.813 (m, 1 H), 7.598–7.524 (m, 2 H), 7.876 (d, 1 H, J=2 Hz), 5.450 (d, 1 H, J=2 Hz).

Example O 6-(4-Chlorophenyl)-4-hydroxy-2H-pyran-2-one

The title compound (1.56 g, m.p. 247–249° C.) was prepared in a similar manner as that demonstrated in the preparation of Example N using the following: 60% NaH (0.904 g, 22.6 mmol), THF (50 mL), ethyl acetoacetate (3.00 g, 22.6 mmol), lithium diisopropylamine in THF (39.8 mL, 24 mmol), 4-chloro-N-methoxy-N-methylbenzamide (3.73 g, 22.6 mmol), 90% $H_2SO4$ (20 mL). H NMR (300 MHz, DMSO-$d_6$) δ11.950 (bs, 1 H), 7.878 (d, 1 H, J=9 Hz), 7.584 (d, 1 H, J=9 Hz), 6.812 (d, 1 H, J=2 Hz), 5.409 (d, 1 H, J=2 Hz).

Example P (Cyclopropylmethyl)-p-toluenethiosulfonate

To a solution of methylcyclopropyl bromide (4.00 g, 29.6 mmol) in ethanol (20.0 mL) was added potassium thiotosylate (10.0 g, 44.4 mmol) and the mixture heated to 90° C. for 10 h. The mixture was then quenched into a 1:1 mixture of $H_2O$ (50.0 mL) and diethyl ether (50.0 mL). The layers were separated and the organic layer washed with brine (50.0 mL). The organic layer was then dried with $MgSO_4$ and concentrated in vacuo to yield the title compound as a solid (5.2 g, m.p. 46–48° C.). $^1$H NMR (400 MHz, $CDCl_3$) δ7.816 (d, 2 H, J=8.8 Hz), 7.308 (d, 2 H, J =8.8 Hz), 2.945 (d, 2 H, J=7.6 Hz), 2.451 (s, 3 H), 1.010–0.933 (m, 1 H), 0.592–0.545 (m, 2 H), 0.236–0.197 (m, 2 H).

Example Q

Methyl-[4-(1-oxoethyl)phenoxy] Acetate

A mixture of 4-hydroxypropiophenone (10.0 g, 60.24 mmol), $CsCO_3$ (21.6 g, 66.3 mmol), and acetone (150.0 mL) under an $N_2$ atmosphere was treated with methylbromoacetate (7.26 mL, 78.3 mmol) and the mixture heated to reflux for 4 h. The mixture was then allowed to cool to ambient temperature, diluted with $H_2O$ (150 mL) and extracted with $CH_2Cl_2$ (2×300 mL). The organic layers were combined, dried with $Na_2SO_4$, and the solvent removed in vacuo to provide the title compound (12.75 g, m.p. 64–66° C.). $^1$H NMR (400 MHz, DMSO-$d_6$) δ9.35 (d, 2 H, J=8.9 Hz), 7.040 (d, 2 H, J=8.9 Hz), 4.920 (s, 2 H), 3.715 (s, 3 H), 2.981 (q, 2 H, J=7.2 Hz), 1.071 (t, 3 H, J=7.2 Hz).

4.4 Preparation of Specific Pyrone Derivatives

Example 1

6-(3-Chlorophenyl)-4-hydroxy-3-[(phenylmethyl)thio]-2H-pyran-2-one

Following method A a solution of 3'-chloroacetophenone (1.50 g, 11.6 mmol) in THF (10.0 mL) was cooled to −78° C. ($N_2$ atmosphere) and treated with a 1.0 M solution of lithium hexamethyldisilazide (12.5 mL, 12.5 mmol) in THF. The solution was warmed to 0° C., allowed to stir for 15 min., then treated with trimethylsilylchloride (1.47 mL, 11.6 mmol) The reaction mixture was then allowed to stir for 0.5 h (ambient temperature) and subsequently quenched into a mixture of diethyl ether (50 mL) and saturated aqueous $NaHCO_3$ (20 mL). The layers were separated and the organic layer washed with a 1:1 mixture of brine saturated $NaHCO_3$ (20 mL). The ethereal solution was then dried with $Na_2SO_4$ and the solvent removed in vacuo. The resulting silyl enol ether was then transferred to a flask containing diethyl-2-(thiobenzyl)propane-1,3-dioate (1.63 g, 5.80 mmol), the resulting mixture heated to 160° C. for 16 h. and then allowed to cool to room temperature where it was diluted with diethyl ether (20 mL) and extracted with saturated $Na_2CO_3$ (3×20 mL). The aqueous layer was then acidifed with conc. HCl to pH 0 and then extracted with ethyl acetate (3×100 mL). The organic layers were combined, dried with $Na_2SO4$ and the solvent removed in vacuo. The resulting residue was then submitted to chromatography ($SiO_2$-230 to 400 mesh, 100% $CH_2Cl_2$ to 1% $MeOH/CH_2Cl_2$) to provide a solid which was recrystallized from acetone/hexanes to provide 0.436 g (m.p. 136–137° C.) of the title compound. $^1$H NMR (400 MHz, DMSO-$d_6$) δ11.950 (bs, 1 H), 7.814 (s, 1 H), 7.761 (d, 1 H, J=7.5 Hz), 7.616–7.534 (m, 2 H), 7.271–7.185 (m, 5 H), 6.811 (s, 1 H), 4.023 (s, 2 H).

Example 2

6-(2-Chlorophenyl)-4-hydroxy-3-[(phenylmethyl)thio]-2H-pyran-2-one

The title compound (0.210 g, m.p. 99–101° C.) was prepared by method A using 2'-chloroacetophenone (1.50 mL, 11.6 mmol), 1.87 M potassium hexamethyldisilazide (6.80 mL, 12.7 mmol), trimethylsilylchloride (1.47 mL, 11.6 mmol), THF (10.0 mL), diethyl 2-(thiobenzyl)propane-1,3-dioate (1.3 g, 4.63 mmol). $^1$H NMR (400 MHz, DMSO-$d_6$) δ12.153 (bs, 1 H), 7.639 (t, 2 H, J=9 Hz), 7.572–7.477 (m, 2 H), 7.276–7.206 (m, 5 H), 6.558 (s, 1 H), 4.029 (s, 2 H).

Example 3

6-(3,4-Dichlorophenyl)-4-hydroxy-3-[(phenylmethyl)thio]-2H-pyran-2-one

The title compound (0.201 g, m.p. 185–186° C.) was prepared by method A using 3',4'-dichloroacetophenone (1.5 g, 7.9 mmol), 1.0 M lithium hexamethyldisilazide (8.7 mL, 8.69 mmol), trimethylsilylchloride (1.0 mL, 7.9 mmol), THF (10.0 mL), diethyl 2-(thiobenzyl)propane-1,3-dioate (0.89 g, 3.2 mmol). $^1$H NMR (400 MHz, DMSO-$d_6$) δ12.000 (bs, 1 H), 8.018 (s, 1 H), 7.784 (s, 2 H), 7.265–7.179 (m, 5 H), 6.839 (s, 1 H), 4.017 (s, 2 H).

Example 4

4-Hydroxy-6-(3-methoxyphenyl)-3-[(phenylmethyl)thio]-2H-pyran-2-one

The title compound (0.400 g, m.p. 146–147° C.) was prepared by method A using 3'-methoxyacetophenone (1.5 mL, 10.9 mmol), potassium hexamethyldisilazide (6.41 mL, 12.0 mmol), trimethylsilylchloride (1.38 mL, 10.9 mmol), THF (10.0 mL), diethyl 2-(thiobenzyl)propane-1,3-dioate (1.23 g, 4.36 mmol). $^1$H NMR (400 MHz, DMSO-$d_6$) δ11.880 (bs, 1 H), 7.445 (t, 1 H, J=8 Hz), 7.370 (d, 1 H, J=8 Hz), 7.286–7.094 (m, 6 H), 7.109 (m, 1 H), 6.770 (s, 1 H), 4.020 (s, 2 H), 3.831 (s, 3 H).

Example 5

4-Hydroxy-3-[(phenylmethyl)thio]-6-(3,4,5-trimethoxyphenyl)-2H-pyran-2-one

The title compound (0.385 g, m.p. 156–157° C.) was prepared by method A using 3', 4', 5'-trimethoxyacetophenone (2.0 g, 9.5 mmol), potassium hexamethyldisilazide (5.6 mL, 10.45 mmol), trimethylsilylchloride (1.2 mL, 9.5 mmol), THF (15 mL), diethyl 2-(thiobenzyl)propane-1,3-dioate (1.07 g, 3.80 mmol). $^1$H NMR (400 MHz, DMSO-$d_6$) δ11.778 (bs, 1 H), 7.265–7.181 (m, 5 H), 7.054 (s, 2 H), 6.792 (s, 1 H), 3.997 (s, 2 H), 3.861 (s, 6 H), 3.727 (s, 3 H).

Example 6

6-(3-Chlorophenyl)-4-hydroxy-3-[(2-phenylethyl)thio]-2H-pyran-2-one

The title compound (0.138 g m.p. 125–127° C.) was prepared by method B using 6-(3-chlorophenyl)-4-hydroxy-2H-pyran-2-one (0.250 g, 1.10 mmol), phenethyl-p-toluenethiosulfonate (0.43 g, 1.46 mmol), triethylamine (0.35 mL, 2.5 mmol), ethanol (5.0 mL). $^1$H NMR (400 MHz, $CDCl_3$) δ7.838 (t, 1 H, J=1.5 Hz), 7.710 (d, 1 H, J=8 Hz), 7.530 (bs, 1 H), 7.475–7.392 (m, 2 H), 7.308–7.260 (m, 2 H), 7.207–7.171 (m, 3 H), 6.604 (s, 1 H), 3.125 (t, 2 H, J=7 Hz), 2.897 (t, 2 H, J=7 Hz).

Example 7

6-(4-Chlorophenyl)-4-hydroxy-3-[(2-phenylethyl)thio]-2H-pyran-2-one

The title compound (0.242 g, m.p. 161–163° C.) was prepared by method B using 6-( 4-chlorophenyl)-4-hydroxy-2H-pyran-2-one (0.250 g, 1.12 mmol), phenethyl-p-toluenethiosulfonate (0.390 g, 1.35 mmol), triethylamine (0.31 mL, 2.24 mmol), ethanol (10.0 mL). $^1$H NMR (400 MHz, DMSO-$d_6$) δ12.085 (bs, 1 H), 7.827 (d, 2 H, J=9 Hz), 7.605 (d, 2 H, J=9 Hz), 7.259–7.142 (m, 5 H), 6.830 (s, 1 H), 3.017 (t, 2 H, J=7.5 Hz), 2.785 (t, 2 H, J=7.5 Hz).

Example 8

4-Hydroxy-6-phenyl-3-[(phenylmethyl)]thio]-2H-pyran-2-one

The title compound was prepared by Method A using 1-phenyl-1-(trimethylsilyloxy)ethylene (1.00 g, 5.19 mmol) and the diethyl ester of [(phenylmethyl)thio]-propandioic acid (0.977 g, 3.46 mmol). m.p. 155–160° C.; $^1$H NMR (250 MHz, DMSO-$d_6$) δ4.00 (s, 2H), 6.74 (s, 1 H), 7.23 (m, 5 H), 7.53 (m, 3 H), 7.78 (m,2 H).

Example 9

4-Hydroxy-6-phenyl-3-[(phenylmethyl)amino]-2H-pyran-2-one

The title compound was prepared by method D using 3 -amino-4 -hydroxy-6-phenyl-2H-pyran-2 -one hydrochloride (0.500 g, 2.08 mmol), 1% acetic acid in dimethylformamide (20 mL), benzaldehyde (0.233 mL, 2.29 mmol), sodium cyanoborohydride (0.144 g, 2.29 mmol). m.p. dec. 205° C., $^1$H NMR (250 MHZ, DMSO-$d_6$) δ4.37 (s, 2 H), 6.56 (s, 1 H), 7.27 (m, 5 H), 7.45 (m, 3 H), 7.67 (m, 2 H).

Example 10

N-(1,1-Dimethylethyl)-N'-(4-hydroxy-2-oxo-6-phenyl-2H-pyran-3-yl)-N'-(phenylmethyl) Urea To a suspension of 4-hydroxy-6-phenyl-3-(phenylmethyl)amino-2H-pyran-2-one, monohydrochloride (0.153 mmol) in ethyl acetate (10 ml) was added N-methylmorpholine (2.0 ml) and tert-butyl isocyanate (2.0 ml). The reaction was allowed to stir for 2.5 hrs and then quenched by dilution with ethyl acetate. The organic layer was washed with 5% citric acid and saturated sodium chloride and was dried over anhydrous magnesium sulfate. After evaporation of the solvents in vacuo the crude product was purified by column chromatography (silica gel-230 to 400 mesh) using 5% methanol in dichloromethane as eluents.

$^1$H NMR (250 MHz, DMSO-$d_6$) δ1.24 (s, 9H), 4.47 (dd, 2 H), 5.45 (bs, 1 H), 7.23 (m, 5 H), 7.51 (m, 3 H), 7.75 (m, 2 H).

Example 11

4-Hydroxy-3-[(2-naphthalenylmethyl)thio]-6-phenyl-2H-pyran-2-one

The title compound was prepared by Method A using 1-phenyl-1-(trimethylsilyloxy)ethylene (0.475 g, 2.46 mmol) and dimethyl ester of [(2-naphthalenylmethyl)thio] propanedioic acid (0.500 g, 1.64 mmol). m.p. dec>250° C.; $^1$H NMR (250 MHz, DMSO-$d_6$) δ4.06 (s, 2 H), 6.47 (s, 1 H), 7.46 (m, 6 H), 7.78 (m, 6 H).

Example 12

4-Hydroxy-3-[(2-naphthalenylthio]-6-phenyl-2H-pyran-2-one

The title compound was prepared by Method A using 1-phenyl-1-(trimethylsilyloxy) ethylene (1.33, 6.90 mmol) and diethyl ester of [(2-naphthalenyl)thio]-propanedioic acid (2.00 g, 6.29 mmol). m.p. dec. 246° C.; $^1$H NMR (250 MHz, DMSO-$d_6$) δ6.95 (s1), 7.38 (m, 3 H), 7.56 (m, 4 H), 7.85 (m, 5 H).

Example 13

4-Hydroxy-3-[(phenylmethyl)thio]-6-(2,4,6-trimethylphenyl)-2H-pyran-2-one

The title compound was prepared by Method A using 2',4',6'-trimethylacetophenone (1.86 g, 11.5 mmol), lithium bis(trimethylsilyl)amide (2.11 g, 12.65 mmol), chlorotrimethylsilane (1.60 mL, 12.65 mmol), THF (127 mL), and diethyl ester of [(phenylmethyl)thio]propanedioic acid (2.95 g, 10.4 mmol). m.p. 134–136° C.; $^1$H NMR (250 MHz, DMSO-$d_6$) δ2.11 (s, 6 H), 2.26 (s, 3 H), 3.98 (s, 2 H), 6.03 (s, 1 H), 6.96 (s, 2 H), 7.25 (m, 5 H), 11.85 (bs, 1 H).

Example 14

4-Hydroxy-6-[4-[2-(4-morpholinyl)ethoxy]phenyl]-3-[(phenylmethyl)thio]-2H-pyran-2-one The title compound was prepared by Method A using 4'-[2-(4-morpholinyl)ethoxy]acetophenone (1.31 g, 5.29 mmol), lithium bis(trimethylsilyl)amide (0.972 g, 5.81 mmol), chlorotrimethylsilane (0.738 mL, 5.81 mmol), THF (58 mL), and diethyl ester of [(phenylmethyl)thio] propanedioic acid (1.35 g, 4.80 mmol). m.p. dec. 207° C.; $^1$H NMR (250 MHz, DMSO-$d_6$) δ2.54 (s, 2 H), 6.89 (m, 4 H), 2.83 (t, 2 H), 3.55 (m, 4 H), 3.96 (s, 2 H), 4.22 (t, 2 H), 6.58 (s, 1 H), 7.08 (d, 2 H), 7.23 (m, 5 H), 7.73 (d, 2 H).

Example 15

4-Hydroxy-6-(2-naphthalenyl)-3-[(phenylmethyl) thio]-2H-pyran-2-one

The title compound was prepared by Method A using 2-acetyl naphthalene (1.97 g, 11.6 mmol), lithium bis (trimethylsilyl)amide (2.13 g, 12.76 mmol), chlorotrimethylsilane (1.61 mL, 12.76 mmol), THF (127 mL), and diethyl ester of [(phenylmethyl)thio]-propanedioic acid (2.90 g, 10.5 mmol). m.p. dec. 203° C.; $^1$H NMR (250 MHz, DMSO-d6) δ4.04 (s, 2 H), 6.89 (s, 1 H), 7.23 (m, 5 H), 7.61 (m, 2 H), 7.84 (d, 2 H), 8.05 (m, 3 H), 8.43 (s, 1 H), 11.95 (bs, 1 H).

Example 16

4-Hydroxy-6-phenyl-3-[(phenylthio)methyl]-2H-pyran-2-one

The title compound was prepared by Method C using 4-hydroxy-6-phenyl-2H-pyran-2-one (1.00 g, 5.31 mmol), ethanol (10 mL), paraformaldehyde (0.175 g, 5.80 mmol), thiophenol (1.40 mL, 13.8 mmol), piperdine (0.5 mL), acetic acid (0.5 mL). m.p. dec. 211° C.; $^1$H NMR (400 MHz, DMSO-$d_6$) δ3.98 (s, 2 H), 6.73 (s, 1 H), 7.17 (m, 1 H), 7.30 (m, 2 H), 7.37 (m, 2 H), 7.54 (m, 3 H), 7.77 (m, 2 H), 12.05 (bs, 1 H).

Example 17

4-Hydroxy-6-(4-hydroxyphenyl)-3-[(phenylmethyl) thio]-2H-pyran-2-one

The title compound was prepared by Method A using 4'-hydroxyacetophenone (0.722 g, 5.31 mmol), lithium bis (trimethylsilyl)amide (1.95 g, 11.6 mmol), chlorotrimethylsilane (1.48 mL, 11.6 mmol), THF (116 mL), and diethyl ester of [(phenylmethyl)thio]propanedioic acid (1.00 g, 3.54 mmol). m.p. dec. 204° C.; $^1$H NMR (250 MHz, DMSO-$d_6$) δ3.96 (s, 2 H), 6.55 (s, 1 H), 6.88 (d, 2 H), 7.39 (m, 5 H), 7.63 (d, 2 H), 10.28 (s, 1 H), 11.75 (bs, 1 H).

Example 18

4-Hydroxy-6-(4-methoxyphenyl)-3-[(phenylmethyl) thio]-2H-pyran-2-one

The title compound was prepared by Method A using 4'-methoxyacetophenone (0.797 g, 5.31 mmol), lithium bis (trimethylsilyl)amide (0.977 g, 5.84 mmol), chlorotrimethylsilane (0.741 mL, 5.84 mmol), THF (58 mL), and diethyl ester of [(phenylmethyl)thio]propanedioic acid (1.00 g, 3.54 mmol). m.p. dec. 187° C.; $^1$H NMR (400 MHz, DMSO-$d_6$) δ3.83 (s, 3 H), 3.98 (s, 2 H), 6.62 (s, 1 H), 7.06 (m, 2 H), 7.22 (m, 5 H), 7.73 (m, 2 H), 11.76 (bs, 1 H).

Example 19

4-Hydroxy-6-(4-methylphenyl)-3-[(phenylmethyl) thio]-2H-pyran-2-one

The title compound was prepared by Method A using 4'-methylacetophenone (0.712 g, 5.31 mmol), lithium bis (trimethylsilyl)amide (0.977 g, 5.84 mmol), chlorotrimethylsilane (0.741 mL, 5.84 mmol), THF (58 mL), and diethyl ester of [(phenylmethyl)thio]-propanedioic acid (1.00 g, 3.54 mmol). m.p. dec. 205° C.; $^1$H NMR (400 MHz, DMSO-$d_6$) δ2.37 (s, 3 H), 3.99 (s, 2 H), 6.69 (s, 1 H), 7.26 (m, 7 H), 7.68 (m, 2 H), 11.83 (bs, 1 H).

Example 20

3-[Bis(phenylmethyl)amino]-4-hydroxy-6-phenyl-2H-pyran-2-one

The title compound was prepared by Method D using 3-amino-4-hydroxy-6-phenyl-2H-pyran-2-one hydrochloride (0.150 g, 0.626 mmol), 1% acetic acid in dimethylformamide (7 mL), benzaldehyde (0.133 mL, 1.33 mmol), sodium cyanoborohydride (0.083 g, 1.31 mmol). m.p. 130–135° C.; $^1$H NMR (400 MHz, DMSO-$d_6$) δ4.26 (s, 4 H), 6.44 (s, 1 H), 7.24 (m, 6 H), 7.44 (m, 7 H), 7.69 (m, 2 H).

Example 21

4-Hydroxy-6-phenyl-3-[(2-phenylethyl)thio]-2H-pyran-2-one

The title compound was prepared by Method B using 4-hydroxy-6-phenyl-2H-pyran-2-one (0.500 g, 2.65 mmol), ethanol (7 mL), 1N sodium hydroxide (2.65 mL), 2-phenylethyl-p-toluenethiosulfonate (0.770 g, 2.65 mmol). m.p. 121–124° C.; $^1$H NMR (400 MHz, DMSO-$d_6$) δ2.78 (t, 2 H), 2.99 (t, 2 H), 6.80 (s, 1 H), 7.24 (m, 5 H), 7.54 (m, 3 H), 7.80 (m, 2 H).

Example 22

4-Hydroxy-6-phenyl-3-[(3-phenylpropyl)thio]-2H-pyran-2-one

The title compound was prepared by Method A using 1-Phenyl-1-(trimethylsilyloxy)ethylene (0.922 g, 4.83 mmol) and diethyl ester of [(3-phenylpropyl)thio] propanedioic acid (1.00 g, 3.22 mmol). m.p. 114–116° C.; $^1$H NMR (400 MHz, DMSO-$d_6$) δ1.74 (m, 2 H), 2.71 (m, 4 H), 6.82 (m, 1 H), 7.16 (m, 3 H), 7.25 (m, 2 H), 7.54 (m, 3 H), 7.81 (m, 2 H), 11.95 (bs, 1 H).

Example 23

4-Hydroxy-3-[(2-phenoxyethyl)thio]-6-phenyl-2H-pyran-2-one

The title compound was prepared by Method B using 4-hydroxy-6-phenyl-2H-pyran-2-one (0.500 g, 2.65 mmol), ethanol (7 mL), 1N sodium hydroxide (2.65 mL, 2.65 mmol), 2-phenoxyethyl-p-toluenethiosulfonate (0.816 g, 2.65 mmol). m.p. 146–149° C.; $^1$H NMR (400 MHz, DMSO-$d_6$) δ3.12 (t, 2 H), 4.11 (t, 2 H), 6.81 (s, 1 H), 6.88 (m, 3 H), 7.24 (m, 2 H), 7.54 (m, 3 H), 7.81 (m, 2 H), 12.04 (bs, 1 H).

Example 24

4-Hydroxy-6-(2-methylphenyl)-3-[(phenylmethyl) thio]-2H-pyran-2-one

The title compound was prepared by Method A using 2'-methylacetophenone (0.712 g, 5.31 mmol), lithium bis (trimethylsilyl)amide (0.977 g, 5.84 mmol), chlorotrimethylsilane (0.741 mL, 5.84 mmol), THF (58 mL), and diethyl ester of [(phenylmethyl)thio]propanedioic acid (1.00 g, 3.54 mmol). $^1$H NMR (400 MHz, DMSO-$d_6$) δ2.34 (s, 3 H), 4.01 (s, 2 H), 6.32 (s, 1 H), 7.32 (m, 9H).

Example 25

4-Hydroxy-6-(2-phenylethyl)-3-[(phenylmethyl) thio]-2H-pyran-2-one

The title compound was prepared by Method A using 4-phenethylacetophenone (0.786 g, 5.31 mmol), lithium bis(trimethylsilyl)amide (0.977 g, 5.84 mmol), chlorotrimethylsilane (0.741 mL, 5.84 mmol), THF (58 mL), and diethyl ester of [(phenylmethyl)thio]propanedioic acid (1.00 g, 3.54 mmol). m.p. 164–166° C.; $^1$H NMR (400 MHz, DMSO-$d_6$) δ2.75 (t, 3 H), 2.85 (t, 2 H), 3.92 (s, 2 H), 5.92 (s, 1 H), 7.23 (m, 9H), 11.69 (bs, 1 H).

Example 26

4-Hydroxy-6-(3-hydroxyphenyl)-3-[(phenylmethyl) thio]-2H-pyran-2-one

The title compound was prepared by Method A using 3'-hydroxyacetophenone (0.722 g, 5.31 mmol), lithium bis (trimethylsilyl)amide (1.95 g, 11.6 mmol), chlorotrimethylsilane (1.48 mL, 11.6 mmol), THF (116 mL), and diethyl ester of [(phenylmethyl)thio]propanedioic acid (1.00 g, 3.54 mmol). m.p. dec. 185° C.; $^1$H NMR (400 MHz, DMSO-$d_6$) δ4.00 (s, 2 H), 6.66 (s, 1 H), 6.92 (m, 1 H), 7.21 (m, 7 H), 7.32 (m, 1 H).

Example 27

4-Hydroxy-6-(4-hydroxyphenyl)-3-[(phenylethyl) thio]-2H-pyran-2-one

The title compound was prepared by Method A using 4'-hydroxyacetophenone (0.688 g, 5.06 mmol), lithium bis (trimethylsilyl)amide (1.84 g, 11.1 mmol), chlorotrimethylsilane (1.41 mL, 11.1 mmol), THF (111 mL), and diethyl ester of [(2-phenylethyl)thio]propanedioic acid (1.00 g, 3.37 mmol). $^1$H NMR (400 MHz, DMSO-$d_6$) δ2.78 (t, 2 H), 2.95 (t, 2 H), 6.62 (s, 1 H), 6.89 (dd, 2 H), 7.21 (m, 5 H), 7.65 (d, 2 H), 10.22 (s, 1 H), 11.05 (bs, 1 H).

Example 28

4-Hydroxy-6-phenyl-3-[3-(phenyl-2-propenyl)thio]-2H-pyran-2-one, (E)

The title compound was prepared by Method B using 4-hydroxy-6-phenyl-2H-pyran-2-one (0.500 g, 2.65 mmol), ethanol (7 mL), 1N sodium hydroxide (2.65 mL), 3-phenyl-2-propenyl-p-toluenethiosulfonate (0.808 g, 2.65 mmol). m.p. 133–136° C.; $^1$H NMR (400 MHz, DMSO-$d_6$) δ3.57 (d, 2 H), 6.24 (dt, 2 H), 6.76 (s, 1 H), 7.24 (m, 5 H), 7.51 (m, 3 H), 7.78 (m, 2 H).

Example 29

4-Hydroxy-3-[(2-phenylethyl)thio]-6-[4-(phenylmethoxy)phenyl]-2H-pyran-2-one

The title compound was prepared by Method A using 4'-benzyloxyacetophenone (1.14 g, 5.06 mmol), lithium bis(trimethylsilyl)amide (0.930 g, 5.56 mmol), chlorotrimethylsilane (0.705 mL, 5.56 mmol), THF (57 mL), and diethyl ester of [(2-phenylethyl)thio]propanedioic acid (1.00 g, 3.37 mmol). m.p. 139–142° C.; $^1$H NMR (400 MHz, DMSO-$d_6$) δ2.77 (t, 2 H), 2.98 (t, 2 H), 5.19 (s, 2 H), 6.68 (s, 1 H), 7.26 (m, 7 H), 7.43 (m, 5 H), 7.76 (d, 2 H).

Example 30

4-Hydroxy-6-[4-(2-phenylethoxy)phenyl]-3-[(2-phenylethyl)thio]-2H-pyran-2-one

The title compound was prepared by Method A using 4'-(2-phenylethoxy)acetophenone (1.21 g, 5.06 mmol), lithium bis(trimethylsilyl)amide (0.930 g, 5.56 mmol), chlorotrimethylsilane (0.705 mL, 5.56 mmol), THF (57 mL), and diethyl ester of [(2-phenylethyl)thio]propanedioic acid (1.00 g, 3.37 mmol). m.p. 103–106° C.; $^1$H NMR (400 MHz, DMSO-$d_6$) δ2.76 (t, 2 H), 2.97 (t, 2 H), 3.06 (t, 2 H), 4.27 (t, 2 H), 6.67 (s, 1 H), 7.21 (m, 12 H), 7.73 (d, 2 H).

Example 31

4-Hydroxy-3-[(2-phenylethyl)thio]-6-[4-(3-phenylpropoxy)phenyl]-2H-pyran-2-one

The title compound was prepared by Method A using 4'-(3-phenylpropoxy)acetophenone (1.28 g, 5.06 mmol), lithium bis(trimethylsilyl)amide (0.930 g, 5.56 mmol), chlorotrimethylsilane (0.705 mL, 5.56 mmol), THF (57 mL), and diethyl ester of [( 2-phenylethyl)thio]propanedioic acid (1.00 g, 3.37 mmol). m.p. 139–142° C.; $^1$H NMR (400 MHz, DMSO-$d_6$) δ2.04 (m, 2 H), 2.84 (m, 4 H), 2.98 (t, 2 H), 4.40 (t, 2 H), 6.68 (s, 1 H), 7.18 (m, 12 H), 7.75 (d, 2 H), 11.86 (bs, 1 H).

Example 32

4-Hydroxy-6-(2-hydroxyphenyl)-3-[(phenylmethyl) thio]-2H-pyran-2-one

The title compound was prepared by Method A using 2'-hydroxyacetophenone (0.722 g, 5.31 mmol), lithium bis (trimethylsilyl)amide (1.95 g, 11.6 mmol), chlorotrimethylsilane (1.48 mL, 11.6 mmol), THF (116 ml), and diethyl ester of [(phenylmethyl)thio]propanedioic acid (1.00 g, 3.54 mmol). m.p. dec. 189° C.; $^1$H NMR (400 MHz, DMSO-$d_6$) δ4.01 (s, 2 H), 6.97 (s, 1 H), 7.25 (m, 7 H), 7.71 (d, 1 H), 10.75 (s, 1 H), 11.85 (bs, 1 H).

Example 33

4-Hydroxy-6-[3-(2-phenylethoxy)phenyl]-3-[(2-phenylethyl)thio]-2H-pyran-2-one

The title compound was prepared by Method A using 3'-(2-phenylethoxy)acetophenone (0.336 g, 1.40 mmol), lithium bis(trimethylsilyl)amide (0.257 g, 1.54 mmol), chlorotrimethylsilane (0.195 mL, 1.54 mmol), THF (15 mL), and diethyl ester of [(2-phenylethyl)thio]-propanedioic acid (0.417 g, 1.40 mmol). m.p. 104–106° C.; $^1$H NMR (400 MHz, DMSO-$d_6$) δ2.75 (t, 2 H), 2.97 (t, 2 H), 3.04 (t, 2 H), 4.25 (t, 2 H), 6.79 (s, 1 H), 7.25 (m, 14H), 11.95 (bs, 1 H).

Example 34

4-Hydroxy-6-phenyl-3-[phenyl(phenylthio)methyl]-2H-pyran-2-one, (±)

The title compound was prepared by Method E using 4-hydroxy-6-phenyl-2H-pyran-2-one (1.00 g, 5.31 mmol), ethanol (10 mL), benzaldehyde (0.593 mL, 5.84 mmol), thiophenol (1.40 mL, 13.8 mmol), piperdine (0.5 mL), acetic acid (0.5 mL). m.p. dec. >220° C.; $^1$H NMR (400 MHz, DMSO-$d_6$) δ5.80 (s, 1 H), 6.70 (s, 1 H), 7.23 (m, 8H), 7.54 (m, 4 H), 7.74 (m, 2 H).

Example 35

4-Hydroxy-3-[[2-(2-methoxyphenyl)ethyl]thio]-6-phenyl-2H-pyran-2-one

The title compound was prepared by Method B using 4-hydroxy-6-phenyl-2H-pyran-2-one (0.500 g, 2.65 mmol), ethanol (7 mL), 1N sodium hydroxide (2.65 mL), 2-(2-methoxyphenyl)ethyl p-toluenethiosulfonate (0.856 g, 2.65 mmol). m.p. 114–115° C.; $^1$H NMR (400 MHz, DMSO-$d_6$) δ2.74 (t, 2 H), 2.94 (t, 2 H), 3.73 (s, 1 H), 6.85 (m, 3 H), 7.15 (m, 2 H), 7.54 (m, 3 H), 7.82 (m, 2 H).

Example 36

4-Hydroxy-6-phenyl-3-[(4-phenylbutyl)thio]-2H-pyran-2-one

The title compound was prepared by Method B using 4-hydroxy-6-phenyl-2H-pyran-2-one (0.500 g, 2.65 mmol), ethanol (7 mL), 1N sodium hydroxide (2.65 mL), 4-phenylbutyl-p-toluenethiosulfonate (0.851 g, 2.65 mmol). m.p. 103–105° C.; $^1$H NMR (400 MHz, DMSO-$d_6$) δ1.47 (m, 2 H), 1.66 (m, 2 H), 2.54 (t, 2 H), 2.77 (t, 2 H), 6.80 (s, 1 H), 7.17 (m, 5 H), 7.53 (m, 3 H), 7.81 (m, 2 H).

Example 37

4-Hydroxy-3-[[2-(3-methoxyphenyl)ethyl]thio]-6-phenyl-2H-pyran-2-one

The title compound was prepared by Method B using 4-hydroxy-6-phenyl-2H-pyran-2-one (0.500 g, 2.65 mmol), ethanol (7 mL), 1N sodium hydroxide (2.65 mL), 2-(3-methoxyphenyl)ethyl-p-toluenethiosulfonate (0.856 g, 2.65 mmol). m.p. 112–113° C.; $^1$H NMR (400 MHz, DMSO-$d_6$) δ2.75 (t, 2 H), 3.01 (t, 2 H), 3.34 (s, 3 H), 6.75 (s, 1 H), 7.16 (t, 1 H), 7.54 (m, 3 H), 7.80 (m, 2 H).

Example 38

4-Hydroxy-3-[[2-(4-methoxyphenyl)ethyl]thio]-6-phenyl-2H-pyran-2-one

The title compound was prepared by Method B using 4-hydroxy-6-phenyl-2H-pyran-2-one (0.500 g, 2.65 mmol), ethanol (7 mL), 1N sodium hydroxide (2.65 mL), 2-(4-methoxyphenyl)ethyl-p-toluenethiosulfonate (0.856 g, 2.65 mmol). m.p. 144–145° C.; $^1$H NMR (400 MHz, DMSO-$d_6$) δ2.71 (t, 2 H), 2.96 (t, 2 H), 3.66 (s, 3 H), 6.77 (s, 1 H), 6.80 (d, 2 H), 7.12 (d, 2 H), 7.54 (m, 3 H), 7.80 (m, 2 H).

Example 39

3-[[2-(3-Chlorophenyl)ethyl]thio]-4-hydroxy-6-phenyl-2H-pyran-2-one

The title compound was prepared by Method B using 4-hydroxy-6-phenyl-2H-pyran-2-one (0.500 g, 2.65 mmol), ethanol (7 mL), 1N sodium hydroxide (2.65 mL), 2-(2-chlorophenyl)ethyl-p-toluenethiosulfonate (0.868 g, 2.65 mmol). m.p. 133–134° C.; $^1$H NMR (400 MHz, DMSO-$d_6$) δ2.79 (t, 2 H), 3.02 (t, 2 H), 6.77 (s, 1 H), 7.25 (m, 4 H), 7.55 (m, 3 H), 7.81 (m, 2 H).

Example 40

4-Hydroxy-6-phenyl-3-(2-phenylethyl)-2H-pyran-2-one

The title compound was prepared by Method F using Raney-Nickel (Grace 3100), ethanol (20 mL), 4-hydroxy-6-phenyl-3-[2-phenyl-1-(phenylthio)ethyl]-2H-pyran-2-one (0.425 g, 1.06 mmol). m.p. dec. >255° C.; $^1$H NMR (400 MHz, DMSO-$d_6$) δ2.65 (dd, 2 H), 2.71 (dd, 2 H), 6.68 (s, 1 H), 7.23 (m, 3 H), 7.52 (m, 3 H), 7.76 (m, 2 H), 11.85 (bs, 1 H).

Example 41

4-Hydroxy-6-phenyl-3-(3-phenylpropyl)-2H-pyran-2-one

The title compound was prepared by Method F using Raney-Nickel (Grace 3100), ethanol (15 mL), 4-hydroxy-6-phenyl-3-[3-phenyl-1-(phenylthio)propyl]-2H-pyran-2-one (0.150 g, 0.362 mmol). m.p. 195–196° C.; $^1$H NMR (400 MHz, DMSO-$d_6$) δ1.73 (m, 2 H), 2.40 (t, 2 H), 2.60 (t, 2 H), 6.68 (s, 1 H), 7.23 (m, 5 H), 7.52 (m, 3 H), 7.74 (m, 2 H).

Example 42

6-(2,6-Dimethylphenyl)-4-hydroxy-3-[(phenylmethyl)thio]-2H-pyran-2-one

The title compound was prepared by Method A using 2',6'-dimethyl acetophenone (0.785 g, 5.31 mmol), lithium bis(trimethylsilyl)amide (0.977 g, 5.84 mmol), chlorotrimethylsilane (0.741 mL, 5.84 mmol), THF (58 mL), and diethyl ester of [(phenylmethyl)thio]propanedioic acid (1.00 g, 3.54 mmol). m.p. 140–143° C.; $^1$H NMR (400 MHz, DMSO-$d_6$) δ2.15 (s, 6 H), 3.99 (s, 2 H), 6.12 (s, 1 H), 7.22 (m, 8H).

Example 43

4-Hydroxy-6-[2-hydroxy-3-methyl-4-(phenylmethoxy) phenyl]-3-[(2-phenylethyl)thio]-2H-pyran-2-one The title compound was prepared by Method A using 4'-benzyloxy-2'-hydroxy-3'-methylacetophenone (1.29 g, 5.06 mmol), lithium bis(trimethylsilyl)amide (2.11 g, 12.6 mmol), chlorotrimethylsilane (1.60 mL, 12.6 mmol), THF (127 mL), and diethyl ester of [(2-phenylethyl)thio] propanedioic acid (1.00 g, 3.37 mmol). m.p. 147–148° C.; $^1$H NMR (400 MHz, DMSO-$d_6$) δ2.14 (s, 3 H), 2.77 (t, 2 H), 2.98 (t, 2 H), 5.17 (s, 2 H), 5.29 (s, 1 H), 6.79 (d, 1 H), 7.30 (m, 13H), 9.36 (s, 1 H), 11.85 (bs, 1 H).

Example 44

4-Hydroxy-3-[(2-phenylethyl)thio]-6-[3-(phenylmethoxy)phenyl]-2H-pyran-2-one

The title compound was prepared by Method A using 3'-benzyloxyacetophenone (1.14 g, 5.06 mmol), lithium bis(trimethylsilyl) amide (0.930 g, 5.56 mmol), chlorotrimethylsilane (0.705 mL, 5.56 mmol), THF (57 mL), and diethyl ester of [(2-phenylethyl)thio]propanedioic acid (1.00 g, 3.37 mmol). m.p. 126–127° C.; $^1$H NMR (400 MHz, DMSO-$d_6$) δ2.78 (t, 2 H), 3.01 (t, 2 H), 5.20 (s, 2 H), 6.81 (s, 1 H), 7.22 (m, 6 H), 7.41 (m, 7 H).

Example 45

4-Hydroxy-6-[-4-(2-naphthalenylmethoxy)phenyl]-3-[(2-phenylethyl)thio]-2H-pyran-2-one The title compound was prepared by Method A using 4'-(2-naphthalenylmethoxy)acetophenone (1.39 g, 5.06 mmol), lithium bis(trimethylsilyl)amide (0.930 g, 5.56 mmol), chlorotrimethylsilane (0.705 mL, 5.56 mmol), THF (57 mL), and diethyl ester of [(2-phenylethyl)thio] propanedioic acid (1.00 g, 3.37 mmol). m.p. 152–154° C.; $^1$H NMR (400 MHz, DMSO-$d_6$) δ2.77 (t, 2 H), 2.98 (t, 2 H), 5.38 (s, 2 H), 6.68 (s, 1 H), 7.21 (m, 7 H), 7.54 (m, 2 H), 7.60 (d, 1 H), 7.96 (m, 4 H).

Example 46

6-(3-Chloro-4-methoxyphenyl)-4-hydroxy-3-[(phenylmethyl)thio]-2H-pyran-2-one

The title compound was prepared by Method A using 3'-chloro-4'-methoxy acetophenone (0.979 g, 5.31 mmol), lithium bis(trimethylsilyl)amide (0.977 g, 5.84 mmol), chlorotrimethylsilane (0.741 mL, 5.84 mmol), THF (58 mL), and diethyl ester of [(phenylmethyl)thio]propanedioic acid (1.00 g, 3.54 mmol). m.p. dec. 171° C.; $^1$H NMR (400 MHz, DMSO-$d_6$) δ3.93 (s, 3 H), 3.99 (s, 2 H), 6.68 (s, 1 H), 7.32 (m, 6 H), 7.77 (d, 1 H), 7.83 (d, 1 H).

Example 47

4-Hydroxy-6-phenyl-3-[(phenylmethyl)sulfonyl]-2H-pyran-2-one

This compound was prepared by oxidation of 4-hydroxy-6-phenyl-3-[(phenylmethyl)thio]-2H-Pyran-2-one (1 mmol, 310 mg) with oxone (3 mmol, 1.99 g) at room temperature in 10 mL of methanol and 10 mL of water. After stirring the reaction mixture at room temperature for 4 hours the mixture was diluted with water and extracted with 50 mL of dichloromethane. The organic layer was dried over anhydrous magnesium sulfate. Solvents were evaporated. The residual, a solid was pure by tlc. Isolated yield: 90%. m.p. 152–153° C. $^1$H NMR (400 MHz, $CDCl_3$) δ11.34 (s, 1 H), 7.8 (m, 2 H), 7.5 (m, 3 H), 7.37 (m, 3 H), 7.27 (m, 2 H), 6.37 (s, 1 H), 6.23 (s, 1 H), 4.75 (s, 1 H), 4.34 (q, 2 H); IR (KBr) 3421, 3059, 1726, 1698, 1628, 1559, 1497, 1230, 957, 770, 689 $cm^{-1}$; MS (CI) m/e 343 (6.8), 327 (15.54), 278 (15.99), 219 (40.99), 91 (100).

Example 48

4-Hydroxy-6-(3-methylphenyl)-3-[(phenylmethyl)thio]-2H-pyran-2-one

This compound was prepared by the condensation of the diethyl ester of [(phenylmethyl)thio]-propanedioic acid (1 g, 3.54 mmol) with the corresponding trimethylsilyl enol ether of 3'-methyl acetophenone (7.09 mmol, 1.46 g) as described in general procedure A. Isolated Yield: 65% m.p. 137–138° C. $^1$H NMR (400 MHz, DMSO-d6) δ11.9 (brs, 1 H), 7.6 (m, 2 H), 7.39 (t, 1 H), 7.35 (d, 1 H), 7.25 (d, 4 H), 7.2 (m, 1 H), 6.7 (s, 1 H), 4.0 (s, 2 H), 2.38 (s, 3 H); IR (KBr) 3030, 2585, 1617, 1536, 1402, 1100, 787, 696 cm−1; MS (CI) m/e 325 (65), 291 (2), 233 (4), 119 (9), 91 (100).

Example 49

2-Oxo-6-phenyl-3-[(phenylmethyl)thio]-2H-pyran-4-ylpropanoic acid ester

This compound was prepared by the treatment of sodium salt of 4-hydroxy-6-phenyl-3-[(phenylmethyl)thio]-2H-pyran-2-one (310 mg, 1 mmol) with propionyl chloride (2.4 mmol, 222 mg) as described in the general procedure G. Isolated Yield: 72%.: 1H NMR (400 MHz, DMSO-d6) d 7.77 (m, 2 H), 7.51. m (3), 7.22 (m, 4 H), 7.17 (m, 1 H), 6.7 (s, 1 H), 3.98 (s, 2 H), 2.19 (q, 2 H), 0.96 (t, 3 H); IR (KBr) 3438, 3027, 2923, 1772, 1731, 1617, 1528, 1494, 1453, 1323, 1153, 1087, 1045, 979, 873, 767, 702 cm−1; MS (CI) m/e 366 (4), 311 (79), 189 (26), 105 (20), 91 (100).

Example 50

4-Hydroxy-6-[3-methyl-4-(phenylmethyloxy)phenyl]-3-[(2-phenylethyl)thio]-2H-pyran-2-one Condensation of diethylester of [(phenylethyl)thio] propanedioic acid (1.06 g, 3.6 mmol) with the trimethylsilyl enol ether of 3'-methoxy-4'-benzyloxyacetophenone (2.24 g, 7.2 mmol) was performed as described in general procedure A. Isolated yield; 78%. m.p. 147–148° C.: $^1$H NMR (400 MHz, DMSO-d6) δ7.63 (m, 2 H), 7.11–7.53 (m, 11H), 6.68 (s, 1 H), 5.22 (s, 1 H), 2.98 (t, 2 H), 2.77 (t, 2 H), 2.27 (s, 3 H); IR (KBr) 3432, 3030, 2922, 1717, 1626, 1503, 1408, 1262, 1140, 1024, 696 cm−1; MS (CI) m/e 445 (2.12), 3553.34, 309 (3.81), 189 (8.33), 156 (14.78), 137 (16.19), 105 (94.34), 91 (100); Analysis calc'd for: C, 72.95; H, 5.44; found: C, 72.25; H, 5.43.

Example 51

4-Hydroxy-6-(4-hydroxy-2-methylphenyl)-3-[2-phenylethyl)thio]-2H-pyran-2-one

This compound is prepared by the condensation of diethyl ester of [(phenylethyl)thio]propanedioic acid (1 g, 3.38 mmol) with the corresponding trimethylsilyl enol ether of 4'-hydroxy-2'-methyl acetophenone (2.94 g, 10 mmol) as described in the general procedure A. Isolated yield: 52% m.p. 85–87° C. $^1$H NMR (400 MHz, DMSO-d6) δ11.89 (brs, 1 H), 9.97 (s, 1 H), 7.35 (d, 1 H), 7.23 (m, 5 H), 6.72 (s, 2 H), 6.33 (s, 1 H), 3.0 (t, 2 H), 2.78 (t, 2 H), 2.34 (s, 3 H); IR (KBr) 3300, 2926, 1672, 1604, 1541, 1244, 1194, 1120, 698 cm−1; MS (CI) m/e 355 (36), 250 (27), 105 (93), 91 (30), 85 (100); Analysis calc'd for: C, 67.78; H, 5.12; found: C, 67.53; H, 5.40.

Example 52

4-Hydroxy-6-(4-methoxy-3-methylphenyl)-3-[(phenylmethyl)thio]-2H-pyran-2-one

This compound is prepared by the condensation of diethyl ester of [(phenylmethyl)thio]propanedioic acid (1 g, mmol) with the corresponding trimethylsilylenol ether of 4'-methoxy-3'-methylacetophenone as described in general procedure A. Isolated Yield: 68%. m.p. 159–106° C. $^1$H NMR (400 MHz, CDCl3) δ7.67 (dd, 1 H), 7.61 (s, 1 H), 7.2 (m, 5 H), 6.8 (d, 1 H), 6.38 (s, 1 H), 3.96 (s, 2 H), 3.89 (s, 3 H), 2.25 (s, 3 H); IR (KBr) 3432, 2945, 1613, 1507, 1402, 1262, 1142, 1030, 812, 704 cm−1; MS (CI) m/e 355 (78.3), 263 (19.6), 235 (11.8), 149 (12.7), 91 (100); Analysis calc'd for: C, 67.78; H, 5.12; found: C, 67.35; H, 5.17.

Example 53

2-Oxo-6-phenyl-3-[(phenylmethyl)thio]-2H-pyran-4-ylacetic acid ester

This compound was prepared by the treatment of sodium salt of 4-hydroxy-6-phenyl-3-[(phenylmethyl)thio]-2H-pyran-2-one, (310 mg, 1.00 mmol) with acetyl chloride (188 mg, 2.4 mmol) as described in general procedure G. Isolated yield: 72%. $^1$H NMR (400 MHz, DMSO-$d^6$) δ7.81 (m, 2 H), 7.53 (m, 3 H), 7.22 (m, 4 H), 7.16 (m, 1 H), 3.99 (s, 2 H), 1.92 (s, 3 H).

Example 54

2-Oxo-6-phenyl-2H-pyran-4-yl-1-naphthalenecarboxylic acid ester

This compound was prepared by Method G using 4-hydroxy-6-phenyl-2H-pyran-2-one (0.250 g, 1.32 mmol), THF (15 mL), 60% sodium hydride (0.585 g, 1.46 mmol), 1-naphthoyl chloride (0.278 g, 1.46 mmol). m.p. 123.5–125; $^{1}$H NMR (250 MHz, DMSO-$d_6$) δ6.54 (s, 1 H), 7.49 (s, 1 H), 7.65 (m, 6 H), 7.95 (m, 2 H), 8.13 (d, 1 H), 8.34 (d, 1 H), 8.50 (d, 1 H).

Example 55

3,3'-Thiobis[4-hydroxy-6-phenyl-2H-pyran-2-one]

This compound was synthesized by the following method: 4-hydroxy-6-phenyl-2H-pyran-2-one (0.250 g, 1.33 mmol) was gradually added to thionyl chloride (0.585 ml). The reaction was allowed to stir at room temperature overnight. The unreacted thionyl chloride was removed in vacuo and residue was recrystallized from boiling methanol. m.p. >240° C.; $^{1}$H NMR (250 MHz, d-TFA) δ7.03 (s, 2 H), 7.56 (m, 6 H), 7.89 (m, 4 H).

Example 56

3,3'-Dithiobis[4-hydroxy-6-phenyl-2H-pyran-2-one]

Sulfur monochloride (0.105 mL, 1.32 mmol) was dissolved in benzene (1 ml), and the solution was added dropwise to a suspension of 4-hydroxy-6-phenyl-2H-pyran-2-one (0.500 g, 2.65 mmol) in benzene (7 ml) while the suspension was being refluxed. The reflux was continued for 1.5 hrs. The reaction was quenched with a few drops of water, and the light tan product was collected by filtration. The solid was recrystallization from boiling acetic acid. m.p. dec>280° C.; $^{1}$H NMR (250 MHz, DMSO-$d_6$) δ6.77 (s, 2 H), 7.52 (m, 6 H), 7.81 (m, 4 H).

Example 57

3-Benzoyl-4-hydroxy-6-phenyl-2H-pyran-2-one

To a solution of ethyl benzoylacetate (150 g, 0.88 mmol) in 1,2-dichlorobenzene (150 mL) was added a trace amount of sodium bicarbonate. The reaction mixture was heated to reflux. A distillate of ethanol (approximately 20 mL) was collected. The reaction mixture was cooled to 0° C. Ether (100 mL) was added to induce crystallization. The reaction mixture was kept in the refrigerator overnight. The solid formed was collected and washed with ether: m.p. 171–173° C.; $^{1}$H NMR (250 MHz, DMSO-$d_6$) δ6.91 (s, 1 H), 7.59 (m, 6 H), 7.87 (m, 4 H).

Example 58

N-(4-Hydroxy-2-oxo-6-phenyl-2H-pyran-3-yl)benzeneacetamide

The title compound was prepared by Method E using 3-amino-4-hydroxy-6-phenyl-2H-pyran-2-one hydrochloride (0.150 g, 0.626 mmol), methylene chloride (6 mL), triethylamine (0.348 mL, 2.50 mmol), catalytic 4-dimethylaminopyridine, phenacetyl chloride (0.106 g, 0.626 mmol). m.p. dec. 213° C.; $^{1}$H NMR (250 MHz, DMSO-$d_6$) δ3.69 (s, 2 H), 6.85 (s, 1 H), 7.29 (m, 4 H), 7.53 (m, 3 H), 7.83 (m, 2 H), 9.40 (bs, 1 H).

Example 59

2-oxo-6-phenyl-2H-pyran-4-yl-2-naphthalenecarboxylic acid ester

The title compound was prepared by Method G using 4-hydroxy-6-phenyl-2H-pyran-2-one (0.200 g, 0.835 mmol), methylene chloride (8 mL), triethylamine (0.348 mL, 2.50 mmol), catalytic 4-dimethylaminopyridine, 2-naphthoyl chloride (0.175 g, 0.918 mmol). m.p. 143.5–144° C.; $^{1}$H NMR (250 MHz, DMSO-$d_6$) δ6.51 (s, 1 H), 7.51 (m, 3 H), 7.72 (m, 3 H), 8.80 (m, 7 H), 8.89 (bs, 1 H).

Example 60

3-[Bis(2-naphthalenylmethyl)amino]-4-hydroxy-6-phenyl-2H-pyran-2-one

The title compound was prepared by Method D using 3-amino-4-hydroxy-6-phenyl-2H-pyran-2-one hydrochloride (0.250 g, 1.04 mmol), 1% acetic acid in dimethylformamide (10 mL), 2-naphthaldehyde (0.407 g, 2.60 mmol), sodium cyanoborohydride (0.164 g, 2.60 mmol). m.p. dec. 209; $^{1}$H NMR (250 MHz, DMSO-$d_6$) δ4.46 (s, 4 H), 6.38 (s, 1 H), 7.44 (m, 8H), 7.77 (m, 13H).

Example 61

N-(4-Hydroxy-2-oxo-6-phenyl-2H-pyran-3-yl)-2-naphthaleneacetamide

The title compound was prepared by Method E using 3-amino-4-hydroxy-6-phenyl-2H-pyran-2-one hydrochloride (0.200 g, 0.835 mmol), THF (9 mL), 60% sodium hydride (0.037 mL, 0.918 mmol), oxalyl chloride (0.080 mL, 0.918 mmol), 2-naphthalyl acetic acid (0.170 g, 0.918 mmol). m.p. dec. 227° C.; $^{1}$H NMR (250 MHz, DMSO-$d_6$) δ4.17 (s, 2 H), 6.84 (s, 1 H), 7.50 (m, 6 H), 7.83 (m, 4 H), 7.93 (d, 1 H), 8.17 (d, 1 H), 9.58 (s, 1 H).

Example 62

N-(4-Hydroxy-2-oxo-6-phenyl-2H-pyran-3-yl)-2-naphthalenecarboxamide

The title compound was prepared by Method E using 3-amino-4-hydroxy-6-phenyl-2H-pyran-2-one hydrochloride (0.150 g, 0.626 mmol),, THF (6 mL), 60% sodium hydride (0.028 mL, 0.688 mmol), 2-naphthoyl chloride (0.131 g, 0.688 mmol). m.p. dec. 219° C.; $^{1}$H NMR (250 MHz, DMSO-$d_6$) δ6.92 (s, 1 H), 7.61 (m, 5 H), 7.97 (m, 6 H), 8.62 (s, 1 H), 9.61 (s, 1 H).

Example 63

N-(4-Hydroxy-2-oxo-6-phenyl-2H-pyran-3-yl)benzenepropanamide

The title compound was prepared by Method E using 3-amino-4-hydroxy-6-phenyl-2H-pyran-2-one hydrochloride (0.150 g, 0.626 mmol), THF (6 mL), 60% sodium hydride (0.028 mL, 0.688 mmol), hydrocinnamyl chloride (0.131 g, 0.688 mmol). m.p. 191–193° C.; $^{1}$H NMR (250 MHz, DMSO-$d_6$) δ2.65 (t, 2 H), 2.89 (t, 2 H), 6.86 (s, 1 H), 7.26 (m, 5 H), 7.53 (m, 3 H), 7.84 (m, 2 H), 9.28 (s, 1 H).

Example 64

6-(1,3-Benzodioxol-5-yl)-4-hydroxy-3-[(phenylmethyl)thio]-2H-pyran-2-one

The title compound was prepared by Method A using 3',4'-(methylenedioxy)acetophenone (0.871 g, 5.31 mmol), lithium bis(trimethylsilyl)amide (0.977 g, 5.84 mmol), chlorotrimethylsilane (0.741 mL, 5.84 mmol), THF (58 mL), and diethyl ester of [(phenylmethyl)thio] propanedioic acid (1.00 g, 3.54 mmol). m.p. dec. 170° C.; $^1$H NMR (400 MHz, DMSO-$d_6$) δ3.98 (s, 2 H), 6.13 (s, 2 H), 6.61 (s, 1 H), 7.05 (d, 2 H), 7.27 (m, 7 H).

Example 65

6-[4-(Benzoyloxy)phenyl]-4-hydroxy-3-[(phenylmethyl) thio]-2H-pyran-2-one

The title compound was prepared by Method A using 4'-benzoyloxyacetophenone (1.27 g, 5.31 mmol), lithium bis(trimethyl-silyl)amide (0.977 g, 5.84 mmol), chlorotrimethyl-silane (0.741 mL, 5.84 mmol), THF (58 mL), and diethyl ester of [(phenylmethyl)thio]propanedioic acid (1.00 g, 3.54. mmol). m.p. dec. 205° C.; $^1$H NMR (400 MHz, DMSO-$d_6$) δ4.01 (s, 2 H), 6.75 (s, 1 H), 7.21 (m, 1 H), 7.25 (d, 4 H), 7.47 (d, 2 H), 7.63 (t, 2 H), 7.77 (t, 1 H), 7.90 (d, 2 H), 8.16 (d, 2 H).

Example 66

3-[Cyclohexyl(phenylthio)methyl]-4-hydroxy-6-phenyl-2H-pyran-2-one

The title compound was prepared by Method C using 4-hydroxy-6-phenyl-2H-pyran-2-one (1.00 g, 5.31 mmol), ethanol (10 mL), cyclohexanecarboxaldehyde (0.707 mL, 5.84 mmol), thiophenol (1.40 mL, 13.8 mmol), piperdine (0.5 mL), acetic acid (0.5 mL). m.p. 87–90° C.; $^1$H NMR (400 MHz, DMSO-$d_6$) δ1.46 (m, 5 H), 1.61 (m, 4 H), 2.15 (m, 1 H), 2.31 (d, 1 H), 4.26 (d, 1 H), 6.65 (s, 1 H), 7.16 (t, 1 H), 7.27 (t, 2 H), 7.37 (d, 2 H), 7.52 (m, 3 H), 7.74 (m, 2 H), 11.80 (bs, 1 H).

Example 67

4-Hydroxy-3-[(2-phenylethyl)thio]-6-[4-(phenylthio) phenyl]-2H-pyran-2-one

The title compound was prepared by Method A using 4'-(phenylthio)acetophenone (1.15 g, 5.06 mmol), lithium bis(trimethylsilyl)amide (0.930 g, 5.56 mmol), chlorotrimethylsilane (0.705 mL, 5.56 mmol), THF (56 mL), and diethyl ester of [(2-phenylethyl)thio]propanedioic acid (1.00 g, 3.37 mmol). m.p. 120–121° C.; $^1$H NMR (400 MHz, DMSO-$d_6$) δ2.76 (t, 2 H), 2.98 (t, 2 H), 6.72 (s, 1 H), 7.24 (m, 7 H), 7.45 (m, 5 H), 7.74 (d, 2 H).

Example 68

4-Hydroxy-6-[4-[(2-methoxyphenyl)methoxy] phenyl]-3-[(2-phenylethyl)thio]-2H-pyran-2-one The title compound was prepared by Method A using 4'-[(2-methoxyphenyl)methoxy]phenylacetophenone (1.29 g, 5.06 mmol), lithium bis(trimethylsilyl)amide (0.930 g, 5.56 mmol), chlorotrimethylsilane (0.705 mL, 5.56 mmol), THF (56 mL), and diethyl ester of [(2-phenylethyl)thio] propanedioic acid (1.00 g, 3.37 mmol). m.p. 138–139° C.; $^1$H NMR (400 MHz, DMSO-$d_6$) δ2.77 (t, 2 H), 2.98 (t, 2 H), 3.83 (s, 3 H), 5.14 (s, 2 H), 6.68 (s, 1 H), 6.97 (t, 1 H), 7.08 (d, 1 H), 7.20 (m, 7 H), 7.53 (t, 1 H), 7.40 (d, 1 H), 7.76 (d, 2 H), 11.85 (bs, 1 H).

Example 69

4-Hydroxy-6-[4-[(2-methoxyphenyl)methoxy]-3-methylphenyl]-3-[(2-phenylethyl)thio]-2H-pyran-2-one The title compound was prepared by Method A using 4'-[(2-methoxyphenyl)methoxy]-3'-methylacetophenone (1.36 g, 5.06 mmol), lithium bis(trimethylsilyl)amide (0.930 g, 5.56 mmol), chlorotrimethylsilane (0.705 mL, 5.56 mmol), THF (56 mL), and diethyl ester of [(2-phenylethyl) thio]propanedioic acid (1.00 g, 3.37 mmol). m.p. dec. 170° C.; $^1$H NMR (400 MHz, DMSO-$d_6$) δ 2.25 (s, 3 H), 2.77 (t, 2 H), 2.97 (t, 2 H), 3.84 (s, 3 H), 5.17 (s, 2 H), 6.67 (s, 1 H), 6.98 (t, 1 H), 7.70 (d, 1 H), 7.27 (m, 6 H), 7.41 (t, 1 H), 7.43 (d, 1 H), 7.65 (m, 2 H), 11.81 (bs, 1 H).

Example 70

6-(3,5-Dimethylphenyl)-4-hydroxy-3-[(phenylmethyl)-thio]-2H-pyran-2-one

The title compound was prepared by Method A using 3',5'-dimethylacetophenone (0.785 g, 5.31 mmol), lithium bis(trimethylsilyl)amide (0.977 g, 5.84 mmol), chlorotrimethylsilane (0.741 mL, 5.84 mmol), THF (58 mL), and diethyl ester of [(phenylmethyl)thio]propanedioic acid (1.00 g, 3.54 mmol). m.p. dec. 170° C.; $^1$H NMR (400 MHz, DMSO-$d_6$) δ2.33 (s, 6 H), 3.99 (s, 2 H), 6.67 (s, 1 H), 7.21 (m, 6 H), 7.39 (s, 2 H).

Example 71

4-Hydroxy-6-(4-phenoxyphenyl)-3-[(2-phenylethyl) thio]-2H-pyran-2-one

The title compound was prepared by Method A using 4'-phenoxyacetophenone (1.07 g, 5.06 mmol), lithium bis (trimethylsilyl)amide (0.930 g, 5.56 mmol), chlorotrimethylsilane (0.705 mL, 5.56 mmol), THF (56 mL), and diethyl ester of [(2-phenylethyl)thio]propanedioic acid (1.00 g, 3.37 mmol). m.p. 127–128° C.; $^1$H NMR (400 MHz, DMSO-$d_6$) δ2.77 (t, 2 H), 2.99 (t, 2 H), 6.72 (s, 1 H), 7.18 (m, 10H), 7.46 (t, 2 H), 7.82 (d, 2 H).

Example 72

4-Hydroxy-6-phenyl-3-[[[4-(phenylmethoxy)phenyl] methyl]thio]-2H-pyran-2-one The title compound was prepared by Method B using 4-hydroxy-6-phenyl-2H-pyran-2-one (0.500 g, 2.65 mmol), ethanol (7 mL), 1N sodium hydroxide (2.65 mL), [4-(phenylmethoxy)phenyl]methyl-p-toluenethiosulfonate (1.01 g, 2.65 mmol). m.p. 185–186° C.; $^1$H NMR (400 MHz, DMSO-$d_6$) δ3.94 (s, 2 H), 5.03 (s, 2 H), 6.72 (s, 1 H) 6.89 (d, 2 H), 7.18 (d, 2 H), 7.34 (m, 5 H), 7.46 (m, 3 H), 7.80 (m, 3 H).

Example 73

4-Hydroxy-3-[(2-phenylethyl)thio]-6-[4-(2-pyridinylmethoxy)phenyl]-2H-pyran-2-one The title compound was prepared by Method A using 4'-(2-pyridinylmethoxy)acetophenone (1.14 g, 5.06 mmol), lithium bis(trimethylsilyl)amide (0.930 g, 5.56 mmol), chlorotrimethylsilane (0.705 mL, 5.56 mmol), THF (56 mL), and diethyl ester of [(2-phenylethyl)thio]propanedioic acid (1.00 g, 3.37 mmol). m.p. dec. 179° C.; $^1$H NMR (400 MHz, DMSO-$d_6$) δ2.77 (t, 2 H), 2.98 (t, 2 H), 5.27 (s, 2 H), 6.68 (s, 1 H), 7.22 (m, 7 H), 7.36 (m, 1 H), 7.53 (d, 1 H), 7.77 (d, 2 H), 7.85 (t, 1 H), 8.60 (d, 2 H), 11.88 (bs, 1 H).

Example 74

4-[4-Hydroxy-2-oxo-3-[(2-phenylethyl)thio]-2H-pyran-6-yl]phenoxy acetic acid ethyl ester To a methanol solution (3 ml) of the 4-hydroxy-6-(4-hydroxyphenyl)-3-[(2-phenylethyl)thio]-2H-pyran-2-one (0.500 g, 1.47 mmol) was added cesium carbonate (0.955 g, 2.94 mmol). The reaction was stirred for 3 hrs. and is then concentrated in vacuo. Next, dimethylformamide (15 mL) is added and the residue is reconcentrated in vacuo to dryness. The solid is then diluted with dimethylformamide (3 mL) and bromoethylacetate (0.491 mL, 2.94 mmol) is added. The slurry is then stirred for 3 hrs. The reaction is quenched by dilution with ethyl acetate (100 mL). The organic layer is washed in succession with; 1 N HCl, water, saturated sodium chloride; dried over anhydrous magnesium sulfate. After evaporation of the solvents in vacuo, the crude product was purified by flash column chromatography ($SiO_2$-230 to 400 mesh) using a gradient of 15% ethyl acetate/hexanes to 50% ethyl acetate/hexanes to 30% ethyl acetate/30% hexanes/40% methylene chloride.: m.p. 169–171° C.; $^1$H NMR (400 MHz, DMSO-$d_6$) δ1.20 (t, 3 H), 2.75 (t, 2 H), 2.96 (t, 2 H), 4.16 (q, 2 H), 4.87 (s, 2 H), 6.69 (s, 1 H), 7.06 (d, 2 H), 7.19 (m, 5 H), 7.73 (d, 2 H), 11.85 (bs, 1 H).

Example 75

4-Hydroxy-3-[2-naphthalenyl(phenylthio)methyl]-6-phenyl-2H-pyran-2-one

The title compound was prepared by Method C using 4-hydroxy-6-phenyl-2H-pyran-2-one (1.00 g, 5.31 mmol), ethanol (10 mL), 2-naphthaldehyde (0.912 g, 5.84 mmol), thiophenol (1.40 mL, 13.8 mmol), piperdine (0.5 mL), acetic acid (0.5 mL). m.p. 98–101° C.; $^1$H NMR (400 MHz, DMSO-$d_6$) δ5.96 (s, 1 H), 6.73 (s, 1 H), 7.18 (t, 1 H), 7.36 (m, 4 H), 7.52 (m, 5 H), 7.88 (m, 3 H), 8.07 (s, 1 H).

Example 76

4-Hydroxy-3-[(2-naphthalenylthio)phenylmethyl]-6-phenyl-2H-Pyran-2-one

The title compound was prepared by Method C using 4-hydroxy-6-phenyl-2H-pyran-2-one (1.00 g, 5.31 mmol), ethanol (10 mL), benzaldehyde (0.593 mL, 5.84 mmol), 2-naphthalenethiol (2.21 gL, 13.8 mmol), piperdine (0.5 mL), acetic acid (0.5 mL). m.p. dec. 200° C.; $^1$H NMR (400 MHz, DMSO-$d_6$) δ5.9 (s, 1 H), 6.71 (s, 1 H), 7.20 (m, 5 H), 7.44 (m, 7 H), 7.75 (m, 3 H), 7.82 (m, 2 H).

Example 77

4-[4-Hydroxy-2-oxo-3-[(2-phenylethyl)thio]-2H-pyran-6-yl]phenoxyacetic acid

To a tetrahydrofuran (10 ml) solution of 4-[4-hydroxy-2-oxo-3-[(2-phenylethyl)thio]-2H-pyran-6-yl]phenoxyacetic acid, ethyl ester (0.939 mmol) was added 1N sodium hydroxide (2.34 mmol). The reaction was stirred for 5 hrs, and then quenched by addition of water (10 ml) followed by acidification with conc. hydrochloric acid to pH 2. The aqueous layer was then extracted with 2× with ethyl acetate (100 ml). The combined organic extracts were then washed with saturated sodium chloride and dried over anhydrous magnesium sulfate. After evaporation of the solvents in vacuo, the crude product was purified by column chromatography (silica gel-230 to 400 mesh) using 94/5/1 methylene chloride/methanol/acetic acid as the eluent. m.p. 182–183° C.; $^1$H NMR (400 MHz, DMSO-$d_6$) δ2.76 (t, 2 H), 2.97 (t, 2 H), 4.78 (s, 2 H), 6.67 (s, 1 H), 7.06 (d, 2 H), 7.21 (m, 5 H), 7.75 (d, 2 H).

Example 78

4-Hydroxy-3-[(2-phenylethyl)thio]-6-[4-(3-pyridinylmethoxy)phenyl]-2H-pyran-2-one The title compound was prepared by Method A using 4'-(3-pyridinylmethoxy)acetophenone (1.14 g, 5.06 mmol), lithium bis(trimethylsilyl)amide (0.930 g, 5.56 mmol), chlorotrimethylsilane (0.705 mL, 5.56 mmol), THF (56 mL), and diethyl ester of [(2-phenylethyl)thio]propanedioic acid (1.00 g, 3.37 mmol). m.p. 178–179° C.; $^1$H NMR (400 MHz, DMSO-$d_6$) δ2.76 (t, 2 H), 2.98 (t, 2 H), 5.25 (s, 2 H), 6.69 (s, 1 H), 7.21 (m, 7 H), 7.45 (q, 1 H), 7.77 (d, 2 H), 7.91 (d, 1 H), 8.57 (bs, 1 H), 8.70 (bs, 1 H).

Example 79

6-[4-(Cyclohexylmethoxy)phenyl]-4-hydroxy-3-[(2-phenylethyl)thio]-2H-pyran-2-one The title compound was prepared by Method A using 4'-(cyclohexylmethoxy) acetophenone (2.50 g, 10.77 mmol), lithium bis(trimethylsilyl)amide (2.70 g, 16.16 mmol), chlorotrimethylsilane (2.05 mL,16.16 mmol), THF (107 mL), and diethyl ester of [(2-phenylethyl)thio] propanedioic acid (1.00 g, 3.37 mmol). m.p. 130–132° C.; $^1$H NMR (400 MHz, DMSO-$d_6$) δ 1.15 (m, 5 H), 1.81 (m, 6 H), 2.77 (t, 2 H), 2.97 (t, 2 H), 3.85 (d, 2 H), 6.67 (s, 1 H), 7.21 (m, 5 H), 7.45 (q, 1 H), 7.74 (d, 2 H).

Example 80

4-Hydroxy-3-[(2-phenylethyl)thio]-6-[4-(phenylsulfonyl)phenyl]-2H-pyran-2-one

The title compound was prepared by Method A using 4'-(phenylsulfonyl)acetophenone (2.50 g, 9.61 mmol), lithium bis(trimethylsilyl)amide (2.41 g, 14.42 mmol), chlorotrimethylsilane (1.83 mL, 14.42 mmol), THF (96 mL), and diethyl ester of [(2-phenylethyl)thio]propanedioic acid (1.00 g, 3.37 mmol). m.p. 194–195° C.; $^1$H NMR (400 MHz, DMSO-$d_6$) δ2.76 (t, 2 H), 3.01 (t, 2 H), 6.87 (s, 1 H), 7.19 (m, 5 H), 7.68 (m, 3 H), 8.04 (m, 6 H), 12.05 (bs, 1 H).

Example 81

4-Hydroxy-3-[(2-phenylethyl)thio]-6-[4-benzoyloxy) phenyl]-2H-pyran-2-one

The title compound was prepared by Method A using 4'-benzoyloxyacetophenone (2.50 g, 10.41 mmol), lithium bis(trimethylsilyl)amide (2.61 g, 15.62 mmol), chlorotrimethylsilane (1.98 mL, 15.62 mmol), THF (100 mL), and diethyl ester of [(2-phenylethyl)thio]propanedioic acid (1.00 g, 3.37 mmol). m.p. 164–166° C.; $^1$H NMR (400 MHz, DMSO-$d_6$) δ2.78 (t, 2 H), 3.01 (t, 2 H), 6.81 (s, 1 H), 7.21 (m, 5 H), 7.49 (d, 2 H), 7.63 (t, 2 H), 7.77 (t, 1 H), 7.92 (d, 2 H),12.00 (bs, 1 H)

Example 82

4-Hydroxy-3-[(2-phenylethyl)thio]-6-[4-(phenylsulfinyl)phenyl]-2H-pyran-2-one

The title compound was prepared by Method A using 4'-(phenylsulfinyl)acetophenone (2.50 g, 10.24 mmol), lithium bis(trimethylsilyl)amide (2.57 g,15.36 mmol), chlorotrimethylsilane (1.94 mL,15.36 mmol), THF (100 mL), and diethyl ester of [(2-phenylethyl)thio]-propanedioic acid (1.00 g, 3.37 mmol). m.p. 171–173° C.; $^1$H NMR (400 MHz, DMSO-$d_6$) δ2.76 (t, 2 H), 3.01 (t, 2 H), 6.83 (s, 1 H), 7.19 (m, 5 H), 7.54 (m, 3 H), 7.75 (d, 2 H), 7.86 (d, 2 H), 7.95 (d, 2 H), 12.05 (bs, 1 H).

Example 83

4-Hydroxy-3-[(2-phenylethyl)thio]-6-(4-pyridinyl)-2H-pyran-2-one

The title compound was prepared by Method A using 4-acetylpyridine (2.50 g, 20.63 mmol), lithium bis (trimethylsilyl)amide (5.17 g, 30.94 mmol), chlorotrimethylsilane (3.92 mL, 30.94 mmol), THF (200 mL), and diethyl ester of [(2-phenylethyl)thio]-propanedioic acid (1.00 g, 3.37 mmol). m.p. dec. 149–152° C.; $^{1}$H NMR (400 MHz, DMSO-$d_6$) δ2.78 (t, 2 H), 3.04 (t, 2 H), 6.98 (s, 1 H), 7.20 (m, 5 H), 7.74 (d, 2 H), 8.74 (d, 2 H).

Example 84

3-[1,4-Bis(phenylthio)butyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), cyclopropyl carboxaldehyde (0.436 mL, 5.84 mmol), thiophenol (1.40 mL, 13.8 mmol), piperdine (0.5 mL), acetic acid (0.5 mL). m.p. 75–77° C.; $^{1}$H NMR (400 MHz, DMSO-$d_6$) δ5.9 (s, 1 H), 6.71 (s, 1 H), 7.20 (m, 5 H), 7.44 (m, 7 H), 7.75 (m, 3 H), 7.82 (m, 2 H).

Example 85

4-Hydroxy-6-phenyl-3-[phenyl[(phenylmethyl)thio]methyl]-2H-pyran-2-one, (±)

The title compound was prepared by Method C using 4-hydroxy-6-phenyl-2H-pyran-2-one (1.00 g, 5.31 mmol), ethanol (10 mL), benzaldehyde (0.593 mL, 5.84 mmol), benzylmercaptan (1.62 mL, 13.8 mmol), piperdine (0.5 mL), acetic acid (0.5 mL). m.p. 189–191° C.; $^{1}$H NMR (400 MHz, DMSO-$d_6$) δ3.70 (dd, 2 H), 5.29 (s, 1 H), 6.65 (s, 1 H), 7.23 (m, 8H), 7.50 (m, 5 H), 7.73 (m, 2 H), 11.96 (bs, 1 H).

Example 86

4-Hydroxy-3-[[(2-methoxyphenyl)thio]phenylmethyl]-6-phenyl-2H-pyran-2-one, (±)

The title compound was prepared by Method C using 4-hydroxy-6-phenyl-2H-pyran-2-one (1.00 g, 5.31 mmol), ethanol (10 mL), benzaldehyde (0.593 mL, 5.84 mmol), 2-methoxythiophenol (1.93 mL, 13.8 mmol), piperdine (0.5 mL), acetic acid (0.5 mL). m.p. 165–170° C.; $^{1}$H NMR (400 MHz, DMSO-$d_6$) δ3.870 (s, 3 H), 5.81 (s, 1 H), 6.70 (s, 1 H), 6.84 (t, 1 H), 7.19 (m, 3 H), 7.28 (t, 2 H), 7.53 (m, 3 H), 7.75 (m,2H), 12.13 (bs, 1 H).

Example 87

4-Hydroxy-3-[3-methyl-1-(phenylthio)butyl]-6-phenyl-2H-pyran-2-one, (±)

The title compound was prepared by Method C using 4-hydroxy-6-phenyl-2H-pyran-2-one (1.00 g, 5.31 mmol), ethanol (10 mL), isovaleraldehyde (0.626 mL, 5.84 mmol), thiophenol (1.40 mL, 13.8 mmol), piperdine (0.5 mL), acetic acid (0.5 mL). m.p. 154–156° C.; $^{1}$H NMR (400 MHz, acetone-$d_6$) δ0.89 (d, 3 H), 0.93 (d,3H), 1.63 (m,1H), 1.80 (m, 1 H), 2.32 (m,1H), 4.82 (dd, 2 H), 6.70 (s, 1 H), 7.24 (m, 3 H), 7.82 (m, 2 H), 10.49 (bs, 1 H).

Example 88

3-[2-Cyclohexyl-1-(phenylthio)ethyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), cyclohexylmethyl carboxaldehyde (0.735 mL, 5.84 mmol), thiophenol (1.40 mL, 13.8 mmol), piperdine (0.5 mL), acetic acid (0.5 mL). m.p. dec. 205° C.; $^{1}$H NMR (400 MHz, acetone-$d_6$) δ0.91 (d, 3 H), 1.25 (m, 5 H), 1.73 (m, 5 H), 2.58 (m, 1 H), 4.83 (dd, 1 H), 6.69 (s, 1 H), 7.22 (m, 3 H), 7.48 (m, 5 H), 7.82 (m, 2 H).

Example 89

4-Hydroxy-6-(3-phenoxyphenyl)-3-[(2-phenylethyl)thio]-2H-pyran-2-one

The title compound was prepared by Method A using 3'-phenoxyacetophenone (2.00 g, 9.43 mmol), lithium bis(trimethylsilyl)amide (2.36 g, 14.15 mmol), chlorotrimethylsilane (1.79 mL, 14.15 mmol), THF (100 mL), and diethyl ester of [(2-phenylethyl)thio]-propanedioic acid (1.00 g, 3.37 mmol). m.p. 114–115° C.; $^{1}$H NMR (400 MHz, DMSO-$d_6$) δ2.76 (t, 2 H), 2.99 (t, 2 H), 6.76 (s, 1 H), 7.09 (m, 7 H), 7.34 (s, 1 H), 7.44 (t, 2 H), 7.56 (m, 2 H).

Example 90

4-Hydroxy-6-[3-methoxy-4-(phenylmethoxy)phenyl]-3-[(2-phenylethyl)thio]-2H-pyran-2-one The title compound was prepared by Method A using 4'-benzyloxy-3'-methoxyacetophenone (2.00 g, 7.81 mmol), lithium bis(trimethylsilyl)amide (1.96 g, 11.71 mmol), chlorotrimethylsilane (1.48 mL, 11.71 mmol), THF (80 mL), and diethyl ester of [(2-phenylethyl)thio]propanedioic acid (1.00 g, 3.37 mmol). m.p. 114–115° C.; $^{1}$H NMR (400 MHz, DMSO-$d_6$) δ2.77 (t, 2 H), 2.98 (t, 2 H), 3.86 (s, 1 H), 6.75 (s, 1 H), 7.21 (m, 7 H), 7.40 (m, 6 H).

Example 91

6-(3,5-Dimethylphenyl)-4-hydroxy-3-[(2-phenylethyl)thio]-2H-pyran-2-one

The title compound was prepared by Method A using 3',5'-dimethyl acetophenone (1.75 g, 11.82 mmol), lithium diisopropylamide (1.89 g, 17.73 mmol), chlorotrimethylsilane (2.25 mL, 17.73 mmol), THF (120 mL), and diethyl ester of [(2-phenylethyl)thio]-propanedioic acid (1.00 g, 3.37 mmol). m.p. 155–157° C.; $^{1}$H NMR (400 MHz, DMSO-$d_6$) δ2.34 (s, 6 H), 2.77 (t, 2 H), 2.99 (t, 2 H), 6.72 (s, 1 H), 7.21 (m, 6 H), 7.41 (s, 2 H), 8.74 (d, 2 H).

Example 92

4-Hydroxy-3-[[(3-methoxyphenyl)methyl]thio]-6-phenyl-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), [3-(methoxy)phenyl]methyl p-toluenethiosulfonate (2.12 g, 6.90 mmol). m.p. 134–136° C.; $^{1}$H NMR (400 MHz, DMSO-$d_6$) δ3.69 (s, 3 H), 3.99 (s,2H), 6.75 (m, 2 H), 6.83 (m, 2 H), 7.16 (t, 1 H), 7.53 (m, 3 H), 7.79 (m, 2 H).

Example 93

4-Hydroxy-3-[4-methyl-1-(phenylthio)pentyl]-6-phenyl-2H-pyran-2-one, (±)

The title compound was prepared by Method C using 4-hydroxy-6-phenyl-2H-pyran-2-one (1.00 g, 5.31 mmol), ethanol (10 mL), 4-methylpentanal (0.584 mL, 5.84 mmol), thiophenol (1.40 mL, 13.8 mmol), piperdine (0.5 mL), acetic acid (0.5 mL). m.p. 144–145° C.; $^{1}$H NMR (400 MHz, DMSO-$d_6$) δ0.80 (d, 3 H), 0.81 (d, 3 H), 1.07 (m, 1 H), 1.18 (m, 1 H), 1.49 (m, 1 H), 1.89 (m, 1 H), 2.19 (m, 1 H), 4.51 (dd, 1 H), 6.68 (s, 1 H), 7.19 (t, 1 H), 7.29 (t, 2 H), 7.35 (d, 2 H), 7.53 (m, 3 H), 7.76 (m, 2 H).

Example 94

4-Hydroxy-6-phenyl-3-[[[3-(phenylmethoxy)phenyl] methyl]thio]-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), [3-(benzoxyl)phenyl]methyl p-toluenethiosulfonate (2.65 g, 6.90 mmol). m.p. 140–141° C.; $^1$H NMR (400 MHz, DMSO-$d_6$) δ3.98 (s, 2 H), 5.01 (s, 2 H), 6.75 (s, 1 H), 6.83 (m, 2 H), 6.91 (m, 1 H), 7.28 (t, 1 H), 7.34 (m, 4 H), 7.52 (m, 3 H), 7.80 (m, 2 H).

Example 95

3-[(1,3-Benzodioxol-5-ylmethyl)thio]-4-hydroxy-6-phenyl-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), 1,3-benzodioxoyl-5-yl methyl p-toluenethiosulfonate (2.22 g, 6.90 mmol). m.p. 162–164° C.; $^1$H NMR (400 MHz, DMSO-$d_6$) δ3.92 (s, 2 H), 5.95 (s, 2 H), 6.75 (m, 4 H), 7.53 (m, 3 H), 7.79 (m, 2 H).

Example 96

4-Hydroxy-3-[[(2-methoxyphenyl)methyl]thio]-6-phenyl-2H-pyran-2-one

The title compound was prepared by Method B using 4-hydroxy-6-phenyl-2H-pyran-2-one (0.500 g, 2.65 mmol), ethanol (7 mL), 1N sodium hydroxide (2.65 mL), [(2-methoxyphenyl)methyl] p-toluenethiosulfonate (0.816 g, 2.65 mmol). m.p. 152–153° C.; $^1$H NMR (400 MHz, DMSO-$d_6$) δ3.73 (s, 3 H), 3.95 (s, 2 H), 6.71 (s, 1 H), 6.81 (t, 1 H), 6.91 (d, 1 H), 7.13 (d, 1 H), 7.17 (t, 1 H), 7.53 (m, 3 H), 7.79 (m, 2 H).

Example 97

4-Hydroxy-3-[[(2-methylphenyl)methyl]thio]-6-phenyl-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), [(2-methylphenyl)methyl] p-toluenethiosulfonate (1.55 g, 5.31 mmol). m.p. 176– 178° C.; $^1$H NMR (400 MHz, DMSO-$d_6$) δ2.42 (s, 3 H), 3.99 (s, 2 H), 6.74 (s, 1 H), 709 (m, 4 H), 7.53 (m, 3 H), 7.79 (m, 2 H).

Example 98

4-Hydroxy-3-[[(3-methylphenyl)methyl]thio]-6-phenyl-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), [(3-methylphenyl)methyl] p-toluenethiosulfonate (1.55 g, 5.31 mmol). m.p. 139–140° C.; $^1$H NMR (400 MHz, DMSO-$d_6$) δ2.23 (s, 3 H), 3.96 (s, 2 H), 6.74 (s, 1 H), 7.07 (m, 4 H), 7.54 (m, 3 H), 7.79 (m, 2 H).

Example 99

4-Hydroxy-3-[[(4-methylphenyl)methyl]thio]-6-phenyl-2H-pyran-2-one

The title compound was prepared by Method B using 4-hydroxy-6-phenyl-2H-pyran-2-one (1.00 g, 5.31 mmol), ethanol (15 mL), 1N sodium hydroxide, (5.31 mL), [(4-methylphenyl)methyl] p-toluenethiosulfonate (1.55 g, 5.31 mmol). m.p. 164–165° C.; $^1$H NMR (400 MHz, DMSO-$d_6$) δ2.23 (s, 3 H), 3.96 (s, 2 H), 6.74 (s, 1 H), 7.06 (d, 2 H), 7.14 (d, 2 H), 7.53 (m, 3 H), 7.79 (m, 2 H).

Example 100

6-[1,1'-Biphenyl]-3-yl-4-hydroxy-3-[(2-phenylethyl) thio]-2H-pyran-2-one

The title compound was prepared by Method A using 3'-phenylacetophenone (2.00 g, 10.21 mmol), trimethylsilyltriflate (2.36 mL, 12.24 mmol), triethylamine (2.84 mL, 20.40 mmol), methylene chloride (26 mL), and diethyl ester of [(2-phenylethyl)thio]propanedioic acid (1.00 g, 3.37 mmol). m.p. 93–94° C.; $^1$H NMR (400 MHz, DMSO-$d_6$) δ2.79 (t, 2 H), 3.01 (t, 2 H), 6.92 (s, 1 H), 7.21 (m, 5 H), 7.42 (t, 1 H), 7.52 (t, 2 H), 7.64 (t, 1 H), 7.75 (d, 2 H), 7.82 (t, 2 H), 8.02 (s, 1 H).

Example 101

4-Hydroxy-3-[[(4-methoxyphenyl)methyl]thio]-6-phenyl-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), [(4-methoxyphenyl)methyl] p-toluenethiosulfonate (2.21 g, 6.90 mmol). m.p. 168–170° C.; $^1$H NMR (400 MHz, DMSO-$d_6$) δ3.96 (s, 3 H), 3.95 (s, 2 H), 6.73 (s, 1 H), 6.81 (d, 2 H), 7.17 (d, 2 H), 7.53 (m, 3 H), 7.79 (m, 2 H).

Example 102

3-[2-Cyclohexyl-1-(cyclohexylthio)ethyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), cyclohexylmethyl carboxaldehyde (0.735 g, 5.84 mmol.), cyclohexylmercaptan (1.60 g, 13.8 mmol), piperdine (0.5 mL), acetic acid (0.5 mL). m.p. dec. 220° C.; $^1$H NMR (400 MHz, DMSO-$d_6$) δ0.86 (m, 2 H), 1.18 (m, 9H), 1.66 (m, 10H), 2.03 (m, 2 H), 2.58 (m, 2 H), 4.25 (m, 1 H), 6.68 (s, 1 H), 7.53 (m, 3 H), 7.75 (m,2H).

Example 103

3-[1-[(2,6-Dimethylphenyl)thio]-3-methylbutyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), isovaleraldehyde (0.63 mL, 5.84 mmol), 2,6-dimethylthiophenol (1.90 g, 13.8 mmol), piperdine (0.5 mL), acetic acid (0.5 mL). m.p. 166–167° C.; $^1$H NMR (400 MHz, DMSO-$d_6$) δ0.78 (d, 3 H), 0.83 (d, 3 H), 1.42 (m, 1 H), 1.47 (m, 1 H), 2.46 (m, 1 H), 2.51 (s, 6 H), 4.37 (m, 1 H), 6.51 (s, 1 H), 7.70 (m, 3 H), 7.52 (m, 3 H), 7.74 (m,2H).

Example 104

3-[1-(Cyclohexylthio)-2-cyclopropylethyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), cyclopropylmethyl carboxaldehyde (0.67 g, 5.84 mmol), cyclohexylmercaptan (1.68 mL, 13.8 mmol), piperdine (0.5 mL), acetic acid (0.5 mL). m.p. 69–71° C.; $^1$H NMR (400 MHz, DMSO-$d_6$) δ–0.02 (m, 1 H), 0.05 (m, 1 H), 0.34 (m, 2 H), 0.64 (m, 2 H), 1.22 (m, 5 H), 1.52 (m, 1 H), 1.67 (m, 3 H), 1.84 (m, 1 H), 1.97 (m, 2 H), 2.64 (m, 1 H), 4.21 (t, 1 H), 6.69 (s, 1 H), 7.52 (m, 3 H), 7.75 (m, 2 H).

Example 105

3-[1-[(2,6-Dichlorophenyl)thio]-3-methylbutyl]-4-hydroxy-6-phenyl-2H-pyran-2-one, (±)

The title compound was prepared by Method c using 4-hydroxy-6-phenyl-2H-pyran-2-one (1.00 g, 5.31 mmol), ethanol (10 mL), isovaleraldehyde (0.62 mL, 5.84 mmol), 2,6-dichlorothiophenol (2.74 g, 13.8 mmol), piperdine (0.5 mL), acetic acid (0.5 mL). m.p. 158–162° C.; $^1$H NMR (400 MHz, DMSO-$d_6$) δ0.83 (d, 3 H), 0.87 (d, 3 H), 1.49 (m, 1 H), 1.74 (m, 1 H), 2.39 (m, 1 H), 4.68 (m, 1 H), 6.769 (s, 1 H), 7.49 (m, 5 H), 7.74 (m, 3 H).

Example 106

3-[1-(Cyclohexylthio)-3,3-dimethylbutyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), 3,3-dimethylbutanal (0.73 mL, 5.84 mmol), cyclohexylmercaptan (1.86 mL, 13.8 mmol), piperdine (0.5 mL), acetic acid (0.5 mL). m.p. >225° C.; $^1$H NMR (400 MHz, DMSO-$d_6$) δ0.85 (s, 9H), 1.25 (m, 5 H), 1.65 (m, 7 H), 4.30 (m, 1 H), 6.69 (s, 1 H), 7.54 (m, 3 H), 7.75 (m, 2 H).

Example 107

[4-[4-Hydroxy-2-oxo-3-[(2-phenylethyl)thio]-2H-pyran-6-yl]-2-methylphenoxy], acetic acid, ethyl ester The title compound was prepared by Method A using ethyl (4-acetyl-2-methylphenoxy)acetate (2.00 g, 8.47 mmol), trimethyl silyltriflate (3.92 mL, 20.33 mmol), triethylamine (4.72 mL, 33.88 mmol), methylene chloride (22 mL), and diethyl ester of [(2-phenylethyl)thio]propanedioic acid (1.00 g, 3.37 mmol). m.p. 154–156° C.; $^1$H NMR (400 MHz, DMSO-$d_6$) δ1.22 (t, 3 H), 2.26 (s, 3 H), 2.77 (t, 2 H), 2.97 (t, 2 H), 4.17 (t, 2 H), 4.91 (s, 2 H), 6.66 (s, 1 H), 6.99 (d, 1 H), 7.21 (m, 5 H), 7.61 (m, 2 H).

Example 108

6-[3,5-Dimethyl-4-[[dimethyl(1,1-dimethylethyl)silyl]oxy]phenyl]-4-hydroxy-3-[(phenylmethyl)thio]-2H-pyran-2-one The title compound was prepared by Method A using 3',5'-dimethyl-4'-[[dimethyl(1,1-dimethylethyl)silyl]oxy]acetophenone (1.50 g, 5.39 mmol), trimethylsilyltriflate (1.24 mL, 6.47 mmol), triethylamine (1.50 mL, 10.78 mmol), methylene chloride (13 mL), and diethyl ester of [(phenylmethyl)thio]propanedioic acid (1.00 g, 3.54 mmol). m.p. 137–139° C.; $^1$H NMR (400 MHz, DMSO-$d_6$) δ0.21 (s, 6 H), 0.99 (s, 9H), 2.22 (s, 6 H), 3.96 (s, 2 H), 6.54 (s, 1 H), 6.99 (d, 1 H), 7.21 (m, 5 H), 7.44 (m, 2 H).

Example 109

4-Hydroxy-3-[(2-phenylethyl)thio]-6[4-(4-pyridinylmethoxy)phenyl]-2H-pyran-2-one The title compound was prepared by Method A using 4'-(4-pyridinylmethoxy)acetophenone (2.00 g, 8.81 mmol), trimethylsilyltriflate (2.04 mL, 10.57 mmol), triethylamine (2.45 mL, 17.62 mmol), methylene chloride (22 mL), and diethyl ester of [(2-phenylethyl)thio]propanedioic acid (1.00 g, 3.37 mmol). m.p. dec. 212° C.; $^1$H NMR (400 MHz, DMSO-$d_6$) δ2.73 (t, 2 H), 2.88 (t, 2 H), 5.29 (s, 2 H), 6.48 (s, 1 H), 7.18 (m, 5 H), 7.45 (d, 2 H), 7.74 (d, 2 H), 8.90 (d, 2 H).

Example 110

3-[1-(Cyclopentylthio)-3-methylbutyl]-4-hydroxy-6-phenyl-2H-pyran-2-one (±)

The title compound was prepared by Method C using 4-hydroxy-6-phenyl-2H-pyran-2-one (1.00 g, 5.31 mmol), ethanol (10 mL), isovaleraldehyde (0.62 mL, 5.84 mmol), cyclopentylmercaptan (1.43 mL, 13.8 mmol), piperdine (0.5 mL), acetic acid (0.5 mL). m.p. 146–149° C.; $^1$H NMR (400 MHz, DMSO-$d_6$) δ0.85 (d, 2 H), 0.87 (d, 2 H), 1.32 (m, 1 H), 1.54 (m, 7 H), 1.85 (m, 1 H), 2.00 (m, 2 H), 3.04 (m, 1 H), 4.20 (dd, 1 H), 6.69 (s, 1 H), 7.53 (m, 3 H), 7.76 (m,2H), 11.69 (bs, 1 H).

Example 111

[4-[4-Hydroxy-2-oxo-3[(2-phenylethyl)thio]-2H-pyran-6-yl]-2-methylphenoxy acetic acid To a tetrahydrofuran (10 ml) solution of [4-[4-hydroxy-2-oxo-3[(2-phenylethyl)thio]-2H-pyran-6-yl]-2-methylphenoxy]-, acetic acid, ethyl ester (0.20 g. 0.45 mmol) was added 1N sodium hydroxide (1.13 mL, 1.13 mmol). The reaction was stirred for 5 hrs, and then quenched by addition of water (10 ml) followed by acidification with conc. hydrochloric acid to pH 2. The aqueous layer is then extracted with 2× with ethyl acetate (100 ml). the combined organic extracts were then washed with saturated sodium chloride; dried over anhydrous magnesium sulfate. After evaporation of the solvents in vacuo, the crude product was purified by column chromatography (silica gel-230 to 400 mesh) using 94/5/1 methylene chloride/methanol/acetic acid as the eluent. m.p. dec. 210° C.; $^1$H NMR (400 MHz, DMSO-$d_6$) δ2.26 (s, 3 H), 2.78 (t, 2 H), 2.98 (t, 2 H), 4.81 (s, 2 H), 6.67 (s, 1 H), 6.97 (d, 2 H), 7.21 (m, 5 H), 7.61 (d, 2 H).

Example 112

3-[1-(Cyclohexylthio)-2-cyclopentylethyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), cyclopentylmethylcarboxaldehyde (0.65 g, 5.84 mmol), cyclohexylmercaptan (1.68 mL, 13.8 mmol), piperdine (0.5 mL), acetic acid (0.5 mL). m.p. 157–160° C.; $^1$H NMR (400 MHz, DMSO-$d_6$) δ1.44 (m, 18H), 2.01 (m, 1 H), 2.19 (m, 1 H), 2.60 (m, 1 H), 4.16 (m, 1 H), 6.68 (s, 1 H), 7.53 (m, 3 H), 7.75 (m,2H), 11.66 (bs, 1 H).

Example 113

4-Hydroxy-6-(4-hydroxy-3,5-dimethylphenyl)-3-[(phenylmethyl)thio]-2H-pyran-2-one To a THF (10 mL) solution of 6-[3,5-dimethyl-4-[[dimethyl(1,1-dimethylethyl)silyl]oxy]phenyl]-4-hydroxy-3-[(phenylmethyl)thio]-2H-pyran-2-one at 0° C. is added 3 N HCl (9.0 mL). The reaction is stirred for 48 hrs. at room temperature. The reaction is quenched by pouring onto ethyl acetate and washed in succession with water, saturated sodium chloride; dried over anhydrous magnesium sulfate. After evaporation of the solvents in vacuo, the crude product was purified by flash column chromatography ($SiO_2$-230 to 400 mesh) using 50% ethyl acetate/hexanes. m.p. 174–176° C.; $^1$H NMR (250 MHz, DMSO-$d_6$) δ2.21 (s, 6 H), 2.60 (m, 1 H), 3.96 (s, 2 H), 6.52 (s, 1 H), 7.23 (s, 5 H), 7.38 (s, 2 H), 9.06 (s, 1 H).

Example 114

4-Hydroxy-6-phenyl-3-[[[3-(2-phenylethoxy)phenyl] methyl]thio]-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), [3-(2-(phenylethoxy)phenyl]methyl p-toluenethiosulfonate (2.11 g, 5.31 mmol). m.p. 85–90° C.; $^1$H NMR (400 MHz, DMSO-$d_6$) δ2.96 (t, 2 H), 3.96 (s, 2 H), 4.09 (t, 2 H), 6.77 (m, 4 H), 7.19 (m, 5 H), 7.53 (m, 3 H), 7.77 (m, 2 H).

Example 115

4-Hydroxy-6-[4-(2-phenylethynyl)phenyl]-3-[(2-phenylethyl)thio]-2H-pyran-2-one

The title compound was prepared by Method A using 4'-(2-phenethynyl)acetophenone (1.50 g, 6.81 mmol), trimethylsilyltriflate (1.57 mL, 8.17 mmol), triethylamine (1.89 mL, 13.62 mmol), methylene chloride (17 mL), and diethyl ester of [(2-phenylethyl)thio]propanedioic acid (1.00 g, 3.37 mmol). m.p. 181–182° C.; $^1$H NMR (400 MHz, DMSO-$d_6$) δ2.78 (t, 2 H), 3.02 (t, 2 H), 6.85 (s, 1 H), 7.21 (m, 5 H), 7.45 (m, 3 H), 7.59 (d, 2 H), 7.86 (d, 2 H).

Example 116

4-Hydroxy-6-[4-(2-phenylethyl)phenyl]-3-[(2-phenylethyl)thio]-2H-pyran-2-one

The title compound was prepared by Method A using 4'-(2-phenethyl)acetophenone (1.50 g, 6.68 mmol), trimethylsilyltriflate (1.55 mL, 8.02 mmol), triethylamine (1.86 mL, 13.36 mmol), methylene chloride (17 mL), and diethyl ester of [(2-phenylethyl)thio]propanedioic acid (1.00 g, 3.37 mmol). m.p. 122–123° C.; $^1$H NMR (400 MHz, DMSO-$d_6$) δ2.77 (t, 2 H), 2.93 (m, 4 H), 2.99 (t, 2 H), 6.75 (s, 1 H), 7.26 (m, 5 H), 7.38 (d, 2 H), 7.71 (d, 2 H).

Example 117

3-[(Cyclohexylthio)phenylmethyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), benzaldehyde (0.593 mL, 5.84 mmol), cyclohexylmercaptan (1.68 mL, 13.8 mmol), piperdine (0.5 mL), acetic acid (0.5 mL). m.p. 189–191° C.; $^1$H NMR (400 MHz, DMSO-$d_6$) δ1.21 (m, 5 H), 1.52 (m, 1 H), 1.91 (m, 2 H), 2.58 (m, 2 H), 5.37 (s, 1 H), 6.70 (s, 1 H), 7.17 (t, 1 H), 7.53 (m, 5 H), 7.74 (m, 2 H), 11.96 (bs, 1 H).

Example 118

4-Hydroxy-3-[(phenylmethyl)thio]-6-[3-(trifluoromethoxy)phenyl]-2H-pyran-2-one

The title compound was prepared by Method A using 3'trifluoromethoxyacetophenone (3 g, 14.7 mmol), lithium bis(trimethylsilylamide (2.45 g, 14.7 mmol), chlorotrimethylsilane (2.47 g, 14.7 mmol) and diethyl ester of [(phenylmethyl)thio]propanedioic acid (1.00 g, 3.54 mmol). m.p. 128–132° C.; $^1$H NMR (400 MHz, DMSO-$d_6$) δ4.03 (s, 2 H), 6.81 (s, 1 H), 7.2 (m, 2 H), 7.28 (m, 3 H), 7.56 (dd, 1 H), 7.69 (t, 1 H), 7.75 (s, 1 H), 7.86 (d, 1 H); IR (KBr) 2963, 1651, 1550, 1394, 1369, 1395, 1263, 1098, 1024, 800 $cm^{-1}$; MS (CI): m/e 395 (M+H, 37), 309 (8), 273 (7), 205 (3), 119 (10); Analysis calc'd for $C_{19}H_{13}O_4S_1F_3.H_2O$: C, 55.34; H, 3.67; found: C, 54.94; H, 4.03.

Example 119

3-[(Cyclohexylmethyl)thio]-4-hydroxy-6-phenyl-2H-pyran-2-one

The title compound was prepared by Method B using 4-hydroxy-6-phenyl-2H-pyran-2-one (0.5 g, 2.66 mmol), ethanol (7 mL), 1N sodium hydroxide (2.66 mL), cyclohexylmethyl-p-toluenethiosulfonate (0.756 g, 2.66 mmol). m.p. 141–143° C.; $^1$H NMR (400 MHz, DMSO-$d_6$) δ0.92 (m, 2 H), 1.14 (m, 3 H), 1.19 (m, 1 H), 1.61 (m, 3 H), 1.83 (m, 2 H), 2.64 (d, 2 H), 6.78 (s, 1 H), 7.53 (m, 3 H), 7.81 (m, 2 H); IR (KBr) 3106, 2922, 1651, 1547, 1396, 1099, 766 $cm^{-1}$; MS (CI) m/e 317 (M+H, 16), 279 (83), 242 (77), 201 (27), 177 (19), 134 (54), 105 (65), 97 (100).

Example 120

4-Hydroxy-3-[(2-phenylethyl)thio]-6-[3-methyl-4-(3-pyridinylmethoxy)phenyl]-2H-pyran-2-one The title compound was prepared by Method A using 3'-methyl-4'-(3-pyridinylmethoxy)acetophenone (2.0 g, 8.29 mmol), lithium bis(trimethylsilylamide (1.53 g, 9.13 mmol), chlorotrimethylsilane (1.54 g, 9.13 mmol) and diethyl ester of [2-(phenylethyl)thio]propanedioic acid (1.00 g, 3.37 mmol). m.p. 149–151° C.; $^1$H NMR (400 MHz, DMSO-$d_6$) δ2.25 (s, 3 H), 2.78(t, 2 H), 2.97 (t, 2 H), 5.28 (s, 2 H), 6.69 (s, 1 H), 7.22 (m, 6 H), 7.44 (dd, 1 H), 7.67 (s+d, 2 H), 7.92 (d, 1 H), 8.58 (brs, 1 H), 8.72 (brs, 1 H); IR (KBr) 3430, 2926, 1713, 1626, 1505, 1263, 1136, 1028, 808, 705 $cm^{-1}$; MS (CI): m/e 446 (M+H), 341 (15), 200 (6), 105 (100); Analysis calc'd for $C_{26}H_{23}O_4S_1N_1$: C, 70.09; H, 5.20; N, 3.14; found: C, 70.31; H, 5.27; N, 2.95.

Example 121

6-(2,3-Dihydro-1,4-benzodioxin-6-yl)-4-hydroxy-3-[(phenylmethyl)thio]-2H-pyran-2-one The title compound was prepared by Method A using 1,4-benzodioxin-6-yl methyl ketone (2.5 g, 14.25 mmol), lithium bis(trimethylsilylamide (2.35 g, 14.25 mmol), chlorotrimethylsilane (2.47 g, 14.25 mmol) and diethyl ester of [(phenylmethyl)thio]propanedioic acid (1.00 g, 3.55 mmol). m.p. 192–193° C.; $^1$H NMR (400 MHz, DMSO-$d_6$) δ3.99 (s, 2 H), 4.17 (m, 4 H), 6.8 (s, 1 H), 7.0 (d, 1 H), 7.2 (m, 1 H), 2.28 (m, 7 H); IR (KBr) 3435, 2924, 1649, 1624, 1508, 1288, 1066, 698 $cm^{-1}$; MS (CI): m/e 369 (M+H,), 277 (12), 233 (12), 163 (9), 107 (10), 91 (76); Analysis calc'd for $C_{20}H_{16}O_5S_1$: C, 65.21; H, 4.38; found: C, 64.80; H, 4.17.

Example 122

4-Hydroxy-3-[(2-phenylethyl)thiol-6-[3-(trifluoromethyl)phenyl]-2H-pyran-2-one

The title compound was prepared by Method A using the corresponding trimethylsilyl enol ether (4.5 mmol) and diethyl ester of [(2-phenylethyl)thio]propanedioic acid (1.33 g, 4.55 mmol). m.p. 117–118° (C.); $^1$H NMR (400 MHz, DMSO-$d_6$) δ2.8 (t, 2 H), 3.03 (t, 2 H), 6.94 (s, 1 H), 7.2 (m, 5 H), 7.8 (t, 1 H), 7.94 (t, 1 H), 8.08 (s, 1 H), 8.14 (d, 1 H); IR (KBr) 3435, 3026, 2924, 1720, 1635, 1543, 1327, 1171, 1130, 696 cm$^{-1}$; MS (CI): m/e 393 (M+H, 100), 373 (9), 288 (38), 256 (20), 224 (11), 105 (62); Analysis calc'd for $C_{20}H_{15}S_1O_3F_3.H_2O$: C, 58.53; H, 4.18; found: C, 59.28; H, 3.81.

Example 123

4-Hydroxy-3-[(phenylmethyl)thio]-6-[3-(trifluoromethyl)phenyl]-2H-pyran-2-one

The title compound was prepared by Method A using the corresponding trimethylsilyl enol ether (9.8 mmol) and diethyl ester of [(phenylmethyl)thio]propanedioic acid (2.76 g, 9.88 mmol). m.p. 152–153° C.; $^1$H NMR (400 MHz, DMSO-$d_6$) δ3.97 (s, 2 H), 6.53 (s, 1 H), 7.25 (m, 5 H), 7.61 (t, 1 H), 7.75 (d, 1 H), 8.03 (d, 1 H), 8.08 (s, 1 H); IR (KBr) 3434, 3244, 1678, 1628, 1535, 1522, 1435, 1341, 1316, 1192, 1132, 936, 706 cm$^{-1}$; MS (CI) m/e 379 (M+H,), 257 (1), 91 (100); Analysis calc'd for $C_{19}H_{13}O_3S_1F_3$: C, 60.31; H, 3.46; found: C, 60.53; H, 3.57.

Example 124

4-Hydroxy-3-[(phenylmethyl)thio]-6-(2,3,4-trimethoxyphenyl)-2H-pyran-2-one

The title compound was prepared by Method A using 2',3',4'-trimethoxyacetophenone (1.5 g, 7.13 mmol), lithium bis(trimethylsilyl)amide (1.43 g, 8.56 mmol), chlorotrimethylsilane (1.8 mL, 10.67 mmol) and diethyl ester of [(phenylmethyl)thio]propanedioic acid (1.00 g, 3.54 mmol).

Example 125

N-[4-[4-Hydroxy-2-oxo-3-[(2-phenylethyl)thio]-2H-pyran-6-yl]phenyl]-benzenesulfonamide The title compound was prepared by Method A using the corresponding benzenesulfonamide (3.0 g, 10.91 mmol), lithium bis(trimethylsilylamide (3.65 g, 21.82 mmol), chlorotrimethylsilane (3.68 mL, 21.82 mmol) and diethyl ester of [(phenylethyl)thio]propanedioic acid (1.00 g, 3.37 mmol). m.p. 89–91° C.; $^1$H NMR (400 MHz, DMSO-$d_6$) δ2.78 (t, 2 H), 3.03 (t, 2 H), 6.86 (s, 1 H), 7.25 (m, 6 H), 7.72 (t, 3 H), 7.86 (m, 5 H); IR (KBr) 3443, 3335, 1725, 1632, 1543, 1383, 1171, 912, 729, 581, 552 cm$^{-1}$; Analysis calc'd for $C_{25}H_{21}N_1S_2O_5$. $H_2O$: C, 60.35; H, 4.66; N, 2.81; found: C, 60.13; H, 4.47; N, 3.23.

Example 126

6-[4-[(3,5-Dimethyl-4-isoxazolyl)methoxy]phenyl]-4-hydroxy-3-[(2-phenylethyl)thio]-2H-pyran-2-one The title compound was prepared by Method A using 4'-(3,5-dimethyl-4-isoxazolyl)acetophenone (1.65 g, 6.74 mmol), lithium bis(trimethylsilylamide (1.13 g, 6.74 mmol), chlorotrimethylsilane (1.14 mL, 6.74 mmol) and diethyl ester of [(2-phenylethyl)thio]propanedioic acid (1.00 g, 3.37 mmol). m.p. 152–154° C.; $^1$H NMR (400 MHz, DMSO-$d_6$) δ2.22 (s, 3 H), 2.31 (s, 3 H), 2.78 (t, 2 H), 2.99 (t, 2 H), 5.03 (s, 2 H), 6.69 (s, 1 H), 7.17 (d, 3 H), 7.25 (m, 4 H), 7.78 (d, 2 H); IR (KBr) 2936, 2979, 1640, 1510, 1406, 1182, 988, 820, 764 cm$^{-1}$; MS (CI) m/e 450 (M+H), 341 (10), 236 (9), 112 (76), 105 (100); Analysis calc'd for $C_{25}H_{23}N_1O_5S_1$: C, 66.80; H, 5.16; N, 3.12; found: C, 66.42; H, 5.20; N, 2.74.

Example 127

(±) 3-[(Cyclohexylthio)phenylmethyl]-4-hydroxy-6-[3-methyl-4-(3-pyridinylmethoxy)phenyl]-2H-pyran-2-one The title compound was prepared by Method C using 4-hydroxy-6-[3-methyl-4-(3-pyridinylmethoxy)phenyl]-2H-pyran-2-one (0.5 g, 1.62 mmol), benzaldehyde (0.189 g, 1.78 mmol), cyclohexylmercaptan (0.489 g, 4.212 mmol), piperidine, (0.5 mL), acetic acid (0.5 mL). m.p. 84–87° C. (d); IR (KBr) 3059, 2930, 2853, 1676, 1601, 1449, 1260, 1134, 700 cm$^{-1}$; MS (CI) m/e 446 (2), 331 (9), 226 (61), 205 (24), 135 (44).

Example 128

2-[[(4-hydroxy-2-oxo-6-phenyl-2H-pyran-3-yl)thio]methyl]-benzoic acid methyl ester The title compound was prepared by Method B using 4-hydroxy-6-phenyl-2H-pyran-2-one (2.0 g, 10.63 mmol), t2-(carbomethoxy)phenyl]methyl p-toluenethiosulfonate (3.57 g, 10.63 mmol), 1N NaOH (10.63 mL), ethanol (20 mL). m.p. 122–123° C.; $^1$H NMR (400 MHz, DMSO-$d_6$) δ3.81 (s, 3 H), 4.31 (s, 2 H), 6.67 (s, 1 H), 7.25 (d, 1 H), 7.31 (t, 1 H), 7.44 (t, 1 H), 7.44 (m, 3 H), 7.53 (d, 1 H), 7.99 (m, 3 H); IR (KBr) 3005, 2951, 1721, 1653, 1543, 1400, 1267, 1078, 966, 766, 711, 520 cm$^{-1}$; MS (CI) m/e 397 (M+29, 4), 369 ((M+H), 40), 337 (34), 191 (26), 149 (100), 105 (14).

Example 129

3-[1-(Cyclohexylthoi)-3-methylbutyl]-6-(2,3-dihydro-1,4-benzodioxin-6-yl) 4-hydroxy-2H-pyran-2-one (±)

The title compound was prepared by Method C using 4-hydroxy-6-[1,4-benzodioxin-6-yl]-2H-pyran-2-one (1.0 g, 4.06 mmol), isovaleraldehyde (0.35 g, 4.06 mmol), cyclohexylmercaptan (0.944 g, 8.12 mmol), piperidine, (0.5 mL), acetic acid (0.5 mL). m.p. 161–162° C.;$^1$H NMR (400 MHz, DMSO-$d_6$) δ0.85 (d, 3 H), 0.88 (d, 3 H), 1.2 (m, 5 H), 1.39 (m, 1 H), 1.53 (m, 2 H), 1.65 (m, 2 H), 1.81 (brm, 1 H), 2.04 (m, 2 H), 4.2 (q, 1 H), 4.32 (brq, 4 H), 6.53 (s, 1 H), 6.99 (d, 1 H), 7.2 (d, 1H), 7.25 (dd, 1H); IR (KBr) 1099, 2930, 2853, 1649, 1564, 1510, 1397, 1314, 1289, 1260, 1140, 1069, 891, 771, 608 cm$^{-1}$.

Example 130

2-[[4-hydroxy-2-oxo-3-[(2-phenylethyl)thio]-2H pyran-6-yl]phenoxy]methyl]-benzoic acid methyl ester The title compound was prepared by Method A using 2-[[(4-acetyl phenoxy]methyl]benzoic acid methyl ester (2.0 g, 7.04 mmol), trimethylsilyltrifluoromethylsulfonate (1.57 g, 7.04 mmol), triethylamine (1.42 g, 14.08mmol) and diethyl ester of [(2-phenylethyl)thio]propanedioic acid (1.04 g, 3.52 mmol). m.p. 161–162° C.; $^1$H NMR (400 MHz, DMSO-$d_6$) δ2.78 (t, 2 H), 2.97 (t, 2 H), 3.81 (s, 3 H), 5.5 (s, 2 H), 6.69 (s, 1 H), 7.14 (m, 3 H), 7.25 (m, 4 H), 7.5 (m, 2 H), 7.78 (m, 2 H), 7.78 (d, 2 H), 7.94 (d, 1H); IR (KBr) 3028, 2949, 2909, 2675, 1715, 1638, 1510, 1402, 1291, 1267, 1181, 1030, 828, 747 cm$^{-1}$; MS (CI) m/e 489 (M+H, 51), 384 (3), 353 (1), 149 (100), 135 (47), 105 (33).

Example 131

4-Hydroxy-3-[(2-phenylethyl)thio]-6-[4-(1H-tetrazol-5- ylmethoxy)phenyl]-2H -pyran-2-one The title compound was prepared by using example 143 (0.5 g, 1.32 mmol) and trimethyltin azide (0.543 g, 2.64 mmol), toluene (10 mL) and ethanol (10 mL) at its reflux temperature for 24 hours. The solvents were evaporated. The residue was treated with 1N HCl and stirred at room temperature for 2 hours. The residue was taken up in methanol, the solvents were then evaporated and the solid obtained was washed with ethyl acetate to obtain pure compound. m.p. 195–196° C. (dec); $^1$H NMR (400 MHz, DMSO-$d_6$) δ 2.78 (t, 2 H), 2.99 (t, 3 H), 5.6 (s, 2 H), 6.72 (s, 1 H), 7.22 (m, 7 H), 7.81 (d, 2 H); IR (KBr) 3121, 3028, 1657, 1549, 1512, 1410, 1256, 1186, 1059, 831, 696 $cm^{-1}$; MS (CI) m/e 423 (M+H, 8), 341 (3), 137 (11), 105 (100).

Example 132

4-Hydroxy-6-[3-methyl-4-[(2-pyridinyl)methoxy]phenyl]-3-[(2-phenylethyl) thio]-2H-pyran-2-one The title compound was prepared by Method A using 4-(2-pyridinylmethoxy) -3-methylacetophenone (2.0 g, 8.29 mmol), trimethylsilyltrifluoromethylsulfonate(8.29 g, 8.29 mmol), triethylamine (1.68 g, 16.58 mmol) and diethyl ester of [(2-phenylethyl)thio]propanedioic acid (1.22 g, 4.15 mmol). m.p. 75–77° C.; $^1$H NMR (400 MHz, DMSO-$d_6$) δ2.32 (s, 3 H), 2.78 (t, 3 H), 2.97 (t, 2H), 5.29 (s, 2H), 6.67 (s, 1H), 7.14–7.29 (m, 4H), 7.38 (m, 1H), 7.56 (m, 2H), 7.67 (m, 2H), 7.86 (t, 2H), 8.61 (d, 1H); IR (KBr) 3063, 2924, 1719, 1603, 1505, 1267, 1138, 1039, 760 $cm^{-1}$; MS (CI) m/e 446 (M+H, 90), 341 (16), 279 (17), 242 (21), 151 (25), 105 (100); Analysis calc'd for C26H2304N1S1: C, 70.09; H, 5.2; N, 3.4; found: C, 70.68; H, 5.28; N, 3.14.

Example 133

3-[2-Cyclopropyl-1-[(phenylmethyl)thio]ethyl]-4-hydroxy-6-phenyl-2H-pyran-2-one (±)

The title compound was prepared by Method C using 4-hydroxy-6-phenyl-2H -pyran-2-one (1.5 g, 7.98 mmol), 2-cyclopropylmethylcarboxaldehyde (0.67 g, 7.98 mmol), benzylmercaptan (1.98 g, 15.96 mmol), piperidine, (0.5 mL), acetic acid (0.5 mL). m.p. 59–61° C.; $^1$H NMR (400 MHz, DMSO-$d_6$) δ–0.97 (m, 2 H), 0.28 (m, 2 H), 0.58 (m, 1 H), 1.61 (m, 1 H), 2.01 (m, 1 H), 3.72 (ABXq, 2 H), 4.22 (q, 1H), 6.67 (s, 1H), 7.18 (t, 1H), 7.25 (d, 2H), 7.31 (t, 2H), 7.53 (m, 3H), 7.75 (m, 2H); IR (KBr) 3061, 2919, 2631, 1649, 1564, 1404, 1267, 766, 691 $cm^{-1}$; MS (CI) m/e 255 ((M-SBzl), 19), 201 (5), 147 (2); Analysis calc'd for C23H2203S1: C, 72.99; H, 5.86; found: C, 72.31; H, 6.08.

Example 134

4-Hydroxy-3-[1-[(2-methoxyphenyl)thio]-3-methylbutyl]-6-phenyl-2H-pyran-2-one (±)

The title compound was prepared by Method C using 4-hydroxy-6-phenyl-2H-pyran-2-one (1.5 g, 7.98 mmol), isovaleraldehyde (0.69 g, 7.98 mmol), 2-methoxythiophenol (2.24 g, 15.96 mmol), piperidine, (1.0 mL), acetic acid (1.0 mL) and ethanol (15 mL). m.p. 75–78° C.; $^1$H NMR (400 MHz, DMSO-$d_6$) δ0.86 (d, 3 H), 0.89 (d, 3 H), 1.53 (m, 1 H), 1.69 (m, 1 H), 2.19 (m, 1 H), 3.64 (s, 3 H), 4.69 (q, 1 H), 6.64 (s, 1 H), 6.89 (t, 1 H), 6.94 (d, 1 H), 7.17 (t, 1 H), 7.33 (d, 1 H), 7.53 (m, 3 H), 7.78 (m, 2 H); IR (KBr) 3063, 2955, 2635, 1649, 1564, 1406, 1242, 1026, 768, 750, 691 $cm^{-1}$; MS (CI) m/e 257 ((M—SPh(OMe), 11), 201 (3), 169 (5), 141 (88); Analysis calc'd for C23H2404S1: C, 69.67; H, 6.10; found: C, 69.63; H, 5.92.

Example 135

4-Hydroxy-3-[1-[(phenylmethyl)thio]-3-methylbutyl]-6-phenyl-2H-pyran-2-one (±)

The title compound was prepared by Method C using 4-hydroxy-6-phenyl-2H-pyran-2-one (1.5 g, 7.98 mmol), isovaleraldehyde (0.69 g, 7.98 mmol), benzylmercaptan (1.98 g, 15.96 mmol), piperidine, (1.0 mL), acetic acid (1.0 mL). m.p. 153–155° C.; $^1$H NMR (400 MHz, DMSO–$d_6$) δ0.64 (d, 3 H), 0.81 (d, 3 H), 1.25 (m, 1 H), 1.53 (m, 1 H), 2.04 (m, 1 H), 3.69 (ABXq, 2 H), 4.22 (q, 1 H); IR (KBr) 3086, 2955, 1651, 1566, 1497, 1404, 1311, 1127, 912, 766, (8).

Example 136

4-[[4-[4-hydroxy-2-oxo-3-[(2-phenylethyl)thio]-2H-pyran-6-yl]phenoxy]methyl]benzoic acid methyl ester The title compound was prepared by Method A using 4-[[(4-acetyl) phenoxy]methyl]benzoic acid methyl ester (2.0 g, 7.04 mmol), lithium hexamethyldisilazide (2.36 g, 14.08 mmol), chlorotrimethylsilane (2.38 g, 14.08 mmol) and diethyl ester of [(2-phenylethyl) thio]propanedioic acid (1.0 g, 3.05 mmol). m.p. 157–158° C.; $^1$H NMR (400 MHz, DMSO-$d_6$) δ2.78 (t, 2 H), 2.97 (t, 2 H), 3.86 (s, 2 H), 5.31 (s, 2 H), 6.67 (s, 1 H), 7.17 (q, 4 H), 7.25 (m, 3 H), 7.61 (d, 2 H), 7.78 (d, 2H), 8.0 (d, 2H); IR (KBr) 3023, 2936, 2581, 1632, 1510, 1404, 1258, 1184, 1098, 1009, 818, 718 $cm^{-1}$; MS (CI) m/e 517 (M+29, 7), 489 (M+H, 55), 384 (19), 149 (40), 105 (100).

Example 137

Methyl ester of 3-[[4-[4-hydroxy-2-oxo-3-[(2-phenylethyl)thio]-2H-pyran-6-yl]phenoxy]methyl]-benzoic acid The title compound was prepared by Method A using 3-[[(4-acetyl)phenoxy]methyl]benzoic acid methyl ester (2.0 g, 7.04 mmol), lithiumhexamethyldisilazane (2.36 g, 14.08 mmol), chlorotrimethylsilane (2.38 g, 14.08 mmol) and diethyl ester of [(2-phenylethyl)thio]propanedioic acid (1.0 g, 3.05 mmol). m.p. 147–149° C.; $^1$H NMR (400 MHz, DMSO-$d_6$) δ2.78 (t, 2 H), 2.97 (t, 2 H), 3.86 (s, 2 H), 5.31 (s, 2 H), 6.69 (s, 1 H), 7.2 (m, 7 H), 7.58 (t, 1 H), 7.75 (m, 3 H), 7.78 (d, 1 H), 7.94 (d, 1 H), 8.08 (s, 1 H); IR (KBr) 3081, 2950, 1726, 1632, 1609, 1512, 1406, 1345, 1406, 1290, 1209, 1098, 1004, 820, 748, 696 $cm^{-1}$; MS (CI) m/e 489 (M+H, 48), 384 (16), 341 (7), 236 (6), 149 (39), 119 (11), 105 (100).

Example 138

6[4-[3,4-Dichlorophenylmethoxy]phenyl]-4-hydroxy-3-[(2-phenylethyl)thio]-2H-pyran-2-one The title compound was prepared by Method A using 4-[(3,4-dichlorophenl) methoxy]acetophenone (2.0 g, 6.80 mmol), lithium hexamethyldisilazide (2.28 g, 13.61 mmol), chlorotrimethylsilane (2.3 g, 13.61 mmol) and diethyl ester of [(2-phenylethyl)thio]propanedioic acid (1.0 g, 3.40 mmol). m.p. 168–169° C.; $^1$H NMR (400 MHz, DMSO-$d_6$) δ2.78 (t, 2 H), 2.97 (t, 2 H), 5.22 (s, 2 H), 6.69 (s, 1 H), 7.17 (m, 8H), 7.47 (dd, 1 H), 7.69 (d, 1H), 7.78 (d, 1H); IR (KBr) 3054, 2602, 1713, 1611, 1512, 1399, 1291, 1179, 1109, 1042, 818, 754 $cm^{-1}$; MS (CI) m/e 501 (17), 499 (24), 394 (12), 353 (1), 161 (20), 159 (27), 105 (100).

Example 139

3-[[(4-hydroxy-2-oxo-6-phenyl-2H-pyran-3-yl)thio]methyl]-benzoic acid methylester The title compound was prepared by Method B using 4-hydroxy-6-phenyl-2H-pyran-2-one (2.0 g, 10.63 mmol),

[3-(carbomethoxy) phenyl]methyl p-toluenethiosulfonate (3.57 g, 10.63 mmol), IN NaOH (10.63 mL), ethanol (20 mL). m.p. 170–171° C.; $^{1}$H NMR (400 MHz, DMSO-$d_6$) δ3.78 (s, 3 H), 4.06 (s, 2 H), 6.72 (s, 1 H), 7.42 (t, 1 H), 7.53 (m, 4 H), 7.78 (m, 3 H), 7.83 (s, 1 H); IR (KBr) 3108, 2947, 1716, 1644, 1549, 1400, 1302, 1100, 770, 713, 523 $cm^{-1}$; MS (CI) m/e 369 (M+H, 7), 337 (8), 235 (6), 189 (4), 149 (11), 85 (100).

Example 140

Methylester of 4-[[(4-hydroxy-2-oxo-6-phenyl-2H-pyran-3-yl)thio]methyl]benzoic acid The title compound was prepared by Method B using 4-hydroxy-6-phenyl-2H-pyran-2-one (2.0 g, 10.63 mmol), [4-(carbomethoxy)]methyl p -toluenethiosulfonate (3.57 g, 10.63 mmol), 1N NaOH (10.63 mL), ethanol (20 mL). m.p. 215–216° C.; $^{1}$H NMR (400 MHz, DMSO-$d_6$) δ3.81 (s, 3 H), 4.06 (s, 2 H), 6 (69, J=s Hz, 1 H), 7.39 (d, 2 H), 7.67 (m, 3 H), 7.81 (m, 2 H), 7.86 (d, 2 H); IR (KBr) 3110, 3038, 1717, 1644, 1547, 1402, 1279, 1103, 720, 526 $cm^{-1}$; MS (CI) m/e 369 (M+H, 22), 235 (100), 207 (18), 189 (37), 151 (55), 119 (20), 105 (21), 85 (28).

Example 141

6-[3,5-Bis(trifluoromethyl)phenyl]-4-hydroxy-3-[(phenylmethyl)]-2H-pyran-2-one

The title compound was prepared by Method A using trimethylsilyl ether of 3',5'-trifluoromethylacetophenone (2.16 g, 7.1 mmol) [prepared using 3,5-ditrifluoromethylacetophenone (15 g, 58.55 mmol) and trimethylsilyltrimethylsulfonate (13.01 g, 58.55 mmol) and triethylamine (11.84 g, 117.10 mmol) and distilled], and diethyl ester of [(phenylmethyl)thio]propanedioic acid (1.0 g, 3.55 mmol). m.p. 80–82° C.; $^{1}$H NMR (400 MHz, $CDCl_3$) δ4.0 (s, 2 H), 6.61 (s, 1 H), 7.22 (m, 2 H), 7.28 (m, 3 H), 7.97 (s, 1 H), 8.25 (s, 2 H); IR (KBr) 3090, 1726, 1682, 1638, 1549, 1530, 1385, 1281, 1182, 1138, 902, 700 cm-$^{-1}$; MS (CI) m/e 475 (M+29, 3), 447 (M+H, 21), 213 (1), 149 (2), 91 (100).

Example 142

3-[l-(Cyclohexylthio)-3-methylbutyl]-4-hydroxy-6-phenyl-2H-pyran-2-one (±)

The title compound was prepared by Method C using 4-hydroxy-6 -phenyl-2H-pyran-2-one (1.5 g, 7.98 mmol), isovaleraldehyde (076 g, 8.78 mmol), cyclohexylmercaptan (2.04 g, 17.56 mmol), piperidine, (1.0 mL), acetic acid (1.0 mL) and ethanol (20 mL).m.p. 210–212° C.; $^{1}$H NMR (400 MHz, DMSO-$d_6$) δ0.89 (t, 6 H), 1.36 (m, 6 H), 1.44 (m, 1 H), 1.56 (m, 2 H), 1.69 (m, 2 H), 1.81 (m, 1 H), 2.08 (m, 2 H), 2.61 (brm, 1 H), 4.22 (m, 1 H), 6.67 (s, 1 H), 7.53 (m, 3 H), 7.78 (m, 2 H); IR (KBr) 3106, 2928, 2851, 1659, 1568, 1404, 1125, 766, 569 $cm^{-1}$; MS (CI) m/e 259 (50), 257 (49), 201 (46), 189 (16), 147 (8), 105 (28), 83 (100).

Example 143

[4-[4-Hydroxy-2-oxo-3-[(2-phenylethyl)thio]-2H-pyran-6-yl ]phenoxy]acetonitrile

The title compound was prepared by Method A using the appropriate acetophenone (3.0 g, 17.12 mmol), trimethylsilyltrifluoromethylsulfonate (3.8 g, 17.12 mmol), triethylamine (3.46 g, 34.24mmol) and diethyl ester of [2-(phenylethyl)thio]propanedioic acid (2.53 g, 8.56 mmol). m.p. 157–159° C.;$^{1}$H NMR (400 MHz, DMSO-$d_6$) δ2.92 (t, 2 H), 3.11 (t, 2 H), 4.86 (s, 2 H), 6.56 (s, 2 H), 7.08 (d, 2 H), 7.19 (t, 3 H), 7.3 (m, 3 H), 7.86 (d, 2 H); IR (KBr) 2993, 2577, 1634, 1510, 1404, 1342, 1302, 1226, 1188, 1098, 1051, 833, 717, 505 $cm^{-1}$; MS (CI) m/e 380 (100), 275 (60), 205 (8), 105 (94).

Example 144

4-Hydroxy-3-[(2-isopropylphenyl)thio]-6-phenyl-2H-pyran-2-one

The title compound was prepared by Method A using 1-phenyl-1-(trimethylsilyloxy)ethylene (1.24 g, 6.45 mmol), and diethyl ester of (2-isopropylphenyl)thio propanedioic acid (1.0 g, 3.23 mmol). $^{1}$H NMR (400 MHz, DMSO-$d_6$) δ1.25 (d, 6 H), 3.42 (m, 1 H), 6.89 (s, 1 H), 6.92 (dd, 1 H), 7.06 (t, 1 H), 7.13 (t, 1 H), 7.28 (d, 1 H), 7.56 (m, 3 H), 7.85 (m, 2 H) ; IR (KBr) 3117, 2962, 1661, 1551, 1406, 1365, 1101, 760 $cm^{-1}$; MS (CI) m/e 339(100), 305 (4), 219 (25), 189 (11), 147 (9), 105 (9); Analysis calc'd for C20H1803S1: C, 70.98; H, 5.36; found: C, 70.82; H, 5.24.

Example 145

3-[(Cyclopropylmethyl)thio]-4-hydroxy-6-phenyl-2H-pyran-2-one

The title compound (0.053 g, m.p. 136–137° C.) was prepared by method B using 4-hydroxy-6-phenyl-2H-pyran-2-one (0.250 g, 1.33 mmol), cyclopropylmethyl-p-toluenethiosulfonate (0.585 g, 2.261 mmol), triethylamine (0.158 g, 1.46 mmol), sodium bicarbonate (0.110 g, 1.33 mmol), ethanol (10.0 mL). $^{1}$H NMR (250 MHz, $CDCl_3$) δ7.994–7.726 (m, 2 H), 7.683–7.406 (m, 3 H), 6.665 (s, 1 H), 2.724–2.694 (d, 2 H, J =7.3 Hz), 1.063–0.903 (m, 1 H), 0.608–0.533 (m, 2 H), 0.270–0.208 (m, 2 H).

Example 146

6-(3-Chlorophenyl)-4-hydroxy-3-[(4-phenylbutyl) thio]-2H-pyran-2-one

The title compound (0.024 g, m.p. 123–124° C.) was prepared by method B using 6-(3-chlorophenyl)-4-hydroxy-2H-pyran-2-one (0.250 g, 1.13 mmol), 4-phenyl-butyl-p-toluenethiosulfonte (0.45 g, 1.93 mmol), triethylamine (0.115 g, 1.13 mmol), sodium bicarbonate (0.094 g, 1.13 mmol), ethanol (5.0 mL).$^{1}$H NMR (400 MHz, $CDCl_3$) δ7.848–7.839 (m, 1 H), 7.729 (m, 1 H), 7.479–7.392 (m, 2 H), 7.276–7.239 (m, 2 H), 7.174 –7.137 (m, 3 H), 6.631 (s, 1 H), 2.831–2.794 (t, 2 H), 2.633–2.596 (t, 2 H), 1.747–1.689 (m, 2 H), 1.649–1.591 (m, 2 H).

Example 147

4-Hydroxy-3-[(2-oxo-2-phenylethyl)thio]-6-phenyl-2H-pyran-2-one

A solution of 4-hydroxy-3-mercapto-6-phenyl-2-pyrone (0.175, 0.840 mmol, prepared as in R. F. Harris, J. E. Dunbar, U.S. Pat. No. 3,818,046) in $CH_2Cl_2$ (3.0 mL) under an $N_2$ atmosphere was treated with triethylamine (0.12 mL, 0.84 mmol) followed by bromoacetophenone (0.167 g, 0.840 mmol). The mixture was allowed to stir for 30 min. at ambient temperature then the solvent removed in vacuo. The residue was then diluted with diethyl ether and extracted with saturated $Na_2CO_3$ (3×50 mL). The aqueous layers were then combined, acidifed with conc. HCl, and extracted with $CH_2Cl_2$ (3×100 mL). The organic layers were combined, dried with $Na_2SO_4$, and the solvent removed in vacuo to give the title compound (0.066 g, m.p. 164–166 ° C.) which was dried in vacuo. $^1H$ NMR (300 MHz, $CDCl_3$) δ9.900 (bs, 1 H), 7.970 (d, 2 H, J=7.1 Hz), 7.810 (d, 2 H, J=8 Hz), 7.615 (t, 1 H, J =4 Hz), 7.505–7.443 (m, 5 H), 6.619 (s, 1 H), 4.334 (s, 2 H).

Example 148

4-Hydroxy-3-[(2-phenylethan-2-ol)thio]-6-phenyl-2H-pyran-2-one

To a stirred solution of 4-hydroxy-3-[(2-oxo-2-phenylethyl)thio]-6-phenyl-2H-pyran-2-one (0.021 g, 0.060 mmol) in THF (1.0 mL) cooled to 0° C. ($N_2$ atmosphere) was a 1.0 M solution of $BH_3$●DMS (0.05 mL, 0.05 mmol) in THF added via syringe. The mixture was allowed to stir for 1 h then quenched with a 1:1 mixture of 4 N HCl:MeOH. The mixture was then extracted with diethyl ether. The layers were combined, dried with $Na_2SO_4$, and the solvent removed in vacuo to provide the title compound (0.015 g) as an oil. $^1H$ NMR (200 MHz, $CDCl_3$) δ7.873–7.777 (m, 4 H), 7.516–7.153 (m, 6 H), 6.667 (s, 1 H), 4.820–4.755 (dd, 1 H, J=9.8 Hz,3.2 Hz), 3.212–3.127 (dd, 1 H, J=13.8 Hz, 3.2 Hz), 2.920 (dd, 1 H, J=9.8 Hz, 13.8 Hz).

Example 149

4-Hydroxy-5-methyl-6-phenyl-3-[phenylthio]-2H-pyran-2-one

A solution of propiophenone (1.50 mL, 11.3 mmol) in $CH_2Cl_2$ (40.0 mL) was cooled to 0° C. ($N_2$ atmosphere) and treated with triethylamine (3.14 mL, 22.6 mmol) followed by trimethylsilyltriflate (2.60 mL, 13.5 mmol). The solution was then warmed to ambient temperature, allowed to stir for 15 min., and subsequently quenched into a mixture of diethyl ether (50 mL) and saturated aqueous $NaHCO_3$ (20 mL). The layers were separated and the organic layer washed with a 1:1 mixture of brine:saturated $NaHCO_3$ (20 mL). The ethereal solution was then dried with $Na_2SO_4$ and the solvent removed in vacuo. The resulting silyl enol ether was then transferred to a flask containing diethyl -2-(thiophenyl)propane-1,3-dioate (1.00 g, 3.76 mmol), the mixture heated to 140° C. for 16 h. then allowed to cool to room temperature where it was diluted with diethylether and extraced with saturated $Na_2CO_3$ (3×20 mL). The aqueous layers were combined, washed with diethylether (3×75 mL), then carefully acidified with conc. HCl. The mixture was then extracted with $CH_2Cl_2$ (3×200 mL), the organic layers combined, dried with $Na_2SO_4$, and the solvent removed in vacuo to provide the title compound (0.350 g, m.p. 166 –167° C.). $^1H$ NMR (400 MHz, DMSO-$d_6$) δ6.309–6.285 (m, 2 H), 6.227–6.211 (m, 3 H), 5.983 (t, 2 H, J=8 Hz), 5.862 (d, 3 H, J=8 Hz), 0.705 (s, 3 H).

Example 150

[4- [4-Hydroxy-2-oxo-3- (phenylthio) -2H-pyran-6-yl]phenoxy]-acetic acid

A solution of methyl-[4-(1-oxoethyl)phenoxy]-acetate (2.50 g, 10.86 mmol) in $CH_2C1_2$ (25.0 mL) was cooled to 0° C. ($N_2$ atmosphere) and treated with triethylamine (3.03 mL, 21.7 mmol) followed by trimethylsilyltriflate (2.52 mL, 13.0 mmol). The solution was then warmed to ambient temperature, allowed to stir for 15 min., and subsequently quenched into a mixture of diethyl ether (50 mL) and saturated aqueous $NaHCO_3$ (20 mL). The layers were separated and the organic layer washed with a 1:1 mixture of brine:saturated $NaHCO_3$ (20 mL). The ethereal solution was then dried with $Na_2SO_4$ and the solvent removed in vacuo. The resulting silyl enol ether was then transferred to a flask containing diethyl 2-(thiophenyl)propane-1,3-dioate (0.97 g, 3.6 mmol). The mixture was then heated to 140° C. for 16 h. and allowed to cool to room temperature where it was submitted to chromatography ($SiO_2$-230 to 400 mesh, 100% $CH_2C1_2$ to 2.0% MeOH / $CH_2C1_2$) to provide an impure solid which was diluted with diethyl ether (20 mL) and extracted with saturated $Na_2CO_3$ (3×20 mL). The combined aqueous extracts were washed with diethyl ether (3×100 mL) and then acidifed with conc. HCl to pH 0. The mixture was then extracted with ethyl acetate (3×100 mL), the organic layers combined, dried with $Na_2SO_4$ and the solvent removed in vacuo. to provide the title compound (0.695 g, m.p. 186–188 ° C.). $^1H$ NMR (300 MHz, DMSO-$d_6$) δ13.175 (bs, 1 H), 12.425 (bs, 1 H), 7.809 (d, 2 H, J=9 Hz), 7.298–7.247 (m, 2 H), 7.149–7.004 (m, 5 H), 6.785 (s, 1 H), 4.804 (s, 2 H).

Example 151

[4-[4-Hydroxy-5-methyl-2-oxo-3-(phenylthio)-2H-pyran-6-yl]phenoxy]-acetic acid

The title compound (0.691 g, m.p. 194 - 197° C.) was prepared in a similar manner to that demonstrated in the preparation of [4-[4 -hydroxy-2-oxo-3- (phenylthio) -2H-pyran-6-yl]phenoxy]-acetic acid using the following: Methyl-[4-(1-oxoethyl)phenoxy]-acetate (2.00 g, 8.81 mmol), triethylamine (3.68 mL, 26.4 mmol), trimethylsilyltriflate (2.38 mL, 12.3 mmol), dichoromethane (20.0 mL), diethyl 2-(thiophenyl)propane-1,3-dioate (1.34 g, 5.00 mmol.), $^1H$ NMR (400 MHz, DMSO-$d_6$) δ7.585 (d, 2 H, J=9 Hz), 7.325–7.286 (m, 2 H), 7.178 (d, 3 H, J=7.5 Hz), 7.063 (d, 2 H, J=9 Hz), 4.784 (s, 2 H), 2.042 (s, 3 H).

Example 152

4-Hydroxy-3-phenoxy-6-phenyl-2H-pyran-2-one

To a is pressure reactor was added 2-phenoxypropanedioicacid diethylester 8.11 g (0.032 moles) and 1-phenyl-1-(trimethylsilyloxy)ethylene 12.35 g (0.064 moles). The vessel was pressurized to 600 psi with $N_2$. The mixture was heated at 100° C. for 8 hours then an additional 63.5 hours at 147–154° C. The vessel was cooled to room temperature and rinsed with ethyl acetate. Crude flash chromatography (hexane/ethyl acetate 1/1) afforded partially purified material which was then flashed on silica gel using hexane/ethyl acetate 95/5–40/60 as eluents. The resulting solid was recrystallized from diethyl ether and ethyl acetate to afford 1.64g (18%) of the title compound (mp=215–219° C.). $^1H$ NMR (400 MHz, DMSO-$d_6$) δ6.90 (s, 1 H), 6.95 (dd, 2 H), 7.02 (t, 1 H), 7.28–7.33 (m, 2 H), 7.52–7.56 (m, 3 H), 7.80–7.856 (m, 2 H), 12.0 (bs, 1 H).

Example 153

4-Hydroxy-3-[(phenylmethyl)thio]-6-(3-pyridinyl)-2H-pyran-2-one

The title compound was prepared from the condensation of the trimethylsilyl enol ether of 3-acetyl pyridine and diethyl ester of [(phenylmethyl)thio]propanedioic acid following the same procedure outlined in Method A; m.p. 183–184° C. NMR (DMSO-$d_6$) δ4.02 (s, 2 H), 6.83 (s, 1 H), 7.20 (m, 1 H), 7.26 (d, 4 H), 7.55 (m, 1 H), 8.16 (m, 1 H), 8.69 (m, 1 H), 8.98 (d, 1 H).

Example 154

6-(2,6-Dimethyl-4-pyridinyl)-4-hydroxy-3-[(phenylmethyl)thio]-2H-pyran-2-one

The title compound was prepared from the condensation of the trimethylsilyl enol ether of 4-acetyl-2,6-dimethylpyridine and the diethyl ester of [(phenylmethyl) thio]propanedioic acid following the same procedure outlined in Method A; m.p. 88–90° C. NMR (DMSO-d6) δ2.55 (s, 6 H), 4.02 (s, 2 H), 6.85 (s, 1 H), 7.16–7.28 (m, 5 H), 7.40 (s, 2 H).

Example 155

4-Hydroxy-3-[(phenylmethyl)thio]-6-(3-thienyl)-2H-pyran-2-one

The title compound was prepared from the condensation of the trimethylsilyl enol ether of 3-acetylthiophene and the diethyl ester of [(phenylmethyl)thio]propanedioic acid following the same procedure outlined in Method A; m.p. 150–151° C. NMR (DMSO-$d_6$) δ3.98 (s, 2 H), 6.58 (s, 1 H), 7.20 (m, 5 H), 7.48 (m, 1 H), 7.72 (m, 1 H), 8.13 (d, 1 H).

Example 156

3-[(2,6-Dimethylphenyl)methyl]thio]-4-hydroxy-6-phenyl-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), (2,6-dimethylphenyl)methyl p-toluenethiosulfonate (1.62 g, 5.31 mmol). m.p. 231–233° C.; $^1$H NMR (400 MHz, DMSO-$d_6$) δ2.34 (6H, s), 4.01 (s, 2H), 6.81 (m, 2H), 7.03 (m, 3H), 7.53 (m, 3H), 7.82 (m, 2H).

Example 157

4-Hydroxy-6-phenyl-3-[[(3-phenoxyphenyl)methyl] thio]-2H-pyran-2-one

The title compound was prepared by Method B using 4-hydroxy-6-phenyl-2H-pyran-2-one (1.00 g, 5.31 mmol), ethanol (15 mL), 1N sodium hydroxide (5.31 mL), (3-phenoxyphenyl)methyl p-toluenethiosulfonate (1.96 g, 5.31 mmol). m.p. 131–133° C.; $^1$H NMR (400 MHz, DMSO-$d_6$) δ3.97 (s, 2H) 6.73 (s, 1H), 6.87 (m, 4H), 7.03 (m, 2H), 7.27 (m, 3H), 7.53 (m, 3H), 7.78 (m, 2H).

Example 158

3-[1-[(Cyclohexylmethyl)thio]-3-methylbutyl]-4-hydroxy-6-phenyl-2H-pyran-2-one, (±)

The title compound was prepared by Method C using 4-hydroxy-6-pyran-2-one (1.00 g, 5.31 mmol), ethanol (10 mL), isovaleraldehyde (0.462 mL, 5.84 mmol), cyclohexylmethylthiol (1.79 g, 13.8 mmol), piperidine (0.5 mL), acetic acid (0.5 mL). m.p. 146–148° C.; $^1$H NMR (400 MHz, DMSO-$d_6$) δ0.58 (d, 6H), 1.11 (m, 5H), 1.57 (m, 8H), 2.07 (m, 1H), 2.28 (dd, 1H), 2.38 (dd, 1H), 4.17 (dd, 1H), 6.69 (s, 1H), 7.54 (m, 3H), 7.75 (m, 2H), 11.71 (bs, 1H).

Example 159

3-[1-[(Cyclohexylmethyl)thio]phenylmethyl]-4-hydroxy-6-phenyl-2E-pyran-2-one, (±)

The title compound was prepared by Method C using 4-hydroxy-6-phenyl-2H-pyran-2-one (1.00 g, 5.31 mmol), ethanol (10 mL), benzaldehyde (0.593 mL, 5.84 mmol), cyclohexylmethylthiol (1.79 g, 13.8 mmol), piperidine (0.5 mL), acetic acid (0.5 mL). m.p. 138–141° C.; $^1$H NMR (400 MHz, DMSO-$d_6$) δ0.89 (m, 2H), 1.21 (m, 3H), 1.42 (m, 1H), 1.61 (m, 3H), 1.75 (m, 2H), 2.39 (m, 2H), 5.30 (s, 1H), 6.71 (s, 1H), 7.26 (t, 1H), 7.28 (t, 2H), 7.53 (m, 5H), 7.74 (m, 2H).

Example 160

4-Hydroxy-6-[4-(2-hydroxyethoxy)phenyl]-3-[(2-phenylethyl) thio]-2H-pyran-2-one

To a tetrahydrofuran (7 mL) solution of [4-[4-hydroxy-2-oxo-3[(2-phenylethyl)thio]-2H-pyran-6-yl]-phenoxy] acetic acid, ethyl ester (0.30 g, 0.70 mmol) was added 2.0M lithium borohydride (0.5 mL, 1.00 mmol). The reaction was stirred overnight. The reaction was then quenched by addition of 1N hydrochloric acid (2.0 mL) and diluted with ethyl acetate (50 mL). The organic layer was separated and washed with saturated sodium chloride and dried over anhydrous magnesium sulfate. After evaporation of the solvents in vacuo, the crude product was purified by column chromatography (silica gel-230 to 400 mesh) using 50% ethyl acetate/hexanes to 100% ethyl acetate as the eluent. m.p. 123–125° C.; $^1$H NMR (400 MHz, DMSO-$d_6$) δ 2.77 (t, 2H), 2.97 (t, 2H), 3.37 (m, 2H), 4.07 (t, 2H), 4.92 (bs, 1H), 6.68 (s, 1H), 7.09 (d,2H), 7.19 (m, 5H), 7.75 (d, 2H).

Example 161

[3-[4-Hydroxy-2-oxo-3-[(2-phenylethyl)thio]-2H-pyran-6-yl]phenoxy] acetic acid, ethyl ester The title compound was prepared by Method A using ethyl (3-acetylphenoxy) acetate (2.00 g, 9.00 mmol), trimethyl silyltriflate (4.18 mL, 21.62 mmol), triethylamine (5.01 mL, 36.00 mmol), methylene chloride (23 mL), and diethyl ester of [(2-phenylethyl)thio]propanedioic acid (1.00 g, 3.37 mmol). m.p. 116–119° C.; $^1$H NMR (400 MHz, DMSO-$d_6$) δ 1.22 (t, 3H), 2.77 (t, 2H), 3.05 (t, 2H), 4.89 (d, 2H), 6.80 (s, 1H), 7.20 (m, 7H), 7.44 (m, 2H).

Example 162

4-Hydroxy-6-[4-[(5-methyl-3-phenyl-4-isoxazolyl) methoxy]phenyl]-3-[(2-phenylethyl)thio]-2H-pyran-2-one The title compound was prepared by Method A using 4'-[(5-methyl-3-phenyl-4-isoxaoly) methoxy]acetophenone (2.00 g, 6.51 mmol), trimethylsilyl triflate (1.51 mL, 7.81 mmol), triethylamine (1.81 mL, 13.02 mmol), methylene chloride (16 mL), and diethyl ester of [(2-phenylethyl) thio]propanedioic acid (1.00 g, 3.37 mmol). m.p. 126–128° C.; $^1$H NMR (400 MHz, DMSO-$d_6$) δ 6 2.54 (s, 3H), 2.77 (t, 2H), 2.98 (t, 2H), 5.08 (s, 2H), 6.69 (s, 1H), 7.21 (m, 7H), 7.49 (m, 3H), 7.71 (m, 2H), 7.77 (d, 2H).

Example 163

6-(3,5-Dimethylphenyl)-4-hydroxy-3-(phenylthio)-2H-pyran-2-one

The title compound was prepared by Method A using 3',5'-dimethylacetophenone (1.43 g, 9.70 mmol), trimethylsilyl triflate (2.24 mL, 11.64 mmol), triethylamine (2.70 mL, 19.40 mmol), methylene chloride (24 mL), and diethyl ester of (phenylthio)-propanedioic acid (1.00 g, 7.46 mmol). m.p. 210–211° C.; $^1$H NMR (400 MHz, DMSO-$d_6$) δ 2.35 (s, 6H), 6.83 (s, 1H), 7.12 (m, 3H), 7.21 (s, 1H), 7.27 (t, 2H), 7.46 (s, 2H).

Example 164

3-[1-[Cyclopentylthio]-2-cyclopropylethyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), cyclopropylmethylcarboxaldehyde (0.892 g, 10.62 mmol), cyclopentylthiol (1.43 mL, 13.8 mmol), piperidine (0.5 mL), acetic acid (0.5 mL). m.p.75–80° C.; $^{1}$H NMR (400 MHz, DMSO-$d_6$) δ0.04 (m, 2H), 0.07 (m, 2H), 0.66 (m, 1H), 1.53 (m, 7H), 1.94 (m, 3H), 3.19 (m, 1H), 4.21 (dd, 1H), 6.71 (s, 1H), 7.54 (m, 3H), 7.76 (m, 2H).

Example 165

N-[3-[4-Hydroxy-2-oxo-3-[(2-phenylethyl)thio]-2H-pyran-6-yl]phenyl]-4-methyl-benzenesulfonamide The title compound was prepared by Method A using 3'-(p-toluenesulfonamide) acetophenone (1.38 g, 5.06 mmol), trimethylsilyl triflate (2.34 mL, 12.41 mmol), triethylamine (2.82 mL, 20.24 mmol), methylene chloride (18 mL), and diethyl ester of [(2-phenylethyl)thio]propanedioic acid (1.00 g, 3.37 mmol). m.p. 133–135° C.; $^{1}$H NMR (400 MHz, DMSO-$d_6$) δ 2.32 (s, 3H), 2.77 (t, 2H), 3.09 (t, 2H), 6.68 (s, 1H), 7.19 (m, 6H), 7.40 (m, 4H), 7.53 (s, 1H), 7.67 (d, 2H), 10.50 (s, 1H), 12.03 (bs, 1H).

Example 166

3-[Cyclopentyl(cyclopentylthio)methyl]-4-hydroxy-6-phenyl-2H-pyran-2-one, (±)

The title compound was prepared by Method C using 4-hydroxy-6-phenyl-2H-pyran-2-one (1.00 g, 5.31 mmol), ethanol (10 mL), cyclopentanecarboxaldehyde (0.780 g, 7.96 mmol), cyclopentylthiol(1.43 mL, 13.8 mmol), piperidine (0.5 mL), acetic acid (0.5 mL). m.p.139–142° C.; $^{1}$H NMR (400 MHz, DMSO-$d_6$) δ 1.03 (m, 1H), 1.64 (m, 15H), 2.64 (m, 1H), 3.00 (m, 1H), 3.84 (d, 1H), 6.69 (s, 1H), 7.52 (m, 3H), 7.76 (m, 2H), 11.55 (bs, 1H).

Example 167

6-(1,1'-Biphen-3-yl)-4-hydroxy-3-[(2-isopropylphenyl) thio]-2H-pyran-2-one

The title compound was prepared by Method A using 3'-phenylacetophenone (0.946 g, 4.83 mmol), trimethylsilyl triflate (1.12 mL, 5.79 mmol), triethylamine (1.34 mL, 9.66 mmol), methylene chloride (17 mL), and diethyl ester of [(2 -isopropylphenyl)thio]-propanedioic acid (1.00 g, 3.22 mmol). m.p. 193–195° C.; ; $^{1}$H NMR (400 MHz, DMSO-$d_6$) δ 1.25 (d, 6H), 3.43 (m, 1H), 6.95 (d, 1H), 7.02 (s, 1H), 7.06 (t, 1H), 7.13 (t, 1H), 7.28 (d, 1H), 7.42 (t, 1H), 7.51 (t, 2H), 7.66 (t, 1H), 7.75 (d, 2H), 7.85 (t, 2H), 8.07 (s, 1H).

Example 168

4-Hydroxy-6-phenyl-3-[(2-propylphenyl)thio]-2H-pyran-2-one

The title compound was prepared by Method A using 1-phenyl-1-(trimethylsilyloxy)ethylene (0.990 mL, 4.83 mmol) and diethyl ester of [(2-propylphenyl)thio] propanedioic acid (1.00 g, 3.22 mmol). m.p. 158–160° C.; $^{1}$H NMR (400 MHz, DMSO-$d_6$) δ 0.972 (t, 3H), 1.64 (m, 2H), 2.71 (t, 2H), 6.87 (s, 1H), 6.92 (m, 1H), 7.06 (m, 2H), 7.16 (m, 1H), 7.55 (m, 3H), 7.85 (m, 2H).

Example 169

6-(3,5-Dimethylphenyl)-4-hydroxy-3-[(2-isopropylphenyl)- thio]-2H-pyran-2-one

The title compound was prepared by Method A using 3',5'-dimethylacetophenone (0.714 g, 4.83 mmol), trimethylsilyl triflate (1.12 mL, 5.79 mmol), triethylamine (1.34 mL, 9.66 mmol), methylene chloride (17 mL), and diethyl ester of [(2-isopropylphenyl)thio]propanedioic acid (1.00 g, 3.22 mmol) m.p. 154–155° C.; 1H NMR (400 MHz, DMSO-$d_6$) δ 1.24 (d, 6H), 2.35 (s, 6H), 3.40 (m, 1H), 6.90 (d, 1H), 7.05 (t, 1H), 7.11 (dt, 2H), 7.20 (s, 1H), 7.27 (d, 1H), 7.45 (s, 2H).

Example 170

4-Hydroxy-6-(4-hydroxyphenyl)-3-[(2-isopropylphenyl) thio]-2H-pyran-2-one

The title compound was prepared by Method A using 4'-hydroxyacetophenone (0.657 g, 4.83 mmol), trimethylsilyl triflate (2.05 mL, 10.62 mmol), triethylamine (2.69 mL, 19.32 mmol), methylene chloride (20 mL), and diethyl ester of [(2-isopropylphenyl)thio]propanedioic acid (1.00 g, 3.22 mmol) m.p. 250° C.; (dec.) ; $^{1}$H NMR (400 MHz, DMSO-$d_6$) δ 1.24 (d, 6H), 3.40 (m, 1H), 6.70 (s, 1H), 6.90 (t, 3H), 7.05 (t, 1H), 7.10 (t, 1H), 7.26 (d, 1H), 7.70 (d, 2H).

Example 171

3-[[2-(Cyclopropylmethyl)phenyl]thio]-4-hydroxy-6-phenyl-2H-pyran-2-one

The title compound was prepared by Method A using 1-phenyl-1-(trimethylsilyloxy)ethylene (0.990 mL, 4.83 mmol), and diethyl ester of [[2-(cyclopropylmethyl)phenyl] thio] propanedioic acid (1.00 g, 3.10 mmol) m.p. 165–167° C.; $^{1}$H NMR (400 MHz, DMSO-$d_6$) δ 0.25 (dd, 2H), 0.52 (dd, 2H), 1.21 (m, 1H), 2.50 (d, 2H), 6.87 (s, 1H), 6.92 (m, 1H), 7.05 (m, 2H), 7.32 (m, 1H), 7.56 (m, 3H), 7.86 (m, 2H).

Example 172

4-Hydroxy-3-[(2-isopropylphenyl) thio]-6-[4-(pyridin-3-ylmethoxy)phenyl]-2H-pyran-2-one The title compound was prepared by Method A using 4'-(pyridin-3-ylmethoxy)acetophenone (1.09 g, 4.83 mmol), trimethylsilyl triflate (1.12 mL, 5.79 mmol), triethylamine (1.34 mL, 9.66 mmol), methylene chloride (17 mL), and diethyl ester of [(2-isopropylphenyl)thio]-propanedioic acid (1.00 g, 3.22 mmol) m.p. 225° C.; ; $^{1}$H NMR (400 MHz, DMSO-$d_6$) δ 1.23 (d, 6H), 3.41 (m, 1H), 5.26 (s, 2H), 6.78 (s, 1H), 6.90 (d, 1H), 7.08 (dt, 2H), 7.21 (d, 2H), 7.29 (d, 1H), 7.45 (dd, 1H), 7.82 (d, 2H), 7.91 (d, 1H), 8.56 (d, 1H), 8.71 (s, 1H).

Example 173

4-[4-Hydroxy-5-[(2-isopropylphenyl)thio]-6-oxo-6H-pyran-2-yl]phenoxy acetic acid ethyl ester The title compound was prepared by Method A using ethyl (4-acetyl-phenoxy)acetate (2.14 g, 9.67 mmol), trimethylsilyl triflate (4.48 mL, 23.20 mmol), triethylamine (12.93 mL, 38.6 mmol), methylene chloride (20 mL), and diethyl ester of [(2-isopropylphenyl)thio]propanedioic acid (2.00 g, 6.45 mmol) m.p. 194–196° C.; ; $^{1}$H NMR (400 MHz, DMSO-$d_6$) δ 1.57 (m, 9H), 3.41 (m, 1H), 4.81 (q, 2H), 4.89 (s, 2H), 6.75 (s, 1H), 6.90 (d, 1H), 7.05 (m, 4H), 7.26 (d, 1H), 7.79 (d, 2H).

Example 174

4-[4-Hydroxy-5-[(2-isopropylphenyl)thio]-6-oxo-6H-pyran-2-yl]-phenoxy acetic acid To a tetrahydrofuran (10 ml) solution of 4-[4-Hydroxy-5-[(2-isopropylphenyl)thio]-6-oxo-6H-pyran-2-yl]phenoxy acetic acid ethyl ester (0.319 g. 0.75 mmol) was added 1N sodium hydroxide (1.80 mL, 1.81 mmol). The reaction was stirred for 1.5 h, and then water (10 ml) was added followed by acidification with conc. hydrochloric acid to pH 2. The aqueous layer was then extracted 2× with ethyl acetate (100 ml). the combined organic extracts were then washed with saturated sodium chloride and dried over anhydrous magnesium sulfate. After evaporation of the solvents in vacuo, the crude product was purified by column chromatography (silica gel-230 to 400 mesh) using 94/5/1 methylene chloride/methanol/acetic acid as the eluent. m.p. 217° C.; (dec.); $^{1}$H NMR (400 MHz, DMSO-$d_6$) δ 1.25 (d, 6H), 3.42 (m, 1H), 4.79 (s, 2H), 6.75 (s, 1H), 6.90 (d, 1H), 7.06 (m, 4H), 7.26 (d, 1H), 7.79 (d, 2H).

Example 175

4-Hydroxy-3-[(2-isopropylphenyl)thio]-6-(4-methoxyphenyl)-2H-pyran-2-one

The title compound was prepared by Method A using 4'-methoxyacetophenone (2.26 g, 15.1 mmol), trimethylsilyl triflate (3.5 mL, 18.1 mmol), triethylamine (4.26 mL, 30.6 mmol), methylene chloride (30 mL), and diethyl ester of [(2-isopropylphenyl)thio]propanedioic acid (3.11 g, 10.0 mmol) m.p. 221–223° C.; $^{1}$H NMR (400 MHz, DMSO-$d_6$) δ 1.25 (d, 6H), 3.40 (m, 1H), 3.85 (s, 3H), 6.78 (s, 1H), 6.92 (m, 1H), 7.10 (m, 4H), 7.27 (m, 1H), 7.81 (d, 2H), 12.38 (brs, 1H).

Example 176

4-Hydroxy-3-[(2-isopropylphenyl)thio]-6-(4-methylphenyl)-2H-pyran-2-one

The title compound was prepared by Method A using 4'-methylacetophenone (2.02 mL, 15.1 mmol), trimethylsilyl triflate (3.5 mL, 18.1 mmol), triethylamine (4.26 mL, 30.6 mmol), methylene chloride (30 mL), and diethyl ester of [(2-isopropylphenyl)thio]propanedioic acid (3.11 g, 10.0 mmol) m.p. 191–193° C.; $^{1}$H NMR (400 MHz, DMSO-$d_6$) δ 1.25 (d, 6H), 2.39 (s, 3H), 3.41 (m, 1H), 6.84 (s, 1H), 6.92 (m, 1H), 7.10 (m, 2H), 7.27 (m, 1H), 7.37 (m, 2H), 7.75 (d, 2H).

Example 177

6-(3,4-Dichlorophenyl)-4-hydroxy-3-[(2-isopropylphenyl)thio]-2H-pyran-2-one

The title compound was prepared by Method A using 3',4'-dichloroacetophenone (2.46 g, 12.8 mmol), trimethylsilyl triflate (3.0 mL, 15.4 mmol), triethylamine (3.6 mL, 26.0 mmol), methylene chloride (30 mL), and diethyl ester of [(2-isopropylphenyl)thio] propanedioic acid (4.0 g, 12.8 mmol) m.p. 204–207° C.; $^{1}$H NMR (400 MHz, $CDCl_3$) δ 1.33 (d, 6H), 3.55 (m, 1H), 6.71 (s, 1H), 7.00 (m, 1H), 7.08 (m, 1H), 7.20 (m, 1H), 7.30 (m, 1H), 7.56 (d, 1H), 7.69 (m, 1H), 7.74 (br, 1H), 7.98 (s, 1H).

Example 178

6-(4-Chlorophenyl)-4-hydroxy-3-[(2-isopropylphenyl)thio]-2H-pyran-2-one

The title compound was prepared by Method A using 4'-chloroacetophenone (2.33 g, 15.1 mmol), trimethylsilyl triflate (3.5 mL, 18.1 mmol), triethylamine (4.26 mL, 30.6 mmol), methylene chloride (30 mL), and diethyl ester of [(2-isopropylphenyl)thio] propanedioic acid (3.11 g, 10.0 mmol) m.p. 148–151° C.; $^{1}$H NMR (400 MHz, DMSO-$d_6$) δ 1.25 (d, 6H), 3.41 (m, 1H), 6.86 (s, 1H), 6.92 (m, 1H), 7.08 (m, 2H), 7.27 (m, 1H), 7.62 (m, 2H), 7.86 (m, 2H).

Example 179

4-[4-Hydroxy-5-[(2-isopropylphenyl)thio]-6-oxo-6H-pyran-2-yl]benzoic acid ethyl ester The title compound was prepared by Method A using ethyl 4-acetylbenzoate (2.93 g, 15.1 mmol), trimethylsilyl triflate (3.5 mL, 18.1 mmol), triethylamine (4.26 mL, 30.6 mmol), methylene chloride (30 mL), and diethyl ester of [(2-isopropylphenyl)thio]propanedioic acid (3.11 g, 10.0 mmol) m.p. 201–203° C.; $^{1}$H NMR (400 MHz, DMSO-$d_6$) δ 1.25 (d, 6H), 1.35 (t, 3H), 3.42 (m, 1H), 4.35 (q, 2H), 6.94 (m, 1H), 7.00 (s, 1H), 7.10 (m, 2H), 7.28 (m, 1H), 7.99 (m, 2H), 8.11 (m, 2H).

Example 180

4-Hydroxy-6-(3-hydroxyphenyl)-3-[(2-isopropylphenyl)thio]-2H-pyran-2-one

The title compound was prepared by Method A using 3'-hydroxyacetophenone (2.06 g, 15.1 mmol), trimethylsilyl triflate (7.0 mL, 36.2 mmol), triethylamine (8.52 mL, 61.1 mmol), methylene chloride (30 mL), and diethyl ester of [(2-isopropylphenyl)thio] propanedioic acid (3.11 g, 10.0 mmol) m.p. 201–204° C.; $^{1}$H NMR (250 MHz, DMSO-$d_6$) δ 1.25 (d, 6H), 3.41 (m, 1H), 6.82 (s, 1H), 6.93 (m, 2H), 7.09 (m, 2H), 7.30 (m, 4H), 9.91 (br, 1H).

Example 181

4-Hydroxy-3-[(2-isopropylphenyl)thio]-2H-6-(2-phenylethyl-1-ene)-pyran-2-one

The title compound was prepared by Method A using trans-4-phenyl-3-buten-2-one (2.23 g, 15.1 mmol), trimethylsilyl triflate (3.5 mL, 18.1 mmol), triethylamine (4.26 mL, 30.6 mmol), methylene chloride (30 mL), and diethyl ester of [(2-isopropylphenyl)thio] propanedioic acid (3.11 g, 10.0 mmol) m.p. 190–192° C.; $^{1}$H NMR (400 MHz, DMSO-$d_6$) δ 1.25 (d, 6H), 3.40 (m, 1H), 6.44 (s, 1H), 6.89 (m, 1H), 7.10 (m, 3H), 7.27 (m, 1H), 7.40 (m, 4H), 7.71 (d, 2H).

Example 182

6-(1,1'-Biphen-4-yl)-4-hydroxy-3-[(2-isopropylphenyl) thio]-2H-pyran-2-one

The title compound was prepared by Method A using 4-acetylbiphenyl (3.06 g, 15.1 mmol), trimethylsilyl triflate (3.5 mL, 18.1 mmol), triethylamine (4.26 mL, 30.6 mmol), methylene chloride (30 mL), and diethyl ester of [(2-isopropylphenyl)thio]propanedioic acid (3.11 g, 10.0 mmol) m.p. 203–206° C.; $^{1}$H NMR (250 MHz, DMSO-$d_6$) δ 1.26 (d, 6H), 3.40 (m, 1H), 6.94 (m, 2H), 7.10 (m, 2H), 7.28 (m, 1H), 7.51 (m, 3H), 7.77 (m, 2H), 7.91 (q, 4H).

Example 183

6-(1,1'-Biphenyl-3-yl)-4-hydroxy-3-[(naphthalen-2-yl)thio]-2H-pyran-2-one

The title compound was prepared by Method A using 3'-phenylacetophenone (2 g, 10.20 mmol), trimethylsilyl triflate (2.27 g, 10.20 mmol), triethylamine (2.06 g, 20.40 mmol), methylene chloride (20 mL), and diethyl ester of [2-(naphthalen-2-yl)thio]-propanedioic acid (1.62 g, 5.1 mmol). m.p. 183–185° C.; $^1$H NMR (400 MHz, DMSO-d6) δ 7.07 (s, 1H), 7.33 (dd, 1H), 7.39–7.58 (m, 5H), 7.66 (s, 1H), 7.69 (d, 1H), 7.78 (d, 1H), 7.81–7.92 (m, 6H), 8.11 (s, 1H).

Example 184

4-Hydroxy-3-[(naphthalen-1-yl)thio]-6-phenyl-2H-pyran-2-one

The title compound was prepared by Method A using 1-phenyl-1-(trimethylsilyloxy)ethylene (1.95 g, 10.14 mmol) and diethyl ester of [(1-naphthyl)thio]propanedioic acid (1.61 g, 5.07 mmol). m.p. 242–243° C.; $^1$H NMR (400 MHz, DMSO-$d_6$) δ 6.83 (s, 1H), 7.19 (d, 1H), 7.39 (t, 1H), 7.64–7.42 (m, 5H), 7.69 (d, 1H), 7.83 (m, 2H), 7.94 (d, 1H), 8.28 (d, 1H).

Example 185

6-(1,1'-Biphenyl-3-yl)-3-[[2-(cyclopropylmethyl)phenyl]thio]-4-hydroxy-2H-pyran-2-one The title compound was prepared by Method A using 3'-phenyl acetophenone (2 g, 10.20 mmol), trimethylsilyl triflate (2.27 g, 10.20 mmol), triethylamine (2.06 g, 20.40 mmol), methylene chloride (20 mL), and diethyl ester of [[2-(cyclopropylmethyl)phenyl]thio]propanedioic acid (1.14 g, 5.1 mmol). m.p. 88° C.; $^1$H NMR (400 MHz, DMSO-$d_6$) δ 0.25 (d, 2H), 0.53 (dd, 2H), 1.14 (m, 1H), 2.67 (d, 2H), 6.94 (m, 1H), 7.03 (s, 1H), 7.11 (m, 2H), 7.33 (m, 1H), 7.44 (d, 1H), 7.53 (t, 2H), 7.67 (t, 1H), 7.75 (d, 2H), 7.86 (m, 2H), 8.08 (s, 1H).

Example 186

3-[[2-(Cyclopropylmethyl)phenyl]thio]-6-(3,5-dimethyl -phenyl)-4-hydroxy-2H-pyran-2-one The title compound was prepared by Method A using 3,3'-dimethyl acetophenone (2 g, 13.51 mmol), trimethylsilyl triflate (3 g, 13.1 mmol), triethylamine (2.73 g, 27.02 mmol), methylene chloride (20 mL), and diethyl ester of [[2-(cyclopropylmethyl)phenyl]thio]propandioic acid (2.18 g, 6.76 mmol). m.p. 168° C.; $^1$H NMR (400 MHz, DMSO-$d_6$) δ 0.28 (d, 2H), 0.39 (dd, 2H), 1.13 (m, 1H), 2.26 (s, 6H), 2.67 (d, 2H), 6.85 (s, 1H), 6.92 (m, 1H), 7.11 (m, 2H), 7.22 (s, 1H), 7.33 (m, 1H), 7.47 (s, 2H).

Example 187

6-(1,1'-Biphenyl-3-yl)-4-hydroxy-3-[(2-isobutylphenyl) thio]-2H-pyran-2-one

The title compound was prepared by Method A using 3'-phenylacetophenone (2 g, 10.20 mmol), trimethylsilyl triflate (2.27 g, 10.20 mmol), triethylamine (2.06 g, 20.40 mmol), methylene chloride (20 mL), and diethyl ester of [(2-isobutylphenyl)thio]propanedioic acid (1.14 g, 5.1 mmol). m.p. 187–188° C. $^1$H NMR (400 MHz, DMSO-$d_6$) δ 0.83 (d, 6H), 1.78 (m, 1H), 2.4 (d, 2H), 7.03 (s, 1H), 7.08 (s, 4H), 7.44 (t, 1H), 7.53 (t, 2H), 7.67 (t, 1H), 7.75 (s, 1H), 7.78 (s, 1H), 7.86 (m, 2H), 8.08 (s, 1H).

Example 188

4-Hydroxy-3-[(2-isobutylphenyl)thio]-6-phenyl-2H-pyran-2-one

The title compound was prepared by Method A using 1-phenyl-1-(trimethylsilyloxy)ethylene (1.96 g, 10.20 mmol) and diethyl ester of [(2-isobutylphenyl)thio] propanedioic acid (1.64 g, 5.1 mmol). m.p. 195° C. $^1$H NMR (400 MHz, DMSO-$d_6$) δ 0.83 (d, 6H), 1.64 (m, 1H), 2.39 (d, 2H), 6.89 (s, 1H), 7.06 (s, 4H), 7.56 (m, 3H), 7.86 (m, 2H).

Example 189

4-Hydroxy-3-[(2-isopropylphenyl)thio]-6-[4-(pyridin-3-yl)phenyl]-2H-pyran-2-one

The title compound was prepared by using diethyl ester of [2-(isopropylphenyl)thio]-propanedioic acid (1 g, 3.22 mmol), trimethylsilyltriflate (1.18 g, 5.31 mmol), triethylamine (0.98 g, 9.66 mmol) and 3-(pyridin-3-yl) acetophenone (0.95 g, 4.83 mmol) as described by Method A. m.p.145–147° C. $^1$H NMR (400 MHz, DMSO-d6) δ 1.25 (d, 6H), 3.4 (m, 1H), 6.89 (s, 1H), 6.92 (d, 1H), 7.06 (m, 2H), 7.25 (d, 1H), 7.53 (m, 1H), 7.69 (t, 1H), 7.89 (d, 2H), 8.14 (s, 1H), 8.22 (d, 1H), 8.61 (brs, 1H), 8.97 (brs, 1H).

Example 190

4-Hydroxy-3-[(2-isopropylphenyl)thio]-6-(3-methylphenyl)-2H-pyran-2-one

The title compound was prepared by Method A using 3'-methylacetophenone (0.87 g, 6.46 mmol), trimethylsilyl triflate (1.44 g, 6.46 mmol), triethylamine (0.653 g, 6.46 mmol), methylene chloride (20 mL), and diethyl ester of [(2-isopropylphenyl)thio]propanedioic acid (1.0 g, 3.23 mmol). m.p. 161–162° C.; $^1$H NMR (400 MHz, DMSO-$d_6$) δ 1.25 (d, 6H), 2.39 (s, 3H), 3.42 (m, 1H), 6.86 (s, 1H), 6.92 (d, 1H), 7.07 (t, 1H), 7.13 (t, 1H), 7.28 (d, 1H), 7.39 (d, 1H), 7.4 (t, 1H), 7.64 (d, 1H), 7.67 (s, 1H).

Example 191

4-Hydroxy-3-(2-isopropylphenoxy)-6-phenyl-2H-pyran-2-one

The title compound was prepared by Method A using 1-phenyl-1-trimethylsilyloxy)ethylene (2.62 g, 13.6 mmol) and diethyl ester of 2-(isopropyl)phenoxy propanedioic acid (2.0 g, 6.8 mmol). $^1$H NMR (250 MHz, DMSO-$d_6$) δ 1.25 (d, 6H), 3.44 (m, 1H), 6.67 (d, 1H), 6.89 (s, 1H), 7.0 (t, 1H), 7.09 (t, 1H), 7.29 (d, 1H), 7.53 (m, 3H), 7.83 (m, 2H).

Example 192

6-(3-Chlorophenyl)-4-hydroxy-3-[(2-isopropylphenyl)thio]-2H-pyran-2-one

The title compound was prepared by Method A using 3'-chloroacetophenone (3 g, 19.41 mmol), trimethylsilyl triflate (4.31 g, 19.41 mmol), triethylamine (3.92 g, 38.82 mmol), methylene chloride (20 mL), and diethyl ester of [(2-isopropylphenyl)thio]-propanedioic acid (3.0 g, 9.71 mmol). Isolated yield: 70% m.p. 177–178° C.; $^1$H NMR (400 MHz, DMSO-$d_6$) δ 0.28 (d, 6H), 3.42 (m, 1H), 6.92 (d, 1H), 6.94 (s, 1H), 7.06 (t, 1H), 7.13 (t, 1H), 7.28 (d, 1H), 7.58 (t, 1H), 7.63 (t, 1H), 7.83 (d, 1H), 7.89 (s, 1H).

Example 193

6-(3,5-Dichlorophenyl)-4-hydroxy-3-[(2-isopropylphenyl)thio]-2H-pyran-2-one

The title compound was prepared by Method A using 3,5-dichloroacetophenone (2 g, 10.58 mmol), trimethylsilyl triflate (2.35 g, 10.58 mmol), triethylamine (2.14 g, 21.16 mmol), methylene chloride (20 mL), and diethyl ester of [(2-isopropylphenyl)thio]propanedioic acid (1.64 g, 5.29 mmol). Isolated yield: 70% m.p.168–169° C.; $^1$H NMR (400 MHz, DMSO-$d_6$) δ 1.25 (d, 6H), 3.42 (m, 1H), 6.92 (d, 1H), 7.01 (s, 1H), 7.06 (t, 1H), 7.13 (t, 1H), 7.28 (d, 1H), 7.83 (m, 1H), 7.88 (m, 2H).

Example 194

3-[(2,6-Dimethylphenyl)thio]-4-hydroxy-6-phenyl-2H-pyran-2-one

The title compound was prepared by Method A using 1-phenyl-1-(trimethylsilyloxy)ethylene (1.95 g, 10.14 mmol) and diethyl ester of [(2,6 dimethylphenyl)thio] propanedioic acid (2.0 g, 6.8 mmol) . m.p. 248–249° C.; $^1$H NMR (400 MHz, DMSO-$d_6$) δ2.47 (s, 6H), 6.75 (s, 1H), 7.08 (m, 3H), 7.39 (m, 3H), 7.78 (m, 2H).

Example 195

4-Hydroxy-3-[(2-methylphenyl)thio]-6-phenyl-2H-pyran-2-one

The title compound was prepared by Method A using 1-phenyl-1-(trimethylsilyloxy)ethylene (1.95 g, 10.14 mmol) and diethyl ester of [(2-methylphenyl)thio] propanedioic acid (1.43 g, 5.07 mmol). m.p. 210–211° C.; $^1$H NMR (400 MHz, DMSO-$d_6$) δ2.47 (s, 3H), 6.82 (s, 1H), 6.86 (d, 1H), 7.04 (m, 2H), 7.17 (d, 1H), 7.56 (m, 3H), 7.86 (m, 2H).

Example 196

3-(2,6-Dichlorophenyl)thio]-4-hydroxy-6-phenyl-2H-pyran-2-one

The title compound was prepared by Method A using 1-phenyl-1-(trimethylsilyloxy)ethylene (1.72 g, 8.93 mmol) and diethyl ester of [(2,6-dichlorophenyl)thio]propanedioic acid (1.5 g, 4.46 mmol) . m.p. 264–265° C.; $^1$H NMR (400 MHz, DMSO-$d_6$) δ6.75 (s, 1H), 7.31(t, 1H), 7.49 (d, 2H), 7.56 (m, 3H), 7.78 (m, 2H).

Example 197

4-[5-(1-Cyclopentylthio-3-methylbutyl)-4-hydroxy-6-oxo-6H-pyran-2-yl]benzoic acid ethyl ester (±)

The title compound was prepared by Method C using 4-hydroxy-6-(4'-carbethoxyphenyl)-2H-pyran-2-one (1.50 g, 5.77 mmol), ethanol (15 mL), isovalaraldehyde (0.497 g, 5.77 mmol), cyclopentylthiol (1.18 g, 11.54 mmol), piperidine (1.0 mL), acetic acid (1.0 mL). m.p. 174–176° C; $^1$H NMR (400 MHz, DMSO-$d_6$) δ1.05–0.72 (m, 10H), 1.81–1.14(m, 7H), 2.13–1.81(m, 3H), 3.04 (t, 1H), 4.22 (m, 1H), 4.36 (q, 2H), 6.8 (s, 1H), 7.90 (d, 1H), 7.97 (q, 1H), 8.15 (m, 2H).

Example 198

3-[[(Benzylthio)pyridin-3-yl]methyl]-4-hydroxy-6-phenyl-2H-pyran-2-one (±)

The title compound was prepared by Method C using 4-hydroxy-6-phenyl-2H-pyran-2-one (1.50 g, 7.98 mmol), ethanol (10 mL), pyridine-3-carboxaldehyde (0.86 g, 7.98 mmol), benzylmercaptan (1.98g, 15.96 mmol), piperidine (0.5 mL), acetic acid (0.5 mL). m.p. 103–106° C.; $^1$H NMR (400 MHz, DMSO-$d_6$) δ3.75 (q, 2H), 5.31 (s, 1H), 6.33 (s, 1H), 7.2 (m, 1H), 7.28 (m, 5H), 7.36 (m, 3H), 7.72 (m, 2H), 7.89 (d, 1H), 8.38 (dd, 1H), 8.57 (s, 1H).

Example 199

3-(1-Cyclopentylthio-2-cyclopropylethyl)-6-(2,3-dihydrobenzo[1,4]dioxin-6-yl)-4-hydroxy-2H-pyran-2-one (±)

The title compound was prepared by Method C using 4-hydroxy-6-(2,3-dihydrobenzo[1,4]dioxin-6-yl)-2H-pyran-2-one (1.00 g, 4.06 mmol), ethanol (15 mL), cyclopropylmethylcarboxaldehyde (0.34 g, 4.06 mmol), cyclopentylthiol (0.83 g, 8.12 mmol), piperidine (1.0 mL), acetic acid (1.0 mL). m.p. 80–82° C.; $^1$H NMR (400 MHz, DMSO-$d_6$) δ0.03 (m, 2H), 0.33 (m, 2H), 0.64 (m, 1H), 1.28–1.74 (m, 7H), 1.83–2.06 (m, 3H), 3.06 (m, 1H), 4.2 (m, 1H), 4.31 (m, 4H), 6.53 (s, 1H), 7.0 (d, 1H), 7.24 (d, 1H), 7.24 (dd, 2H).

Example 200

4-[[(4-Hydroxy-6-oxo-5-[(phenylethyl)thio]-6H-pyran-2-yl)-phenoxy]methyl]benzoic acid To a dioxane (20 mL) solution of 4-[[4-hydroxy-2-oxo-3-[(2-phenylethyl)thio]-2H-pyran-6-yl]phenoxy]methyl] benzoic acid methyl ester (0.25 g) was added 2N sodium hydroxide, followed by methanol to keep the reaction homogeneous. Reaction was stirred at room temperature for 24 h. Solvents were evaporated. The residue was acidified with 3N hydrochloric acid. The precipitate formed was filtered and washed with ether and dried under vacuum. m.p. 227° C.; $^1$H NMR (400 MHz, DMSO-$d_6$) δ2.78 (t, 2H), 2.97 (t, 2H), 5.29 (s, 2H), 6.72 (s, 1H), 7.14–7.32(m, 7H), 7.58 (d, 2H), 7.78 (d, 2H), 7.97 (d, 2H).

Example 201

4-(4-Hydroxy-6-oxo-5-[(2-phenylethyl)thio]-6H-pyran-2-yl)benzoic acid ethyl ester The title compound was prepared by Method A using 4-carboethoxy acetophenone (3 g, 15.61 mmol), trimethylsilyl triflate (3.47 g, 15.61 mmol), triethylamine (3.16 g, 31.22 mmol), methylene chloride (20 mL), and diethyl ester of [2-(phenylethyl)thio]-propanedioic acid (2.31 g, 7.81 mmol). m.p. 156–158° C. $^1$H NMR (400 MHz, DMSO-$d_6$) δ1.36 (t, 3H), 2.78 (t, 2H), 3.01 (t, 2H), 4.35 (q, 2H), 6.86 (s, 1H), 7.11–7.28 (m, 5H), 7.92 (d, 2H), 8.08 (d, 2H).

Example 202

4-(4-Hydroxy-6-oxo-5-[(2-phenylethyl)thio]-6H-pyran-2-yl)benzoic acid

The compound 4-(4-hydroxy-6-oxo-5-(2-phenylethyl) thio-6H-pyran-2-yl)benzoic acid ethyl ester (0.2 g) was saponified as described in example 200. m.p. 231° C. $^1$H NMR (400 MHz, DMSO-$d_6$) δ2.94 (t, 2H), 3.03 (t, 2H), 6.64 (s, 1H), 7.11–7.33 (m, 5H), 7.92 (d,1H), 7.99 (d,1H), 8.05 (d,1H), 8.08 (d,1H).

Example 203

6-(2,3-Dihydrobenzo[1,4]dioxin-6-yl)-4-hydroxy-3-[(2-isopropylphenyl)thio]-2H-pyran-2-one The title compound was prepared by Method A using 1,4-benzodioxin-6-yl methyl ketone (2 g, 11.22 mmol), trimethylsilyl triflate (2.5 g, 11.22 mmol), triethylamine (2.27 g, 22.44 mmol), methylene chloride (20 mL), and diethyl ester of [(2-isopropylphenyl)thio]propanedioic acid (1.73 g, 5.61 mmol). m.p. 246–248° C.; $^1$H NMR (400 MHz, DMSO-$d_6$) δ1.25 (d, 6H), 3.4 (m, 1H), 4.32 (m, 4H), 6.72 (s, 1H), 6.89 (d, 1H), 7.01 (d, 1H), 7.06 (t, 1H), 7.11 (t, 1H), 7.26 (d,1H), 7.31 (d, 1H), 7.35 (dd, 1H).

Example 204

3-(1-Benzylthio-3-methylbutyl)-6-(2,3-dihydrobenzo [1,4]dioxin-6-yl)-4-hydroxy-2H-pyran-2-one (±)

The title compound was prepared by Method C using 4-hydroxy-6-(2,3-dihydrobenzo[1,4]dioxin-6-yl)-2H-pyran-2-one (1.00 g, 4.06 mmol), ethanol (15 mL), isovaleraldehyde (0.35 g, 4.06 mmol), benzylmercaptan (1.0 g, 8.12 mmol), piperidine (0.5 mL), acetic acid (0.5 mL). $^1$H NMR (400 MHz, DMSO-$d_6$) δ0.78 (t, 6H), 1.36 (m, 1H), 1.5 (m, 1H), 2.06 (m, 1H), 4.2 (m, 1H), 4.31 (brm, 6H), 6.56 (s, 1H), 7.03 (d, 2H), 7.36–7.25 (m, 6H).

Example 205

3-[[(Cyclohexylthio)pyridin-4-yl]methyl]-4-hydroxy-6-phenyl-2H-pyran-2-one(±)

The title compound was prepared by Method C using 4-hydroxy-6-phenyl-2H-pyran-2-one (1.5 g, 7.98 mmol), ethanol (10 mL), pyridine-4-carboxaldehyde (0.86 g, 7.98 mmol), cyclohexylthiol (1.86 g, 7.98 mmol), piperidine (0.5 mL), acetic acid (0.5 mL). $^1$H NMR (400 MHz, DMSO-$d_6$) δ1.25 (m, 5H), 1.53 (m, 1H), 1.67 (m, 2H), 1.92 (m, 2H), 2.71 (m, 1H), 5.33 (s, 1H), 6.69 (s, 1H), 7.5 (m, 5H), 7.75 (m, 2H), 8.47 (d, 2H).

Example 206

3-[[(Cyclohexylthio)pyridin-3-yl]methyl]-4-hydroxy-6-phenyl-2H-pyran-2-one (±)

The title compound was prepared by Method C using 4-hydroxy-6-phenyl-2H-pyran-2-one (1.5 g, 7.98 mmol), ethanol (10 mL), pyridine-3-carboxaldehyde (0.86g, 7.98 mmol), cyclohexylthiol (1.86g, 7.98 mmol), piperidine (0.5 mL), acetic acid (0.5 mL). $^1$H NMR (400 MHz, DMSO-$d_6$) δ1.25 (m, 5H), 1.53 (m, 1H), 1.67 (m, 2H), 1.92 (m, 2H), 2.69 (m, 1H), 5.39 (s, 1H), 6.72 (s, 1H), 7.33 (m, 1H), 7.53 (m, 3H), 7.73 (m, 2H), 7.97 (d, 1H), 8.39 (d, IH), 8.67 (d, 1H).

Example 207

4-[[(4-Hydroxy-2-oxo-6-phenyl-2H-pyran-3-yl)thio] methyl]benzoic acid

The title compound was prepared by the saponification of methyl ester of 4-[[(4-hydroxy-2-oxo-6-phenyl-2H-pyran-3-yl)thio]methyl]benzoic acid (0.1 g) as described in Example 200. $^1$H NMR (400 MHz, DMSO-$d_6$) δ4.06 (s, 2H), 6.72 (s, 1H), 7.36 (d, 2H), 7.58 (m, 3H), 7.86 (m, 4H).

Example 208

3-[[(4-Hydroxy-2-oxo-6-phenyl-2H-pyran-3-yl)thio] methyl]benzoic acid

The title compound was prepared by the saponification of methyl ester of 3-[[(4-hydroxy-2-oxo-6-phenyl-2H-pyran-3-yl)thio]methyl]benzoic acid (0.1 g) as described in Example 200. $^1$H NMR (400 MHz, DMSO-$d_6$) δ4.4 (d, 1H), 4.72 (d, 1H), 6.72 (s, 1H), 7.4 (t, 1H), 7.44–7.61(m, 5H), 7.74–7.92 (m, 4H).

Example 209

2-[[(4-Hydroxy-2-oxo-6-phenyl-2H-pyran-3-yl)thio] methyl]benzoic acid

The title compound was prepared by the saponification of methyl ester of 2-[[(4-hydroxy-2-oxo-6-phenyl-2H-pyran-3-yl)thio]methyl]benzoic acid (0.2 g) as described in Example 200. $^1$H NMR (400 MHz, DMSO-$d_6$) δ4.36 (s, 2H), 6.69 (s, 1H), 7.18 (d, 1H), 7.29 (t, 1H), 7.39 (t, 1H), 7.53 (m, 3H), 7.79 (m, 3H).

Example 210

3-[(2-Chlorophenyl)thio]-4-hydroxy-6-phenyl-2H-pyran-2-one

The title compound was prepared by Method A using 1-phenyl-1-(trimethylsilyloxy)ethylene (1.95 g, 10.14 mmol) and diethyl ester of [(2-chlorophenyl)thio] propanedioic acid (1.53 g, 5.07 mmol). m.p. 275–280° C.; $^1$H NMR (400 MHz, DMSO-$d_6$) δ6.78 (s, 1H), 6.89 (dd, 1H), 7.08 (tt, 1H), 7.19 (tt, 1H), 7.42 (dd, 1H), 7.56 (m, 3H), 8.06 (m, 2H).

Example 211

4-Hydroxy-3-[(2-methoxyphenyl)thio]-6-phenyl-2H-pyran-2-one

The title compound was prepared by Method A using 1-phenyl-1-(trimethylsilyloxy)ethylene (1.95 g, 10.14 mmol) and diethyl ester of [(2-methoxyphenyl)thio] propanedioic acid (1.51 g, 5.07 mmol). m.p.208–209° C.; $^1$H NMR (400 MHz, DMSO-$d_6$) δ3.83 (s, 3H), 6.74 (dd, 1H), 6.82 (d, 1H), 6.86 (s, 1H), 6.97 (d, 1H), 7.08 (t, 1H), 7.56 (m, 3H), 7.86 (m, 2H).

Example 212

6-(4-Benzyloxyphenyl)-4-hydroxy-3-[(2-isopropyl-phenyl)thio]-2H-pyran-2-one

The title compound was prepared by Method A using 4-benzyloxyacetophenone (0.3 g, 0.675 mmol), trimethylsilyl triflate (0.15 g, 0.675 mmol), triethylamine (0.14 g, 1.35 mmol), methylene chloride (20 mL), and diethyl ester of [(2-isopropylphenyl)thio]propanedioic acid (0.210 g, 0.675 mmol). m.p. 163–165° C.; $^1$H NMR (400 MHz, DMSO-$d_6$) δ1.28 (d, 6H), 3.4 (m, 1H), 5.22 (s, 2H), 6.64(s,1H), 6.92 (d, 1H), 7.06 (t, 1H), 7.11(t, 1H), 7.19 (d, 1H), 7.28 (d, 1H), 7.36 (q, 2H), 7.42 (d, 2H), 7.49 (d, 2H), 7.83 (d, 2H).

Example 213

3-[(3-Chlorophenyl)thio]-4-hydroxy-6-phenyl-2H-pyran-2-one

The title compound was prepared by Method A using 1-phenyl-1-(trimethylsilyloxy)ethylene (1.95 g, 10.14 mmol) and diethyl ester of [(3-chlorophenyl)thio] propanedioic acid (1.53 g, 5.07 mmol). m.p.181–182° C.; $^1$H NMR (400 MHz, DMSO-$d_6$) δ6.88 (s, 1H), 7.13 (dt, 2H), 7.19 (dt, 1H), 7.29 (t, 1H), 7.56 (m, 3H), 7.86 (m, 2H).

Example 214

4-Hydroxy-3-[ (3-methoxyphenyl)thio]-6-phenyl-2H-pyran-2-one

The title compound was prepared by Method A using 1-phenyl-1-(trimethylsilyloxy)ethylene (1.95 g, 10.14 mmol) and diethyl ester of [(3-methoxyphenyl)thio] propanedioic acid (1.51 g, 5.07 mmol). m.p. 130–131° C. $^1$H NMR (400 MHz, DMSO-$d_6$) δ3.69 (s, 3H), 6.69 (dd, 1H), 6.72 (dd, 1H), 6.89 (s, 1H), 7.2 (dt, 2H), 7.58 (m, 3H), 7.88 (m, 2H).

Example 215

4-Hydroxy-3-[(3-methylphenyl)thio]-6-phenyl-2H-pyran-2-one

The title compound was prepared by Method A using 1-phenyl-1-(trimethylsilyloxy)ethylene (1.95 g, 10.14 mmol) and diethyl ester of [(3-methylphenyl)thio] propanedioic acid (1.43 g, 5.07 mmol). m.p. 197–198° C.; $^1$H NMR (400 MHz, DMSO-$d_6$) δ2.24 (s, 3H), 6.89 (s, 1H), 6.93 (t, 1H), 6.97 (s, 1H), 7.14 (t, 2H), 7.56 (m, 3H), 7.86 (m, 2H).

Example 216

3-[(2-Ethylphenyl)thio]-4-hydroxy-6-phenyl-2H-pyran-2-one

The title compound was prepared by Method A using 1-phenyl-1-(trimethylsilyloxy)ethylene (4.17 g, 21.72 mmol) and diethyl ester of [(2-ethylphenyl)thio] propanedioic acid (1.5 g, 10.86 mmol). m.p. 190–192° C.; $^1$H NMR (400 MHz, DMSO-$d_6$) δ1.25 (t, 3H), 2.78 (q, 2H), 6.89 (s, 1H), 6.92 ( m, 1H), 7.08 (m, 2H), 7.2 (m, 1H), 7.58 (m, 3H), 7.86 (m, 2H).

Example 217

Acetic acid 3-[(2-isopropylphenyl)thio]-2-oxo-6-phenyl-2H-pyran-4-yl ester

This compound was prepared by the treatment of sodium salt of 4-hydroxy-3-[2-isopropylphenyl)thio]-6-phenyl-2H-pyran-2-one (0.2 g, 0.59 mmol) with acetyl chloride (0.09 g, 1.18 mmol) as described in general procedure G. m.p. 113–115° C.; $^1$H NMR (400 MHz, DMSO-$d_6$) δ1.26 (d, 6H), 1.89 (s, 3H), 3.42 (m, 1H), 6.89 (s, 1H), 6.94 (dd, 1H), 7.04 (dt, 1H), 7.13 (dt, 1H), 7.28 (dd, 1H), 7.58 (m, 3H), 7.86 (m, 2H).

Example 218

4-Hydroxy-6-phenyl-3-[(3-trifluoromethylphenyl) thio]-2H-pyran-2-one

The title compound was prepared by Method A using 1-phenyl-1-(trimethylsilyloxy)ethylene (1.72 g, 8.92 mmol) and diethyl ester of [[3-(trifluoromethyl)phenyl]thio] propanedioic acid (1.5 g, 4.46 mmol). m.p. 228–229° C.; $^1$H NMR (400 MHz, DMSO-$d_6$) δ6.89 (s, 1H), 7.4–7.61 (m, 7H), 7.89 (m, 2H).

Example 219

3-[3,5-Dimethylphenyl)thio]-4-hydroxy-6-phenyl-2H-pyran-2-one

The title compound was prepared by Method A using 1-phenyl-1-(trimethylsilyloxy)ethylene (1.3 g, 6.76 mmol) and diethyl ester of [(3,5-dimethylphenyl)thio]propanedioic acid (1.0 g, 3.38 mmol). m.p. 214–216° C.; $^1$H NMR (400 MHz, DMSO-$d_6$) δ2.2 (s, 6H), 6.75 (brs, 3H), 6.89 (s, 1H), 7.56 (m, 3H), 7.86 (m, 2H).

Example 220

6-[4-(Cyclohexylmethoxy)phenyl]-4-hydroxy-3-[(2-isopropylphenyl)thio]-2H-pyran-2-one The title compound was prepared by Method A using 4-cyclohexylmethoxy acetophenone (2.0 g, 8.61 mmol), trimethylsilyl triflate (1.91 g, 8.61 mmol), triethylamine (1.74 g, 17.22 mmol), methylene chloride (20 mL), and diethyl ester of [(2-isopropylphenyl)thio]propanedioic acid (4.0 g, 12.92 mmol). m.p. 187–188° C.; $^1$H NMR (400 MHz, DMSO-$d_6$) δ0.96–1.33 (m+1.24 d 11H), 1.61–1.87 (m, 6H), 3.4 (m, 1H), 3.86 (d, 2H), 6.76 (s, 1H), 6.92 (dd, 1H), 7.11 (m, 4H), 7.29 (dd, 1H), 7.81 (d, 2H).

Example 221

6-(3-Benzyloxyphenyl)-4-hydroxy-3-(2-isopropylphenyl)thio]-2H-pyran-2-one

The title compound was prepared by Method A using 3-benzyloxyacetophenone (2.0 g, 8.84 mmol), trimethylsilyl triflate (1.96 g, 8.84 mmol), triethylamine (1.79 g, 17.68 mmol) and diethyl ester of [(2-isopropylphenyl)thio] propanedioic acid (0.210 g, 0.675 mmol). m.p. 162–164° C.; $^1$H NMR (400 MHz, DMSO-$d_6$) δ1.25 (d, 6H), 3.42 (m, 1H), 5.35 (s, 2H), 6.89 (s, 1H), 6.92 (d, 1H), 7.06 (dt, 1H), 7.11 (dt, 1H), 7.22 (dd, 1H), 7.28 (dd, 1H), 7.39–7.51(m, 8H).

Example 222

4-Hydroxy-3-[(2-isopropylphenyl)thio]-6-[4-(3-phenylpropoxy)phenyl]-2H-pyran-2-one The title compound was prepared by Method A using 4-phenylpropyloxy acetophenone (2.0 g, 7.86 mmol), trimethylsilyl triflate (1.75 g, 7.86 mmol), triethylamine (1.59 g, 15.72 mmol) and diethyl ester of [(2-isopropylphenyl)thio]-propanedioic acid (3.66 g, 11.79 mmol). m.p. 132–133° C.; $^1$H NMR (400 MHz, DMSO-$d_6$) δ1.25 (d, 6H), 2.06 (m, 2H), 2.75 (t, 2H), 3.39 (m, 1H), 4.08 (t, 2H), 6.78 (s, 1H), 6.90 (d, 1H), 7.05 (dt, 2H), 7.08 (q, 2H), 7.11–7.31 (m, 6H), 7.81 (d, 2H).

Example 223

3-[ (2-sec-Butylphenyl)thio]-4-hydroxy-6-phenyl-2H-pyran-2-one (±)

The title compound was prepared by Method A using 1-phenyl-1-(trimethylsilyloxy)ethylene (1.0 g, 6.17 mmol) and diethyl ester of [(2-sec-butylphenyl)thio]propanedioic acid (1.0 g, 3.09 mmol). m.p. 170–171° C.; $^1$H NMR (400 MHz, DMSO-$d_6$) δ0.86(t, 3H), 1.22 (d, 3H), 1.57 (m, 1H), 1.67 (m, 1H), 3.22 (m, 1H), 6.89 (s, 1H), 6.97 (d, 1H), 7.06 (t, 1H), 7.13 (t, 1H), 7.22 (d, 1H), 7.56 (m, 3H), 7.86 (m, 2H).

4.5 Determination of HIV Protease Inhibition 4.5.1 Starting Materials

DTT Buffer: 1.0 mM dithiothreitol (DTT) was prepared fresh daily in 0.1% polyethylene glycol (mw 8000) 80 mM NaOAc, 160 mM NaCl, 1.0 mM EDTA, and brought to pH 4.7 with HCl.

HIV-I Protease: The enzyme is obtained from Bachem Bioscience Inc. The undiluted enzyme is thawed from −80° C. and diluted 50-fold with DTT buffer. The solution is always kept at 0° C. on ice water and used in the experiment within 20 minutes after thawing.

Enzyme Substrate: Substrate III from Bachem Bioscience Inc. is the undecapeptide H-His-Lys-Ala-Arg-Val-Leu-p-Nitrophenylalanine-Glu-Ala-Norleucine-Ser-NH2 (>97% purity). A 200 μM stock solution in DTT buffer is prepared and stored on ice. Substrate solution is prepared fresh daily.

Test Compound: 10 mM inhibitor (I) in dimethyl sulfoxide (DMSO) is diluted to 200 μM with DTT buffer. From the 200 μM stock solution is made a 10 μM stock solution with 2% DMSO in DTT buffer. The two inhibitor solutions are used to make final [I] =100, 50, 20, 10, 5, 2, 1, 0.5 and 0 μM with 2% DMSO in DTT buffer in each reaction well (total inhibitor volume of 50 μl).

4.5.2 Assay

To each reaction well is added 20 μl of substrate (final concentration of 40 μM), 50 μl of inhibitor (at a concentration such that final dilution will produce the test concentration) and 20 μl of DTT buffer. The reaction plate (96 wells) is incubated at 37° C. for at least 5 minutes.

10 μl of the diluted protease is added to the reaction well while the reaction plate is shaking. Once shaken for 10 seconds, the plate is returned to the heating block at 37° C. (Final reaction volume=100 μl.)

The reaction is incubated for 5 minutes at 37° C. The reaction is stopped by placing the reaction plate on the shaker and adding 20 μl of 10% trifluoroacetic acid (TFA) and shaking for 10 seconds. The amount of proteolysis is then determined by separation of noncleaved substrate and two cleaved products with reverse-phase HPLC, while measuring absorbance at 220 nm to determine the relative peak areas of the three components. The relative peak areas are used to calculate % conversion to product as a function of inhibitor concentration. The data is plotted as % Control (the ratio of % conversion in the presence and absence of inhibitor ×100) versus inhibitor concentration and fit with the equation Y=100/1+(X/IC50 is the inhibitor concentration at 50% inhibition and A is the slope of the inhibition curve.

TABLE 1

HIV Protease Inhibition Results

| Example # | 50% Inhibition Concentration (Averaged) [μM] |
|---|---|
| 1 | 0.47 |
| 3 | 1.0 |
| 4 | 0.9 |
| 6 | 0.4 |
| 8 | 1.7 |
| 17 | 0.69 |
| 23 | 1.7 |
| 26 | 1.2 |
| 27 | 0.5 |
| 28 | 1.9 |
| 29 | 0.33 |
| 33 | 1.97 |
| 34 | 0.8 |
| 44 | 0.75 |
| 48 | 0.86 |
| 49 | 1.6 |
| 52 | 0.7 |
| 64 | 0.6 |
| 68 | 0.45 |
| 70 | 0.13 |
| 71 | 1.9 |
| 73 | 0.77 |
| 74 | 0.61 |
| 77 | 0.14 |
| 78 | 1.5 |
| 87 | 0.41 |
| 110 | 0.07 |
| 113 | 0.24 |
| 121 | 0.48 |
| 129 | 0.20 |
| 133 | 0.06 |
| 144 | 0.037 |

TABLE 1-continued

HIV Protease Inhibition Results

| Example # | 50% Inhibition Concentration (Averaged) [μM] |
|---|---|
| 160 | 0.36 |
| 163 | 0.63 |
| 164 | 0.055 |
| 166 | 0.23 |
| 169 | 0.015 |
| 172 | 0.068 |
| 183 | 0.41 |
| 193 | 0.026 |

4.6 Anti-HIV-1 Activity

Using the general methods of Pauwels et al., (*J. Virol. Methods,* 16, 171–185, 1987) and Mann et al. (*AIDS Research and Human Retroviruses,* 253–255, 1989) anti-viral assays of acute HIV-1 infection were performed in the H9 cell line. Cultures were batch infected in 1 ml of RPM1 1640 media/10% fetal calf serum containing $10^7$ cells and $10^5$ infectious doses of HIV-$1_{iiib}$ for an effective multiplicity of infection of 0.01. After 2 hours of viral absorption, cells were washed once and plated in 96-well microtiter plates at a density of $10^4$ cells per well. Test compounds were added to produce the desired concentration of drug and 0.2% DMSO in a final volume of 200 μl. Uninfected parallel cultures were maintained for XTT cytotoxicity assay at 7 days post infection. Cultures were tested for viral replication by reverse transcriptase assay at 4 and 7 days post infection.

TABLE 2

Antiviral Activity in H9 Cells

| Example # | Concentration for 50% Protection [μM] |
|---|---|
| 29 | 17 |
| 70 | 29 |
| 78 | 3 |
| 87 | 15 |
| 121 | 15 |
| 166 | 14 |
| 169 | 31 |
| 172 | 0.65 |

Combinations of protease inhibitor with other AIDS treatments, such as (but not limited to) the HIV reverse transcriptase inhibitors AZT or ddC, may produce synergistic results. J. C. Craig et al., *Antiviral Chem. Chemother.,* 4/3: 161–166 (1993); E. V. Connell et al., *Antimicrob. Agents Chemother.,* 38: 348–352 (1994); D. M. Lambert et al., *Antiviral Res.,* 21: 327–342 (1993); A. M. Caliendo et al., *Clin. Infect. Dis.,* 18/4: 516–524 (1994).

The compounds of the invention display antibacterial activity when tested by the microtitration dilution method as described in Heifetz, et al., Antimicr. Agents. & Chemoth. 6: 124 (1974) which is incorporated herein by reference.

By use of the above referenced method, the following minimum inhibitory concentration values (MICs in μg/mL) were obtained for representative compounds of the invention vs. clinically relevant gram positive pathogens which have become highly resistant to conventional therapy in recent years.

Antibacterial Activity μg/ml

| | Antibacterial Activity μg/ml | |
|---|---|---|
| | Ex. 106 | Ex. 142 |
| *Staphylococcus aureus* H228 | 25 | 12.5 |
| *Staphylococcus aureus* UC-76 | 25 | 12.5 |
| *Enterococcus foecalis* MGH2 | 100 | 25 |
| *Streptococcus pneumonia* 5V-1 | 50 | 25 |
| *Streptococcus pyogenes* C203 | 50 | 25 |

It should be apparent to those skilled in the art that other compositions not specifically disclosed in the instant specification are, nevertheless, contemplated thereby. Such other compositions are considered to be within the scope and spirit of the present invention. Hence, the invention should not be limited by the description of the specific embodiments disclosed herein but only by the following claims.

What is claimed is:

1. A compound or a pharmaceutically acceptable salt thereof of formula

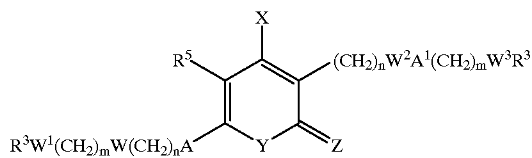

wherein

X is $OR^1$, $NHR^1$, $SR^4$, $CO_2R^4$ or $CH_2OR^1$ wherein $R^1$ is $R^4$ or $COR^4$ wherein $R^4$ is as defined below;

Y is oxygen or sulfur;

Z is oxygen or sulfur;

A and $A^1$ are each independently a chemical bond, an unsubstituted or substituted phenyl, naphthyl, a 5- or 6-membered heterocyclic ring, cycloalkyl, alkylcycloalkyl or a fused ring system of from 8 to 10 atoms or a substituted derivative thereof wherein the substituents are one or more of F, Cl, Br, $OR^4$, $N(R^4)_2$, $CO_2R^4$, $CON(R^4)_2$, $COR^4$, $R^4$, $OCH_2O$, $OCH_2CH_2O$, or C≡N wherein $R^4$ is independently hydrogen, substituted or unsubstituted alkyl, cycloalkyl, alkylcycloalkyl or phenyl wherein the substituents are one or more of $CO_2R^2$, $CON(R^2)_2$, F, $OR^2$, $SR^2$, $N(R^2)_2$, CN, phenyl, naphthyl, a heterocycle or $CF_3$ wherein $R^2$ is independently alkyl, cycloalkyl, or hydrogen;

$R^5$ is hydrogen, alkyl, cycloalkyl, phenyl, or the substituted derivatives thereof wherein the substituents are one or more of $CO_2R^2$, $CON(R^2)_2$, F, $OR^2$, phenyl, naphthyl, $CF_3$, $OR^1$, $NHR^1$, $SR^1$, or $CH_2OR^1$ wherein $R^1$ is as defined above;

$R^3$ is independently hydrogen, $(CH_2)_pR^4$ or $(CH_2)_pA$ wherein p is an integer of from 0 to 2 and $R^4$ and A are as defined above;

W, $W^1$, and $W^3$ are each independently a chemical bond, oxygen, $NR^3$, $C(R^3)_2$, CO, $CR^3{=}CR^3$, C≡C, $CR^3OR^3$, $C(=NR^3)NR^3$, $S(O)_p$, $CR^3N(R^3)_2$, $SO_2NR^3$, $CO_2$, $NR^3COV_gA$ or $NCOV_gR^3$ wherein g is either 0 or 1, and V is oxygen, sulfur, $NR^3$, or $CHR^3$;

$W^2$ is defined in terms of the n of the $(CH_2)_nW^2A^1(CH_2)_mW^3R^3$ group such that if n>0, then $W^2$ is selected from the group consisting of a chemical bond, oxygen, $NR^3$, $C(R^3)_2$, Co, $CR^3{=}CR^3$, C≡C, $CR^3OR^3$, $CR^3N(R^3)_2$, $S(O)_p$ $SO_2NR^3$, $CO_2$, $NR^3COV_gA$ or $NCOV_gR^3$ wherein g is either 0 or 1, and V is oxygen, sulfur, $NR^3$, or $CHR^3$; and if n=0, then $W^2$ is selected from a group consisting of $C(R^3)_2$, CO, $CR^3{=}CR^3$, C≡C, $CR^3OR^3$, $CR^3N(R^3)_2$ and —$CO_2$; and m and n are each independently an integer of from 0 to 4 with the provision that when W and $W^1$ are both heteroatoms or when $W^2$ and $W^3$ are both heteroatoms, m is an integer of from 2 to 4, and with the further proviso that $R^3W^1(CH_2)_mW(CH_2)_nA$ cannot be methyl or ethyl.

2. A compound of the formula of claim 1 wherein

X is selected from the group consisting of OH, $NH_2$ or SH; and $W^2$ is a bond or is selected from the group consisting of $C(R^3)_2$, $CR^3{=}CR^3$, C≡C, $CR^3OR^3$ and $CR^3N(R^3)_2$.

3. A compound of the formula of claim 2 wherein for $(CH_2)_nW^2A^1(CH_2)_mW^3R^3$ n is zero;

$W^2$ is $CHR^3$;

A is a bond;

m is zero; and $W^3$ is S.

4. A compound of the formula of claim 3 selected from the group consisting of 3-[(Cyclohexylthio)phenylmethyl]-4-hydroxy-6-phenyl-2H-pyran-2-one;

4-Hydroxy-3-[[(2-methoxyphenyl)thio]phenylmethyl]-6-phenyl-2H-pyran-2-one;

4-Hydroxy-3-[3-methyl-1-(phenylthio)butyl]-6-phenyl-2H-pyran-2-one;

4-Hydroxy-6-phenyl-3-[phenyl[(phenylmethyl)thio]methyl]-2H-pyran-2-one;

4-Hydroxy-6-phenyl-3-[phenyl(phenylthio)methyl]-2H-pyran-2-one;

4-Hydroxy-3-[2-naphthalenyl(phenylthio)methyl]-6-phenyl-2H-pyran-2-one;

4-Hydroxy-3-[(2-naphthalenylthio)phenylmethyl]-6-phenyl-2H-pyran-2-one;

6-(3,5-Dimethylphenyl)-4-hydroxy-5-methyl-3-[2-phenyl-1-[(phenylmethyl)thio]ethyl]-2H-pyran-2-one;

4-Hydroxy-6-[4-(2-methoxyphenoxy)phenyl]-3-[phenyl[(phenylmethyl)thio]methyl]-2H-pyran-2-one;

4-Hydroxy-6-[5-(phenoxymethyl)-2-furanyl]-3-[2-phenyl-1-[(phenylmethyl)thio]ethyl]-2H-pyran-2-one;

Cis-6-(3,5-Dimethylphenyl)-4-hydroxy-3-[3-methyl-1-[2,3-dihydro-1-hydroxy-1H-inden-2-yl)thio]butyl]-2H-pyran-2-one;

4-Hydroxy-6-phenyl-3-[phenyl[(phenylmethyl)thio]methyl]-2H-pyran-2-one;

4-Hydroxy-3-[[(2-methoxyphenyl)thio]phenylmethyl]-6-phenyl-2H-pyran-2-one;

4-Hydroxy-3-[3-methyl-1-(phenylthio)butyl]-6-phenyl-2H-pyran-2-one;

4-Hydroxy-3-[4-methyl-1-(phenylthio)pentyl]-6-phenyl-2H-pyran-2-one;

3-[1-[(2,6-Dimethylphenyl)thio]-3-methylbutyl]-4-hydroxy-6-phenyl-2H-pyran-2-one;

3-[1-[(2,6-Dichlorophenyl)thio]-3-methylbutyl]-4-hydroxy-6-phenyl-2H-pyran-2-one;

3-[1-Cyclohexylthio)-3,3-dimethylbutyl]-4-hydroxy-6-phenyl-2H-pyran-2-one;

3-[1-(Cyclopentylthio)-3-methylbutyl]-4-hydroxy-6-phenyl-2H-pyran-2-one;

3-[(Cyclohexylthio)phenylmethyl]-4-hydroxy-6-phenyl-2H-pyran-2-one;

3-[1-(Cyclohexylthio)-3-methylbutyl]-6-(2,3-dihydro-1,4-benzodioxin-6-yl)4-hydroxy-2H-pyran-2-one;

4-Hydroxy-3-[1-[(2-methoxyphenyl)thio]-3-methylbutyl]-6-phenyl-2H-pyran-2-one;

4-Hydroxy-3-[1-[(phenylmethyl)thio]-3-methylbutyl]-6-phenyl-2H-pyran-2-one and

3-[1-(Cyclohexylthio)-3-methylbutyl]-4-hydroxy-6-phenyl-2H-pyran-2-one.

5. A compound of the formula of claim 3 selected from the group consisting of

3-[2-Cyclohexyl-1-(phenylthio)ethyl]-4-hydroxy-6-phenyl-2H-pyran-2-one;

3-[1,4-Bis(phenylthio)butyl]-4-hydroxy-6-phenyl-2H-pyran-2-one;

3-[2-Cyclohexyl-1-(phenylthio)ethyl]-4-hydroxy-6-phenyl-2H-pyran-2-one;

3-[2-Cyclohexyl-1-(cyclohexylthio)ethyl]-4-hydroxy-6-phenyl-2H-pyran-2-one;

3-[1-(Cyclohexylthio)-2-cyclopropylethyl]-4-hydroxy-6-phenyl-2H-pyran-2-one;

3-[1-(Cyclohexylthio)-2-(cyclopentyl)ethyl]-4-hydroxy-6-phenyl-2H-pyran-2-one and 3-[2-Cyclopropyl-1-[(phenylmethyl)thio]ethyl]-4-hydroxy-6-phenyl-2H-pyran-2-one.

6. A compound of the formula of claim 3 wherein $R^3W^1(CH_2)_mW(CH_2)_nA$ is defined such that $R^3$ in $R^3W^1$ is a heterocycle or a fused heterocyclic ring;

m is not zero;

W is S or O;

n is zero; and

A is not a bond.

7. A compound of the formula of claim 6 selected from the group consisting of

6-[4-(3-Furanylmethoxy)phenyl]-4-hydroxy-3-[3-methyl-1-[(phenylmethyl)thio]butyl]-2H-pyran-2-one and 3-[(Cyclohexylthio)phenylmethyl]-4-hydroxy-6-[3-methyl-4-(3-pyridinylmethoxy)phenyl]-2H-pyran-2-one.

8. A compound of the formula of claim 3 wherein $R^3W^1(CH_2)_mW(CH_2)_nA$ is defined such that A forms a spirocyclic ring.

9. A compound of the formula of claim 8 selected from the group consisting of 6-(1-Benzylcyclopropyl)-3-[cyclopentyl(cyclopropylmethylthio)methyl]-4-hydroxy-2H-pyran-2-one;

6-(1-Benzylcyclobutyl)-3-[cyclopentyl(cyclopropylmethylthio)methyl]-4-hydroxy-2H-pyran-2-one;

6-(1-Benzyldyclopentyl)-3-[1-(cyclopentylthio)-2-cyclopropylethyl]-4-hydroxy-2H-pyran-2-one and 6-(1-Benzylcyclopentyl)-3-[1-(cyclopentylthio)-3-methylbutyl]-4-hydroxy-2H-pyran-2-one.

10. A compound of the formula of claim 2 wherein for $(CH_2)_nW^2A^1(CH_2)_mW^3R^3$ n is 0 or 1; and $W^2$ is selected from the group consisting of $CR^3OR^3$, $CR^3N(R^3)_2$, and, $C(R^3)_2$ with the limitation that in $C(R^3)_2$, the carbon is attached to no hydrogens directly.

11. A compound of the formula of claim 10 selected from the group consisting of

[4-[3-[2-Cyclopentyl-1-(phenylmethoxy)ethyl]-4-hydroxy-2-oxo-2H-pyran-6-yl]phenoxy]acetic acid;

6-(3,5-Dimethylphenyl)-4-hydroxy-3-[1-hydroxy-2-methyl-1-(phenylmethyl)propyl]-2H-pyran-2-one;

[2-(Hydroxymethyl)-4-[4-hydroxy-3-[1-(1-methylethoxy)-2-(phenylthio)ethyl]-2-oxo-2H-pyran-6-yl]phenoxy] acetic acid;

[4-[4-Hydroxy-2-oxo-3-[2-phenyl-1-[(phenyl-methyl) amino]ethyl]-2H-pyran-6-yl]phenoxy]acetic acid and 4-Hydroxy-3-[2-phenyl-1-[phenyl(phenyl-methyl)amino] ethyl]-6-[4-(3-pyridinylmethoxy)phenyl]-2H-pyran-2-one.

12. A compound of the formula of claim 2 wherein $W^2$ is selected from the group consisting of $CHR^3$, $CR^3{=}CR^3$ and $C{\equiv}C$.

13. A compound of the formula of claim 12 selected from the group consisting of

4-[4-Hydroxy-3-[1-(1-hydroxy-2-phenylethyl)-3-methylpentyl]-2-oxo-2H-pyran-6-yl]benzenepropanoic acid;

[4-[4-Hydroxy-3-[3-methyl-2-(phenylthio)butyl]-2-oxo-2H-thiopyran-6-yl]phenoxy]acetic acid;

[2-Hydroxy-4-[4-hydroxy-2-oxo-3-[2-(phenylmethylene) pentyl]-2H-pyran-6-yl]phenoxy]acetic acid;

N-[3-[Cyclopropyl[6-(1,1-dimethyl-3-phenylpropyl)-4-hydroxy-2-oxo-2H-pyran-3-yl]methyl]phenyl] benzenesulfonamide;

3-(Cyclopropylphenylmethyl)-6-(1,1-dimethyl-3-phenylpropyl)-4-hydroxy-2H-pyran-2-one;

N-[3-[Cyclopropyl[6-(1,1-dimethyl-3-phenylpropyl)-4-hydroxy-2-oxo-2H-pyran-3-yl]methyl]phenyl] benzenesulfonamide;

N-[3-[Cyclopropyl[6-(1,1-dimethyl-2-phenylethyl)-4-hydroxy-2-oxo-2H-pyran-3-yl]methyl]phenyl] benzenesulfonamide;

N-[3-[Cyclopropyl[4-hydroxy-6-(1-methyl-1-phenylethyl)-2-oxo-2H-pyran-3-yl]methyl]phenyl] benzenesulfonamide;

N-[3-[Cyclopropyl[6-(1,1-diethyl-3-phenylpropyl)-4-hydroxy-2-oxo-2H-pyran-3-yl]methyl]phenyl] benzenesulfonamide;

N-[3-[Cyclopropyl[6-[1-ethyl-1-(phenylmethyl)propyl]-4-hydroxy-2-oxo-2H-pyran-3-yl]methyl]phenyl] benzenesulfonamide;

N-[3-[Cyclopropyl[6-(1-ethyl-1-phenylpropyl)-4-hydroxy-2-oxo-2H-pyran-3-yl]methyl]phenyl] benzenesulfonamide;

3-(Cyclopropylphenylmethyl)-6-(1,1-dimethyl-3-phenylpropyl)-4-hydroxy-2H-pyran-2-one;

3-(Cyclopropylphenylmethyl)-6-(1,1-dimethyl-2-phenylethyl)-4-hydroxy-2H-pyran-2-one;

3-(Cyclopropylphenylmethyl)-4-hydroxy-6-(1-methyl-1-phenylethyl)-2H-pyran-2-one;

3-(Cyclopropylphenylmethyl)-6-(1,1-diethyl-3-phenylpropyl)-4-hydroxy-2H-pyran-2-one and 6-(1-Benzyl-1-ethylpropyl)-3-(cyclopropylphenylmethyl)-4-hydroxy-2H-pyran-2-one and 3-(Cyclopropylphenylmethyl)-6-[1-ethyl-1-phenylpropyl]-4-hydroxy-2H-pyran-2-one.

14. A compound of the formula of claim 12 wherein $R^3W^1(CH_2)_mW(CH_2)_nA$ is defined such that $R^3$ in $R^3W^1$ is a heterocycle or a fused heterocyclic ring;

m is not zero;

W is S or O;

n is zero; and

A is not a bond.

15. A compound of the formula of claim 14 selected from the group consisting of 3-(Cyclopropylphenylmethyl)-4-hydroxy-6-[4-(pyridin-3-ylmethoxy)phenyl]-2H-pyran-2-one;

N-[3-[Cyclopropyl[4-hydroxy-2-oxo-6-[4-(pyridin-3-ylmethoxy)phenyl]-2H-pyran-3-yl]methyl]phenyl]benzenesulfonamide and 4-Hydroxy-3-(1-phenylpropyl)-6-[4-(pyridin-3-ylmethoxy)phenyl]-2H-pyran-2-one.

16. A compound of the formula of claim 12 wherein $R^3W^1(CH_2)_mW(CH_2)_nA$ is defined such that A forms a spirocyclic ring.

17. A compound of the formula of claim 16 selected from the group consisting of

N-[3-[Cyclopropyl[4-hydroxy-2-oxo-6-[1-(2-phenylethyl)cyclopentyl]-2H-pyran-3-yl]methyl]phenyl]-benzenesulfonamide;

N-[3-[[6-(1-Benzylcyclopropyl)-4-hydroxy-2-oxo-2H-pyran-3-yl]cyclopropylmethyl]phenyl]-benzenesulfonamide;

N-[3-[Cyclopropyl[4-hydroxy-2-oxo-6-[1-(2-phenylethyl)cyclopentyl]-2H-pyran-3-yl]methyl]phenyl]benzenesulfonamide;

N-[3-[[6-(1-Benzylcyclopentyl)-4-hydroxy-2-oxo-2H-pyran-3-yl]cyclopropylmethyl]phenyl]benzenesulfonamide;

N-[3-[Cyclopropyl[4-hydroxy-2-oxo-6-[-1(3-phenypropyl)cyclopentyl]-2H-pyran-3-yl]methyl]phenyl]benzenesulfonamide;

N-[3-[Cyclopropyl[4-hydroxy-2-oxo-6-[1-(2-phenylethyl)cyclobutyl]-2H-pyran-3-yl]methyl]phenyl]benzenesulfonamide;

N-[3-[[6-(1-Benzylcyclobutyl)-4-hydroxy-2-oxo-2H-pyran-3-yl]cyclopropyl]methyl]phenyl]benzenesulfonamide;

N-[3-[Cyclopropyl[4-hydroxy-2-oxo-6-[1-(3-phenylpropyl)cyclobutyl]-2H-pyran-3-yl]methyl]phenyl]benzenesulfonamide;

N-[3-[Cyclopropyl[4-hydroxy-2-oxo-6-[1-(2-phenylethyl)cyclopropyl]-2H-pyran-3-yl]methyl]phenyl]benzenesulfonamide;

N-[3-[[6-(1-Benzylcyclopropyl)-4-hydroxy-2-oxo-2H-pyran-3-yl]cyclopropylmethyl]phenyl]benzenesulfonamide and N-[3-[Cyclopropyl[4-hydroxy-2-oxo-6-[1-(3-phenylpropyl)cyclopropyl]-2H-pyran-3-yl]methyl]phenyl]benzenesulfonamide.

18. A compound of the formula of claim 2 wherein $(CH_2)_nW^2A^1(CH_2)_mW^3R^3$ is defined such that n is 0;

$W^2$ is a bond; and $A^1$ is not a bond.

19. A compound of the formula of claim 18 selected from the group consisting of 6-(1-Benzylpropyl)-4-hydroxy-3-(2-isobutyl-5-isopropylphenyl)-2H-pyran-2-one;

6-(1-Benzylpropyl)-4-hydroxy-3-(2-methyl-5,6,7,8-tetrahydro-naphthalen-1-yl)-2H-pyran-2-one;

3-(3-Cyclopropylmethyl-5-isopropylphenyl)-4-hydroxy-6-[4-(pyridin-3-ylmethoxy)phenyl]-2H-pyran-2-one and 3-(3,5-Diisopropylphenyl)-4-hydroxy-6-[4-(pyridin-3-ylmethoxy)phenyl]-2H-pyran-2-one.

* * * * *